US012083136B2

(12) United States Patent
Yang et al.

(10) Patent No.: US 12,083,136 B2
(45) Date of Patent: *Sep. 10, 2024

(54) COMBINATION OF BCL-2/BCL-XL INHIBITORS AND CHEMOTHERAPEUTIC AGENT AND USE THEREOF

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Guangfeng Wang, Suzhou (CN); Douglas Dong Fang, Suzhou (CN); Jing Deng, Suzhou (CN); Miaozhen Qiu, Suzhou (CN); Lin Zhang, Suzhou (CN)

(73) Assignee: ASCENTAGE PHARMA (SUZHOU) CO., LTD, Suzhou (CN)

( * ) Notice: Subject to any disclaimer, the term of this patent is extended or adjusted under 35 U.S.C. 154(b) by 155 days.

This patent is subject to a terminal disclaimer.

(21) Appl. No.: 16/630,855

(22) PCT Filed: Jul. 31, 2019

(86) PCT No.: PCT/CN2019/098576
§ 371 (c)(1),
(2) Date: Jan. 14, 2020

(87) PCT Pub. No.: WO2020/024976
PCT Pub. Date: Feb. 6, 2020

(65) Prior Publication Data
US 2021/0060039 A1 Mar. 4, 2021

(30) Foreign Application Priority Data

| Jul. 31, 2018 | (CN) | 201810914839.4 |
| Feb. 12, 2019 | (WO) | PCT/CN2019/074862 |
| Jul. 4, 2019 | (CN) | 201910598720.5 |
| Jul. 22, 2019 | (CN) | 201910662265.0 |

(51) Int. Cl.
| *A61K 31/675* | (2006.01) |
| *A61K 9/00* | (2006.01) |
| *A61K 31/337* | (2006.01) |
| *A61K 31/4045* | (2006.01) |
| *A61K 31/4745* | (2006.01) |
| *A61K 31/496* | (2006.01) |
| *A61K 31/513* | (2006.01) |
| *A61K 33/243* | (2019.01) |
| *A61P 35/00* | (2006.01) |
| *A61P 35/04* | (2006.01) |

(52) U.S. Cl.
CPC .......... *A61K 31/675* (2013.01); *A61K 31/337* (2013.01); *A61K 31/4045* (2013.01); *A61K 31/4745* (2013.01); *A61K 31/496* (2013.01); *A61K 31/513* (2013.01); *A61K 33/243* (2019.01); *A61P 35/00* (2018.01); *A61P 35/04* (2018.01)

(58) Field of Classification Search
CPC .............. A61K 31/4745; A61K 31/513; A61K 31/496; A61K 31/4085; A61K 31/337; A61P 35/00; A61P 35/04
See application file for complete search history.

(56) References Cited

U.S. PATENT DOCUMENTS

| 7,432,304 | B2 | 10/2008 | Wang et al. |
| 7,981,605 | B2* | 7/2011 | Freeman ................. A61P 35/04 435/6.11 |
| 2007/0027135 | A1 | 2/2007 | Bruncko et al. |
| 2010/0278921 | A1 | 11/2010 | Fischer et al. |

FOREIGN PATENT DOCUMENTS

| WO | 2012/017251 A1 | 2/2012 |
| WO | 2014/113413 A1 | 7/2014 |
| WO | 2015/157120 A1 | 10/2015 |

OTHER PUBLICATIONS

Emi et al. Breast Cancer Research 7, R940-R952 (2005).*
Drugs.com (2000).*
Clegg et al. Clinical and cost effectiveness of Paclitacel (2001).*
Dakes, S. R. et al., "Sensitization of BCL-2-expressing breast tumors to chemotherapy by the BH3 mimetic ABT-737" PNAS (2012), vol. 109, No. 8, pp. 2766-2771.

(Continued)

*Primary Examiner* — Shirley V Gembeh
(74) *Attorney, Agent, or Firm* — Jun He Law Offices P.C; James J. Zhu

(57) ABSTRACT

The present disclosure provides a pharmaceutical composition comprising a Bcl-2/Bcl-xL inhibitor, a chemotherapeutic agent, and a pharmaceutically acceptable carrier. The present disclosure also provides a method of treating cancer, comprising administering to a subject in need thereof a therapeutically effective amount of a Bcl-2/Bcl-xL inhibitor and a therapeutically effective amount of a chemotherapeutic agent. The present disclosure also provides use of a combination of a Bcl-2/Bcl-xL inhibitor and a chemotherapeutic agent in the manufacture of an anti-tumor medicament. In the present disclosure, a significantly enhanced anti-tumor effect can be achieved by administration of a Bcl-2/Bcl-xL inhibitor in combination with a chemotherapeutic agent.

4 Claims, 36 Drawing Sheets

(56) References Cited

OTHER PUBLICATIONS

Sagara, A. et al., "Intrinsic Resistance to 5-Fluorouracil in a Brain Metastatic Variant of Human Breast Cancer Cell Line, MDA-MB-231BR", Plos One (2016), vol. 11, No. 10, e0164250.

Kasai, S. et a., "Bcl-2/Bcl-xL inhibitor ABT-737 sensitizes pancreatic ductal adenocarcinoma to paclitaxel-induced cell death", Oncology Letters (2017), vol. 14, pp. 903-908.

Watanabe, A. et al., "BCL2 and BCLXL are key determinants of resistance to antitubulin chemotherapeutics in melanoma cells", Experimental Dermatology (2013), vol. 22, pp. 518-523.

Wong, M. et al., "Navitaclax (ABT-263) Reduces Bcl-xL-Mediated Chemoresistance In Ovarian Cancer Models", Molecular Cancer Therapeutics (2012), vol. 11, No. 4, pp. 1026-1035.

Zhang, F. et al., "ABT-737 potentiates cisplatin-induced apoptosis in human osteosarcoma cells via the mitochondrial apoptotic pathway", Oncology Reports (2017), vol. 38, pp. 2301-2308.

Dai, Y. et al., "The involvement of Bcl-2 family proteins in AKT-regulated cell survival in cisplatin resistant epithelial ovarian cancer", Oncotarget (2017), vol. 8, No. 1, pp. 1354-1368.

Kim, E. Y. et al., "Abstract 2530: Bcl-2 and Bcl-xL dual inhibitor ABT-737, circumvents JNK mediated upregulation of anti-apoptotic molecules in cisplatin treated non-small cell lung cancer models", Cancer Research (2015), vol. 75, Issue 15 Supplement, abstract 2530.

Kim, E. Y. et al., "ABT-737 Synergizes with Cisplatin Bypassing Aberration of Apoptotic Pathway in Non-Small cell Lung Cancer", Neoplasia (2017), vol. 19, No. 4, pp. 354-363.

Li, R. et al., "ABT-737 Synergizes with Chemotherapy to Kill Head and Neck Squamous Cell Carcinoma Cells via a Noxa-Mediated Pathway", Molecular Pharmacology (2009), vol. 75, No. 5, pp. 1231-1239.

Matsumoto, M. et al., "Cisplatin-induced apoptosis in non-small-cell lung cancer cells is dependent on Bax- and Bak-induction pathway and synergistically activated by BH3-mimetic ABT-263 in p53 wild-type and mutant cells", Biochemical and Biophysical Research Communication (2016), vol. 473, pp. 490-496.

Lieber, J. et al., "Increased efficacy of CDDP in a xenograft model of hepatoblastoma using the apoptosis sensitizer ABT-737", Oncology Reports (2013), vol. 29, pp. 646-652.

Ma, Z. et al., "Asymmetric dipolar cycloaddition reactions: a practical, convergent synthesis of chiral pyrrolidines", Tetrahedron: Asymmetry (1997), vol. 8(6), pp. 883-887.

Huang, S. et al., "BCL-W is a regulator of microtubule inhibitor-induced mitotic cell death", Oncotarget (2016), vol. 7 (25), pp. 38718-38730.

Okumura, K. et al., "Induction of Noxa Sensitizes Human Colorectal Cancer Cells Expressing Mcl-1 to the Small-Molecule Bcl-2/Bcl-xL Inhibitor, ABT-737", Clinical Cancer Research (Dec. 2008), vol. 14(24), pp. 8132-8142.

Shi, J. et al., "Navitoclax (ABT-263) Accelerates Apoptosis during Drug-Induced Mitotic Arrest by Antagonizing Bcl-xL", Cancer Research (Jul. 2011), vol. 71(13), pp. 4518-4526.

Bah, N. et al., "Bcl-xL controls a switch between cell death modes during mitotic arrest", Cell Death & Disease (2014), vol. 5, pp. e1291-e1291. doi: 10.1038/cddis.2014.251.

Nagano, T. et al., "Mechanism of Resistance to Epidermal Growth Factor Receptor-Tyrosine Kinase Inhibitors and a Potential Treatment Strategy", Cells (2018), vol. 7, 212; doi: 10.3390/cells7110212. p. 1-16.

A study of APG-1252 in Patients with SCLC or Other Solid Tumors, NCT03080311, retrieved from https://clinicaltrials.gov/ct2/show/NCT03080311?term=APG-1252&draw=2&rank=2,on Apr. 17, 2020. Published on Mar. 15, 2017.

APG-1252 in Patients with SCLC or Advanced Solid Tumors, NCT03387332, retrieved from https://clinicaltrials.gov/ct2/show/NCT03387332?term=APG-1252&draw=2&rank=1,on Apr. 17, 2020. Published on Jan. 2, 2018.

A study of the safety, pharmacokinetic and pharmacodynamic properties of a novel anticancer drug APG-1252 in patients with small cell lung cancer or other solid tumors, ACTRN12616001597482, retrieved from https://www.anzctr.org.au/Trial/Registration/TrialReview.aspx?id=371737, on Apr. 17, 2020.Published on Nov. 2, 2016.

A Ph I/II study of APG-1252 in patient with SCLC or other solid tumors, CTR20170976.Published on Nov. 23, 2017.

Lakhani, N. J. et al., "A phase I study of novel dual Bcl-2/Bcl-xL inhibitor APG-1252 in patients with advanced small cell lung cancer (SCLC) or other solid tumor", Journal of Clinical Oncology (May 2018), vol. 36(15_suppl), pp. 2594-2594.

Tije et al. Weekly paclitaxel as first-line chemotherapy for elderly patients with metastatic breast cancer. A multicentre phase II trial, European J. of Cancer 40 (2004): 352-357.

* cited by examiner

IC$_{50}$ μM in MDA-MB-231 TNBC (WST assay; 72hr)

COMBINATION OF BCL-2/BCL-XL INHIBITORS AND CHEMOTHERAPEUTIC AGENT AND USE THEREOF

FIELD OF THE INVENTION

The present disclosure relates to a pharmaceutical composition and use thereof in the treatment of cancer, and a method of treating cancer comprising a Bcl-2/Bcl-xL inhibitor and a chemotherapeutic agent.

BACKGROUND

Apoptosis is a natural pathway for the body to clear abnormal or unwanted cells, and if it is affected, it may lead to various diseases such as cancer. Bcl-2 family proteins are important regulators of apoptosis. The family of proteins includes anti-apoptotic proteins such as Bcl-2, Bcl-xL and Mcl-1; and pro-apoptotic molecules, including Bid, Bim, Bad, Bak and Bax. Although normal cells have low expression levels of anti-apoptotic Bcl-2 and Bcl-xL proteins, these proteins are found to be highly overexpressed in many different types of human tumors and are implied in tumor development, progression and resistance to drugs. Targeting Bcl-2 and/or Bcl-xL has been investigated as a cancer treatment strategy.

The first generation Bcl-2/Bcl-xL inhibitors ABT-737 and ABT-263 are small molecule Bcl-2 inhibitors developed by Abbott Laboratories, USA. ABT-737 and ABT-263 have been reported to bind Bcl-2, Bcl-xL and Bcl-w (Ki<1 nM) with high affinity, and the binding has a higher specificity than their binding to Mcl-1 and A1 (two other anti-apoptotic Bcl-2 proteins). In addition, a second generation Bcl-2/Bcl-xL inhibitor has been disclosed in WO 2014/113413 A1, which binds to Bcl-2 and/or Bcl-xL, with a Ki value of <10 nM, and functions as a potent antagonist of Bcl-2 and Bcl-xL in cell-free function assays.

Combination therapy of anti-cancer drugs is sometimes used in the treatment of cancer. There exists needs for a combination of a Bcl-2/Bcl-xL inhibitor having high anti-cancer activity and low side effects and other anti-cancer agents.

SUMMARY OF INVENTION

It is an intent of the present disclosure to provide a pharmaceutical composition having a notable anti-cancer effect, a method for treating cancer, and use of the pharmaceutical composition.

According to a first aspect of the present disclosure, provided herein is a pharmaceutical composition comprising a Bcl-2/Bcl-xL inhibitor and a chemotherapeutic agent, and a pharmaceutically acceptable carrier. The Bcl-2/Bcl-xL inhibitor is a compound of the following formula (I), (II), (III) or (IV), or a pharmaceutically acceptable salt thereof:

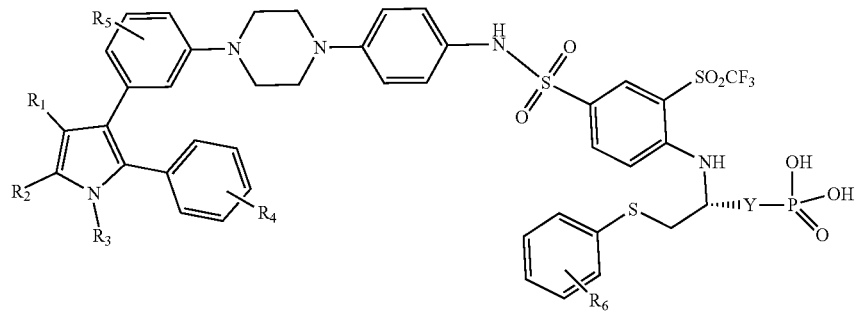

(I)

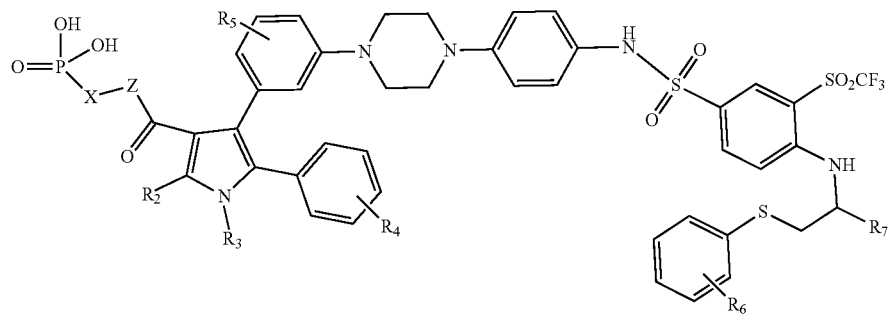

(II)

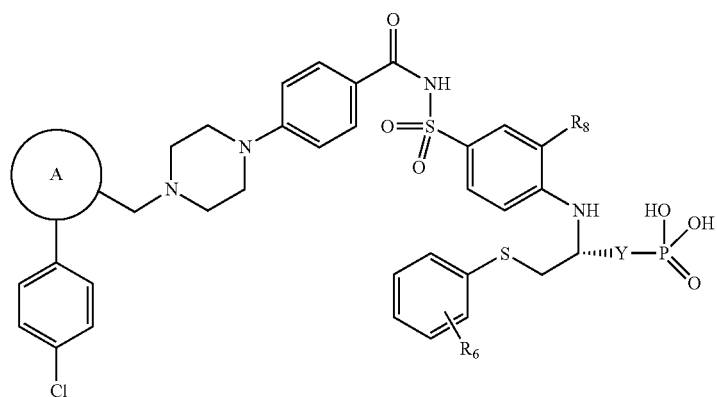

(III)

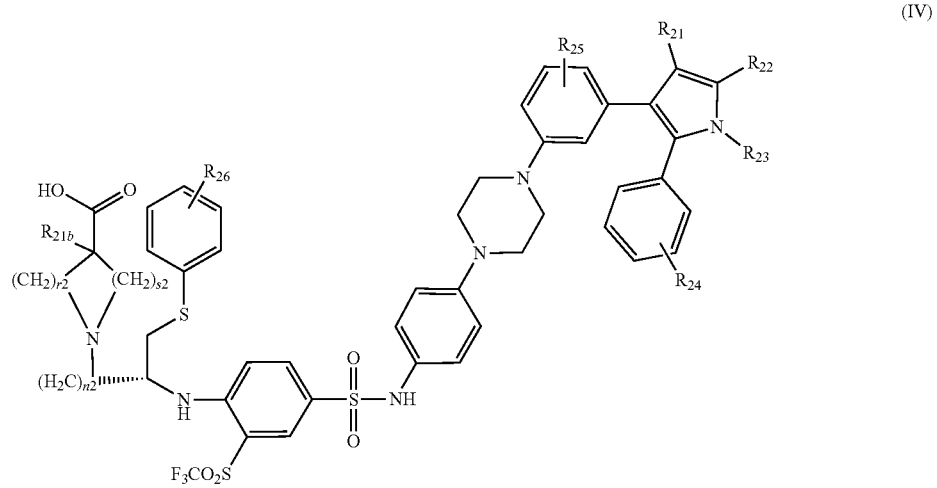

(IV)

wherein the A ring is

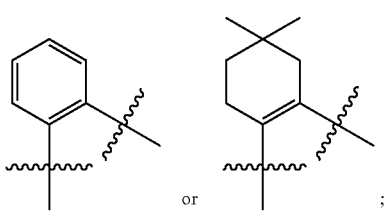

X, substituted or unsubstituted, is selected from the group consisting of alkylene, alkenylene, cycloalkylene, cycloalkenylene, and heterocycloalkylene; Y is selected from the group consisting of $(CH_2)_n$—$N(R^a)_2$ and

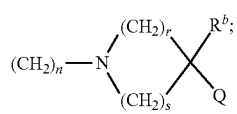

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;
Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'SO$_2$R", NR'COR", NR'CONR"R", NR'C=SNR"R", NR'SO$_2$R", SO$_2$R', and SO$_2$NR'R";

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COR', CONR'R", CONR'SO$_2$R", $C_{1-3}$alkyleneCH(OH)CH$_2$OH, SO$_2$R', and SO$_2$NR'R"; R', R", and R'", independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R", or R" and R'", can be taken together with the atom to which they are bound to form a 3 to 7 membered ring;

$R_4$ is hydrogen, halo, $C_{1-3}$alkyl, $CF_3$, or CN;

$R_5$ is hydrogen, halo, $C_{1-3}$alkyl, substituted $C_{1-3}$alkyl, hydroxyalkyl, alkoxy, or substituted alkoxy;

$R_6$ is selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'SO$_2$R", NR'COR", NR'CONR"R", NR'C=SNR"R", NR'SO$_2$R", SO$_2$R', and SO$_2$NR'R";

$R_7$, substituted or unsubstituted, is selected form the group consisting of hydrogen, alkyl, alkenyl, $(CH_2)_{0-3}$cycloalkyl, $(CH_2)_{0-3}$cycloalkenyl, $(CH_2)_{0-3}$heterocycloalkyl, $(CH_2)_{0-3}$aryl, and $(CH_2)_{0-3}$heteroaryl;

R₈ is selected form the group consisting of hydrogen, halo, NO₂, CN, CF₃SO₂, and CF₃;

R_a is selected from the group consisting of hydrogen, alkyl, heteroalkyl, alkenyl, hydroxyalkyl, alkoxy, substituted alkoxy, cycloalkyl, cycloalkenyl, and heterocycloalkyl;

R_b is hydrogen or alkyl;

R_c is selected from the group consisting of hydrogen, alkyl, substituted alkyl, hydroxyalkyl, alkoxy, and substituted alkoxy;

n, r, and s, independently, are 1, 2, 3, 4, 5, or 6;

$R_{21}$ is $SO_2R_{2'}$, $R_{22}$ is alkyl, preferably $C_{1-4}$ alkyl, more preferably methyl, propyl, or isopropyl, $R_{23}$ is alkyl, preferably $C_{1-4}$ alkyl, more preferably methyl, propyl, or isopropyl, $R_{24}$ is halogen, preferably fluoride, chloride, $R_{25}$ is halogen, preferably fluoride, chloride, $R_{26}$ is selected from H, halogen, alkyl, preferably fluoride, chloride, $C_{1-4}$ alkyl, more preferably methyl, propyl, isopropyl $R_{21b}$ is H or alkyl, preferably $C_{1-4}$ alkyl, more preferably methyl, propyl, or isopropyl, $n_2$, $r_2$ and $s_2$ are independently 1, 2, 3, 4, 5 or 6, more preferably, $r_2$ and $s_2$ are both 2 and $n_2$ is 3, 4 or 5, more preferably, all of $n_2$, $r_2$ and $s_2$ are 2; and $R_2'$ is alkyl, preferably $C_{1-4}$ alkyl, more preferably methyl, propyl, or isopropyl.

Compounds of the above formula (I), (II) or (III) have been disclosed in WO 2014/113413 A1, which is incorporated herein by reference to its entirety. The above formula (IV) is disclosed in PCT/CN2019/070508, which is incorporated herein by reference.

According to a second aspect of the invention, provided herein is a method of treating cancer comprising administering a therapeutically effective amount of a Bcl-2/Bcl-xL inhibitor and a therapeutically effective amount of a chemotherapeutic agent to an individual in need thereof.

According to a third aspect of the invention, provided herein is use of a combination of a Bcl-2/Bcl-xL inhibitor and a chemotherapeutic agent for the manufacture of a medicament for the treatment of cancer.

The pharmaceutical composition of the present disclosure has an excellent anti-cancer effect, and in particular, the anti-cancer effect of the combination of the Bcl-2/Bcl-xL inhibitor and the chemotherapeutic agent of the present disclosure is superior to the sum of the therapeutic effects of the respective individual components, i.e., the pharmaceutical composition of the present disclosure achieves an excellent synergistic effect.

Figure 21:
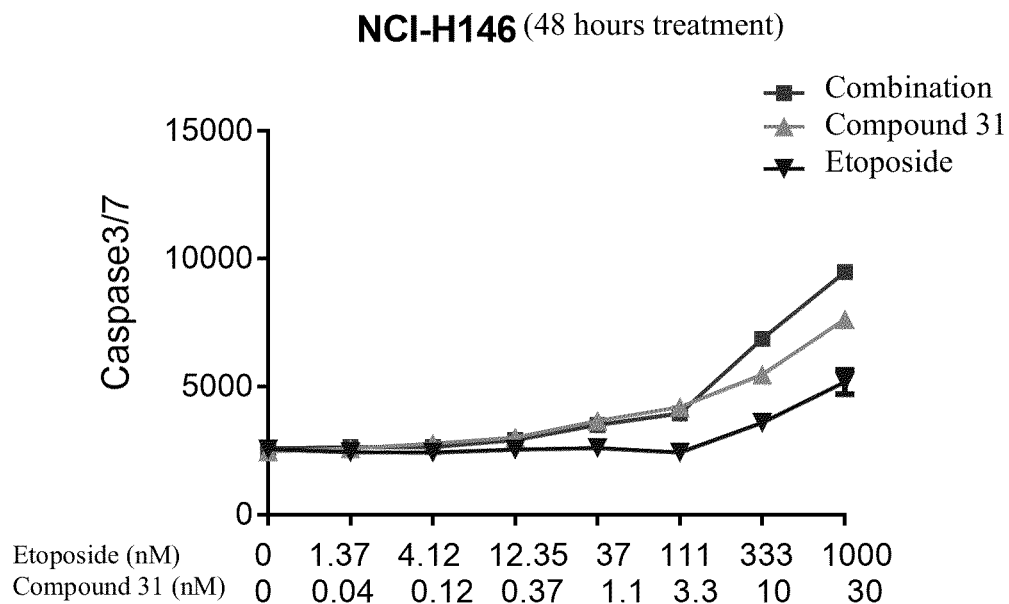
FIG. 21 shows that caspase 3/7 activity increases in the human small cell lung cancer cell lines NCI-H146 (FIG.
Figure 21:
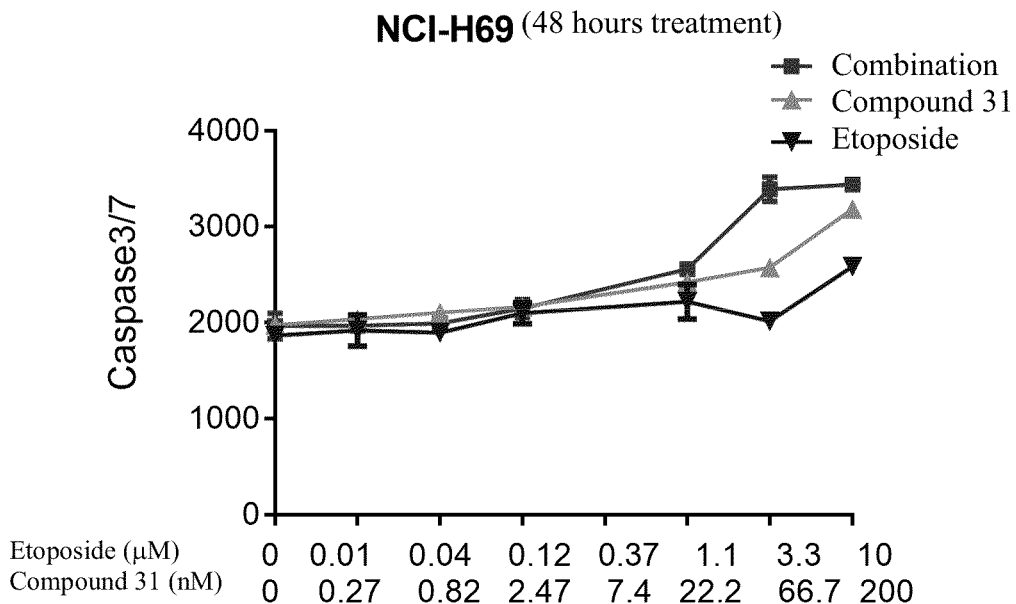

21(*a*)) and NCI-H69 (FIG. 21(*b*)) treated with Compound 31 in combination with etoposide.

Figure 22:
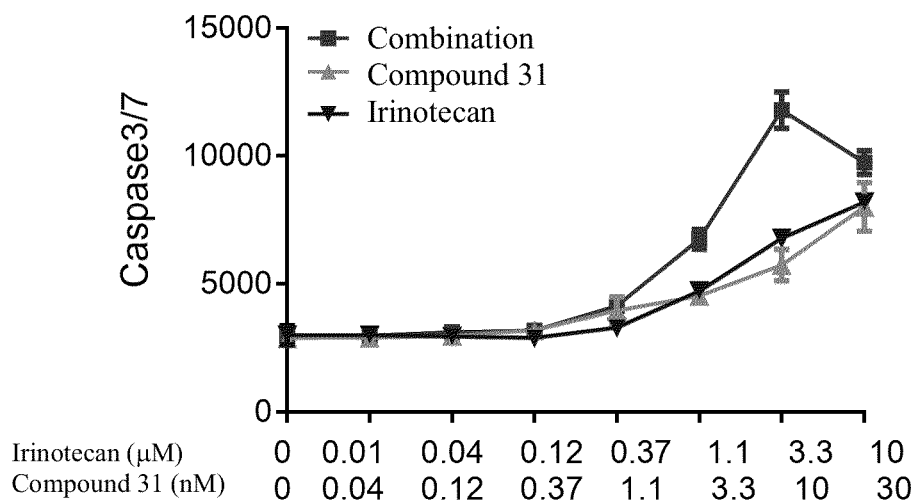
Figure 22:
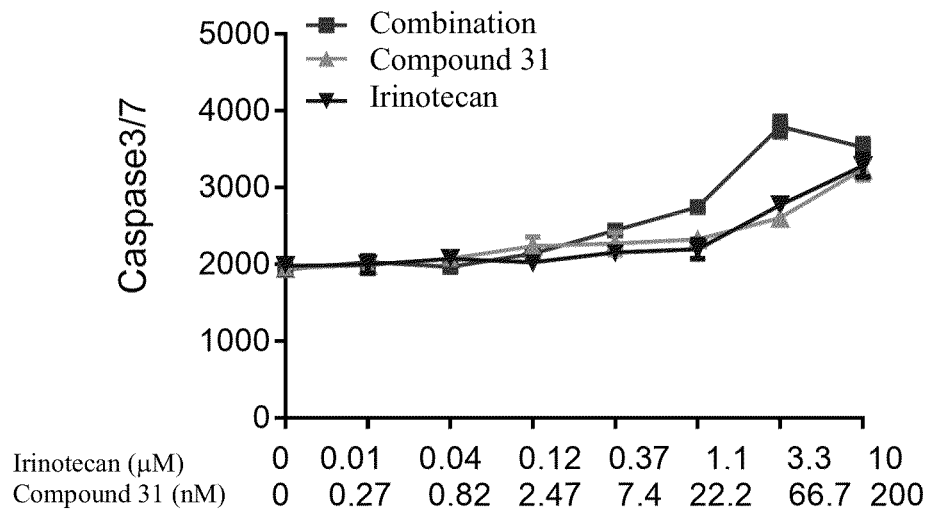

FIG. 22 shows that caspase 3/7 activity increases in the human small cell lung cancer cell lines NCI-H146 (FIG. 22(*a*)) and NCI-H69 (FIG. 22(*b*)) treated with Compound 31 in combination with irinotecan.

Figure 23:
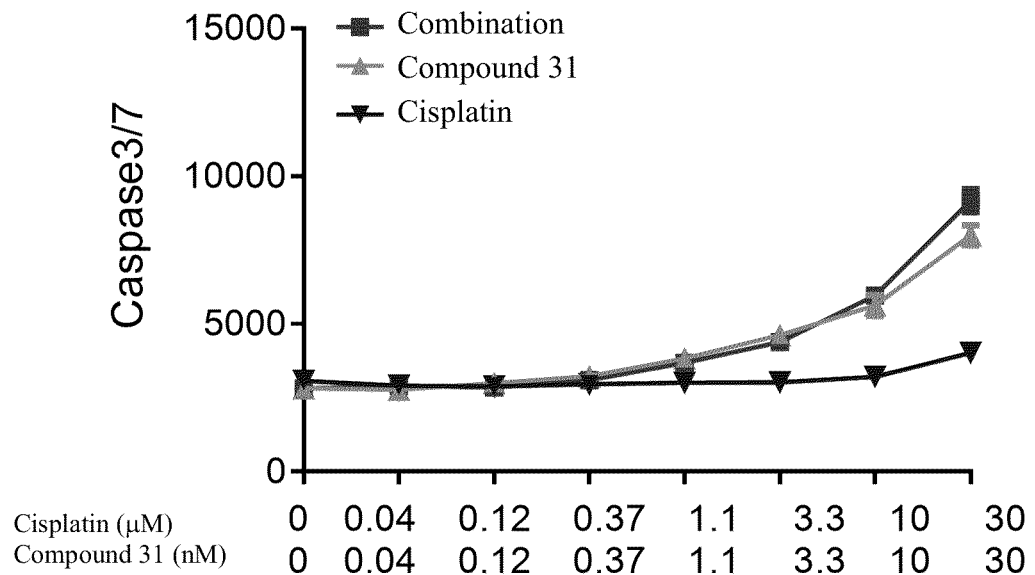
Figure 23:
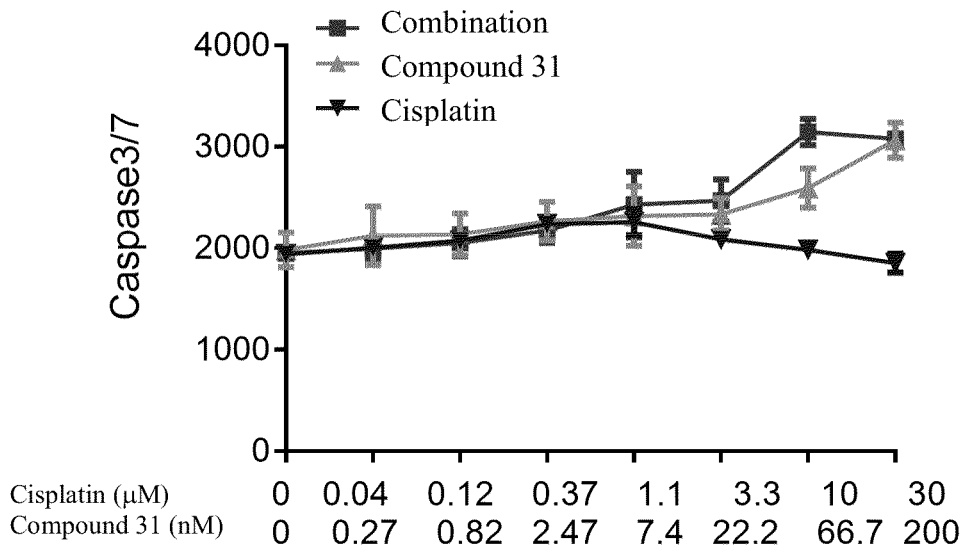

FIG. 23 shows that caspase 3/7 activity increases in the human small cell lung cancer cell lines NCI-H146 (FIG. 23(*a*)) and NCI-H69 (FIG. 23(*b*)) treated with Compound 31 in combination with cisplatin.

Figure 24:
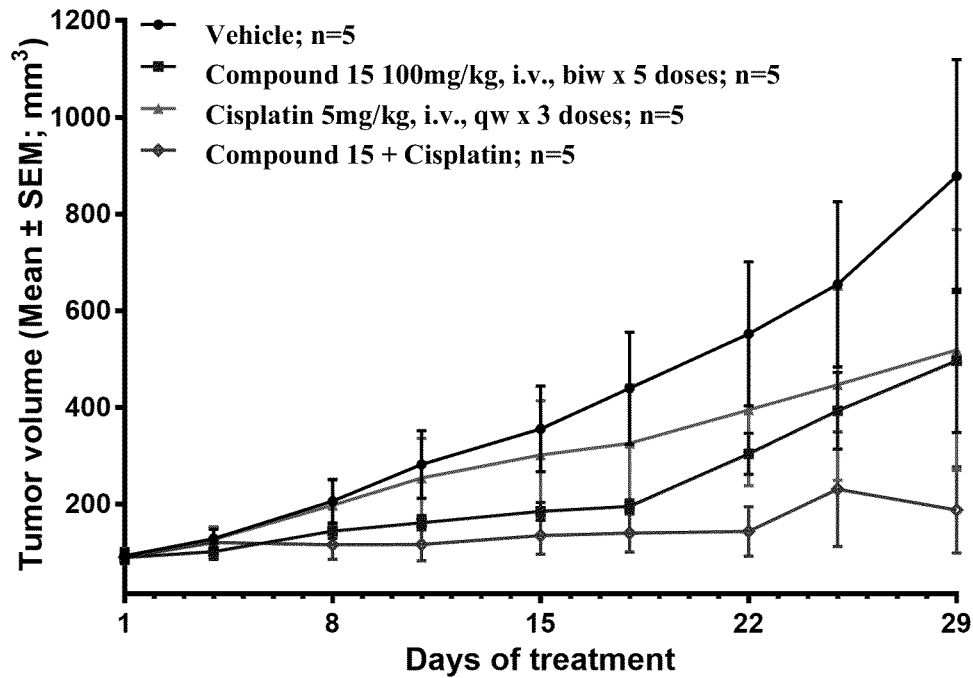
Figure 24:
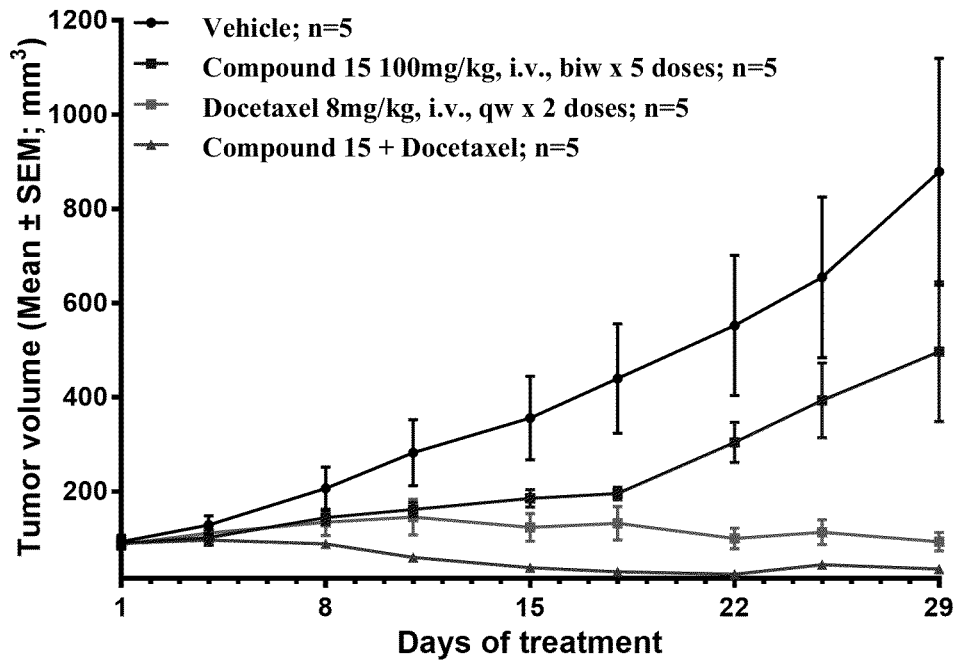

FIG. 24 shows the combination therapy of Compound 15 and cisplatin (FIG. 24(*a*)) or docetaxel (FIG. 24(*b*)) in a subcutaneous non-small cell lung cancer xenograft model of mice bearing human NCI-H1975-L858R-T790M-C797S cell line.

Figure 25:
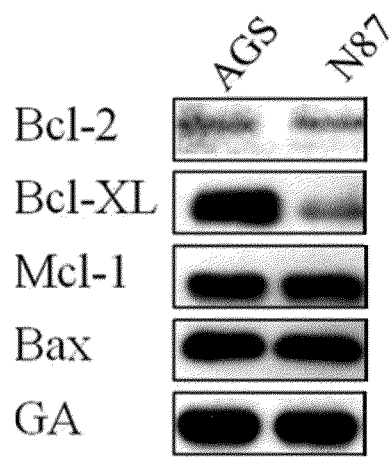

FIG. 25 shows basal expression levels of Bcl-2 family proteins in AGS and NCI-N87 gastric cancer tumor cell lines.

Figure 26A:
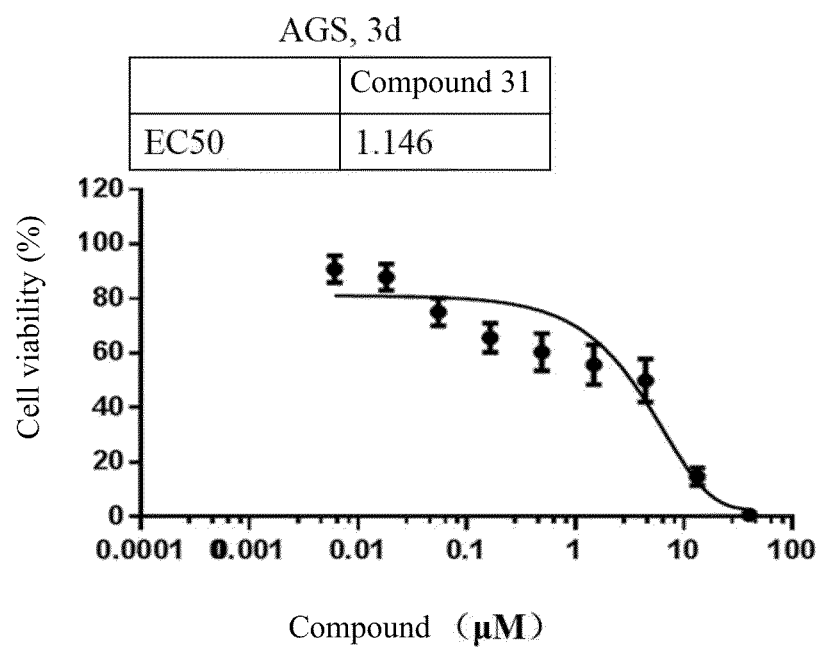
Figure 26B:
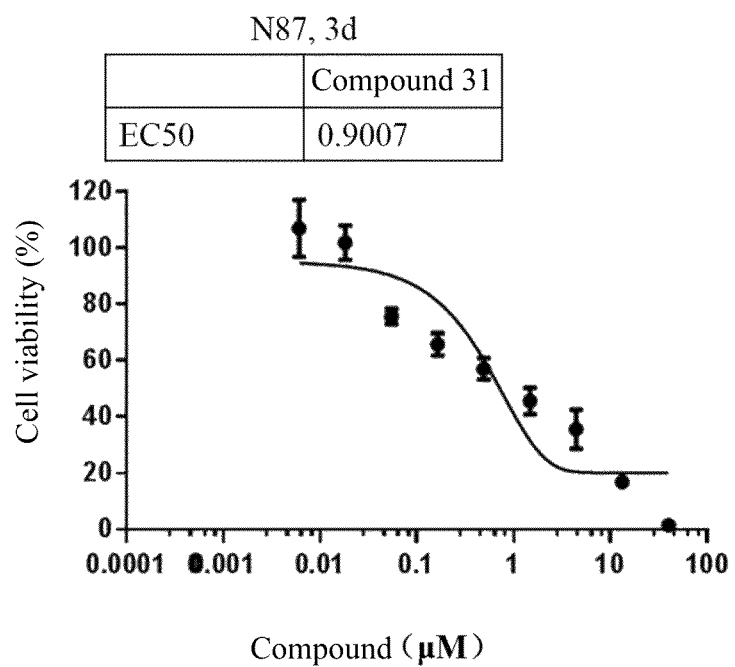

FIG. 26 shows the inhibiting effect of Compound 31 on cell proliferation in both AGS (FIG. 26 (*a*)) and NCI-N87 (FIG. 26 (*b*)) cell lines.

Figure 27:
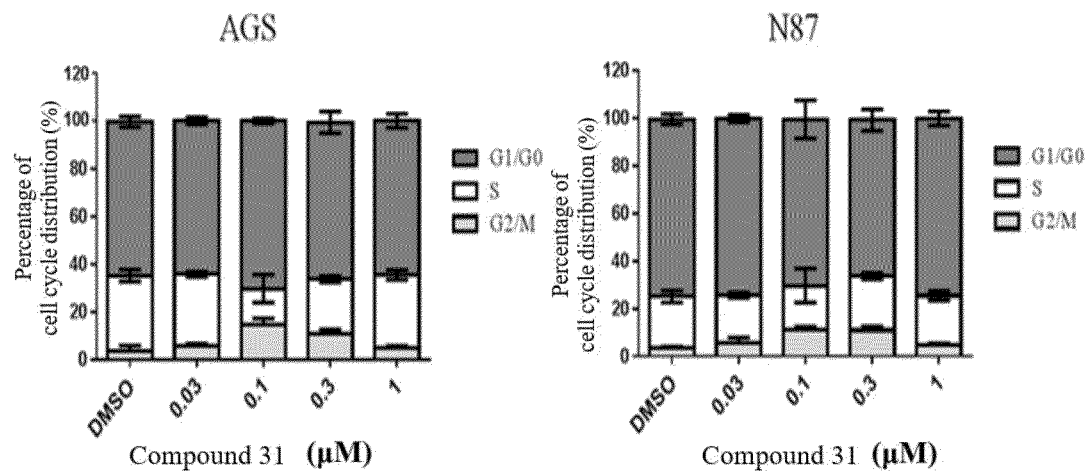

FIG. 27 shows that Compound 31 had no significant effect on cell cycle.

FIG. 28 shows the effects of Compound 15 at different concentrations on mouse xenograft tumor volume (FIG. 28(*a*)), tumor weight (FIG. 28(*b*)), tumor size (FIG. 28(*c*)), mouse body weight (FIG. 28(*d*)), apoptosis-related proteins in mouse tumor tissues (FIG. 28(*e*)) and apoptosis-related immunohistochemistry in mouse tumor tissues (FIG. 28(*f*)).

Figure 29A:
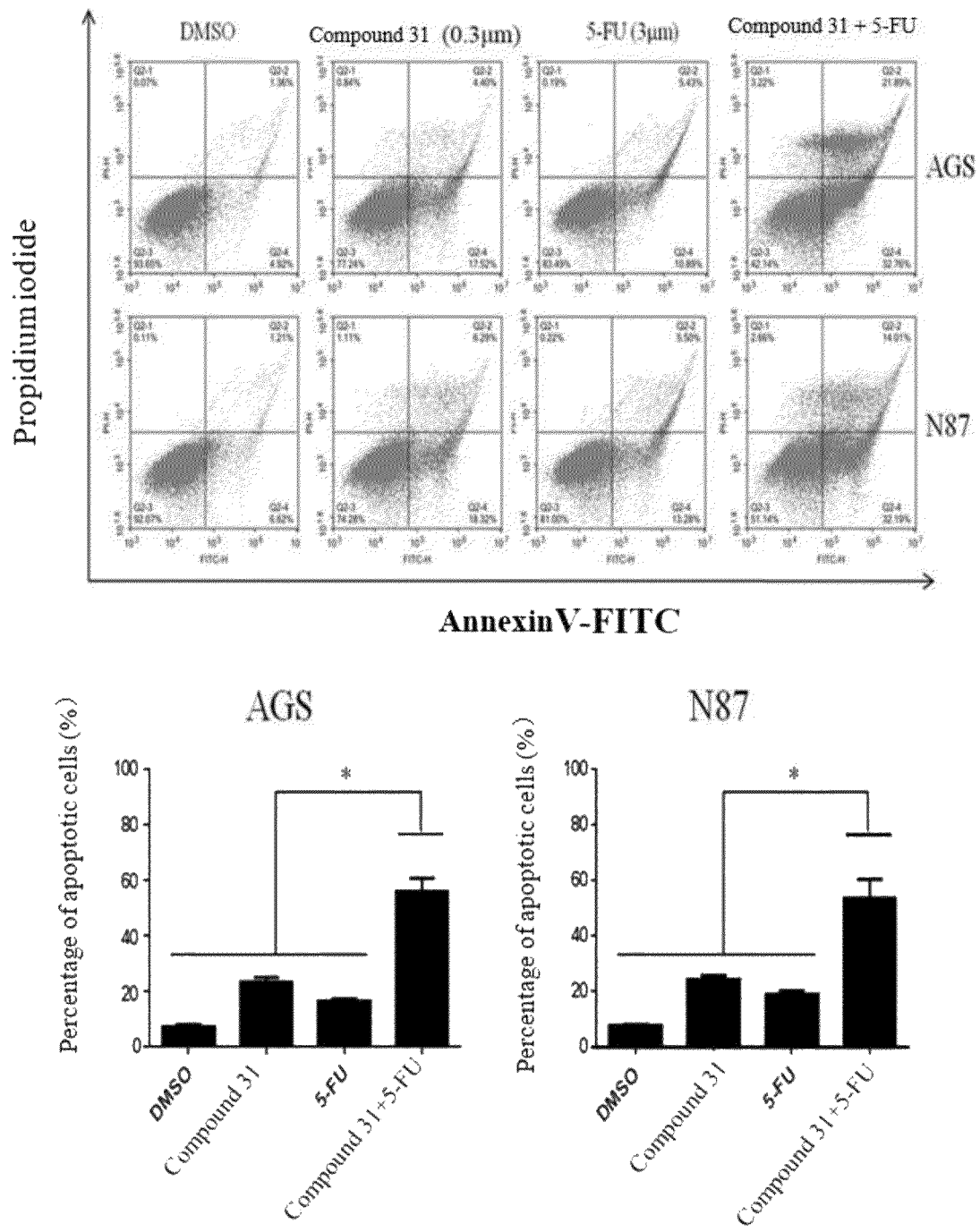
Figure 29B:
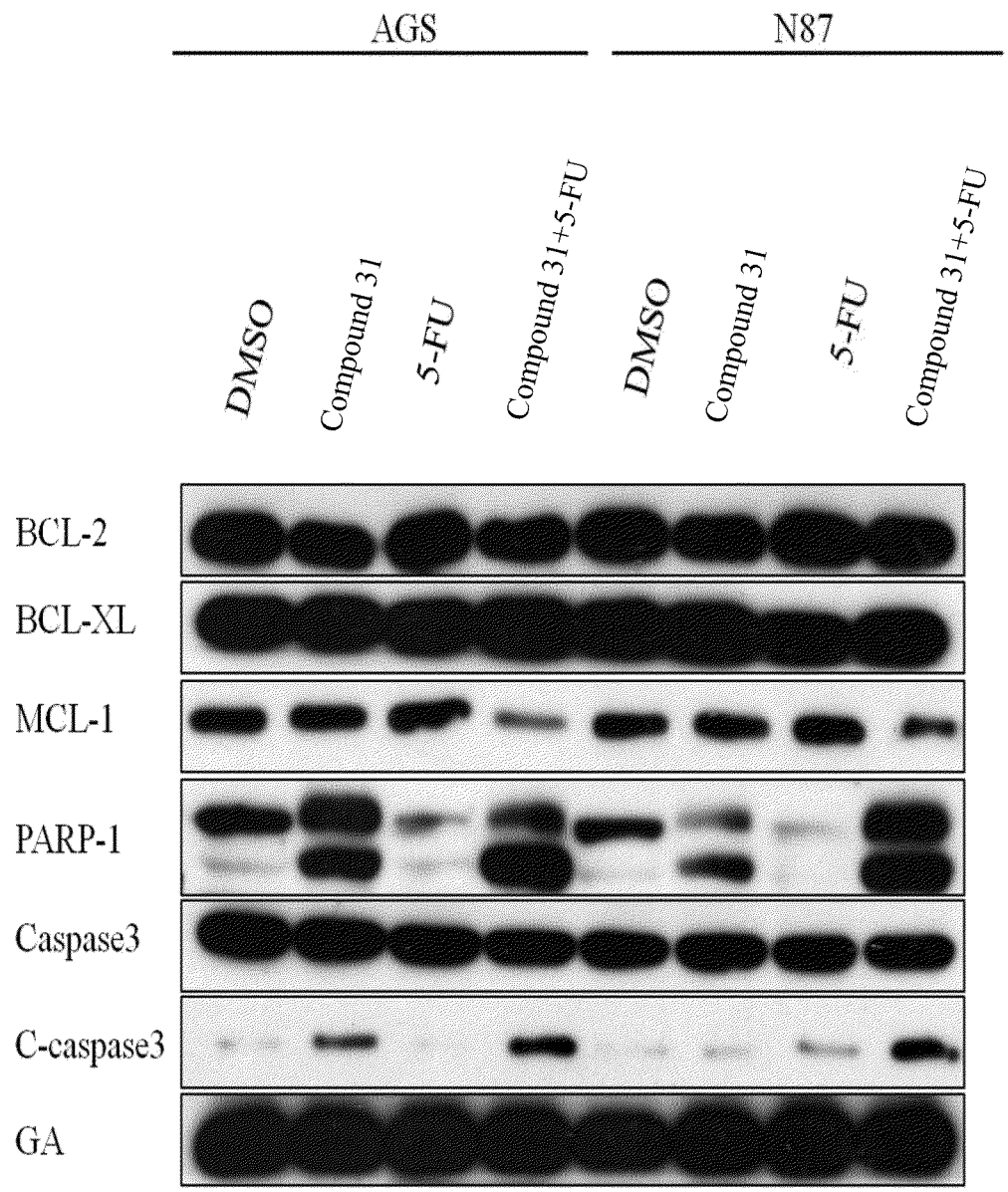

FIG. 29(*a*) shows that Compound 31 in combination with 5-fluorouracil (5-FU) induced apoptosis in gastric cancer cells; FIG. 29(*b*) shows the effect of combination therapy of Compound 31 and 5-FU on apoptosis-related proteins in gastric cancer cells.

FIG. 30 shows the effects of combination therapy of Compound 15 and 5-fluorouracil (5-FU) on mouse xenograft tumor volume (FIG. 30(*a*)), tumor weight (FIG. 30(*b*)), tumor size (FIG. 30(*c*)), body weight (FIG. 30(*d*)), TUNEL detection in mouse tumor tissues (FIG. 30(*e*)) and apoptosis-related immunohistochemistry in mouse tumor tissues (FIG. 30(*f*)).

Figure 31:
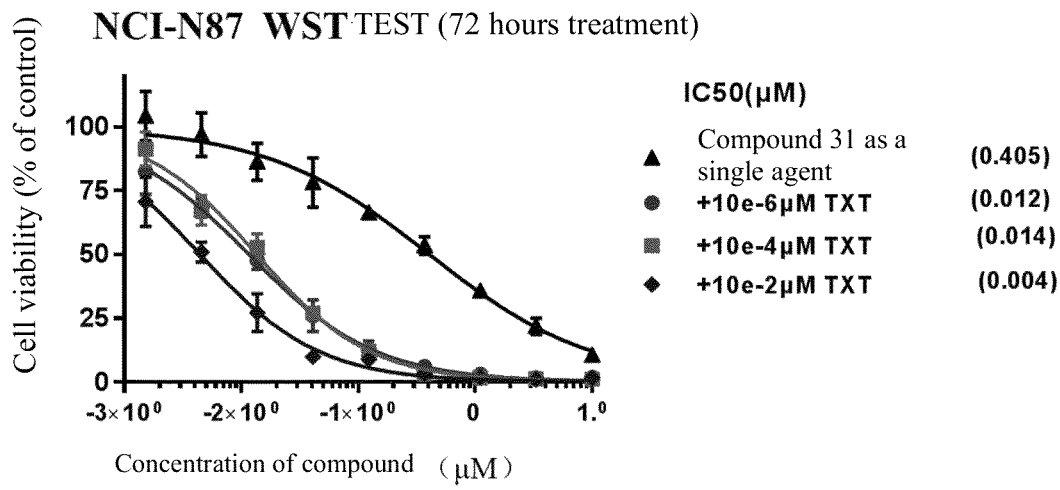

FIG. 31 shows the inhibiting effect of combination therapy of Compound 31 and docetaxel (TXT) on cell proliferation in gastric cancer xenograft model of mice bearing NCI-N87 cell line.

Figure 32:
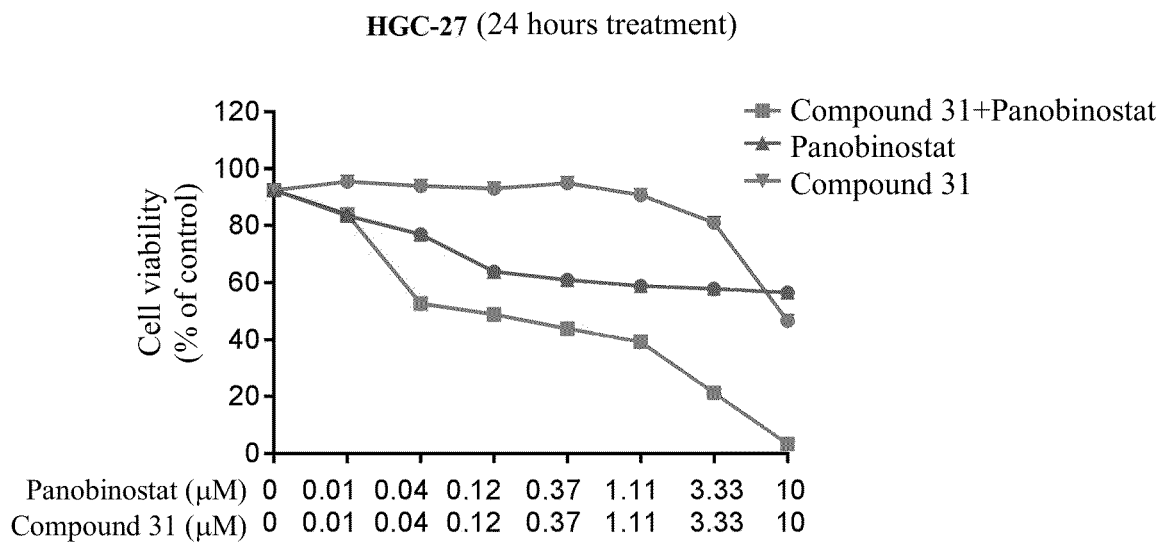

FIG. 32 shows the inhibiting effect of combination therapy of Compound 31 and panobinostat on cell proliferation in gastric cancer xenograft model of mice bearing HGC-27 cell line.

DETAILED DESCRIPTION OF THE INVENTION

The invention will now be described in connection with specific embodiments. It should be understood that the present disclosure is not limited to the following embodiments. Any changes or modifications may be made by those skilled in the art without departing from the scope of the invention, and such modifications or improvements are also included in the scope of the invention.

Pharmaceutical Composition

According to a first aspect of the present disclosure, provided herein is a pharmaceutical composition comprising a Bcl-2/Bcl-xL inhibitor and a chemotherapeutic agent, and a pharmaceutically acceptable carrier. The Bcl-2/Bcl-xL inhibitor is a compound of the following formula (I), (II), (III) or (IV), or a pharmaceutically acceptable salt thereof:

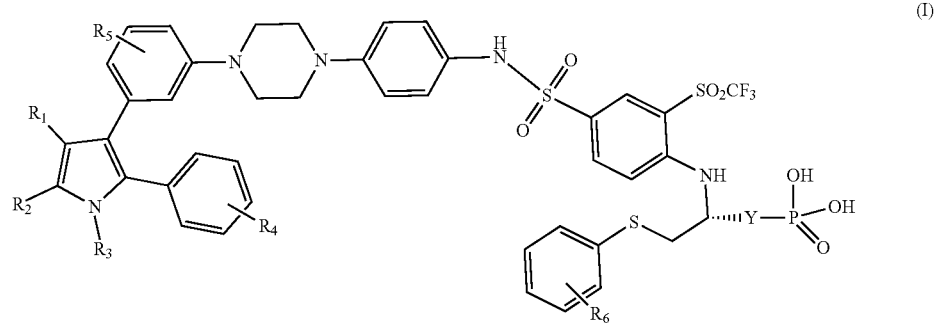

(I)

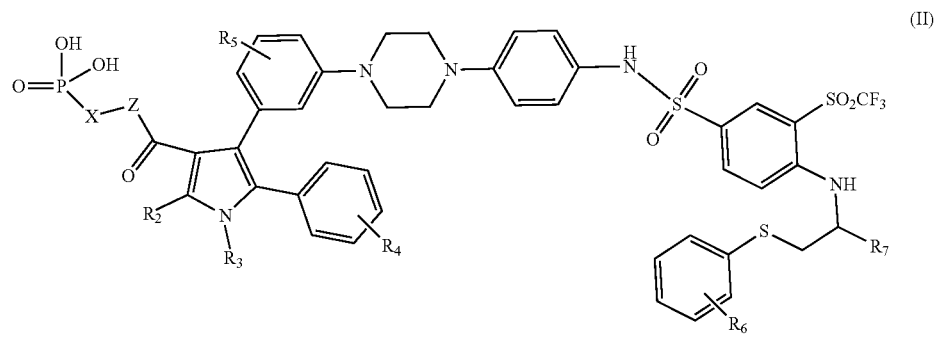

(II)

-continued

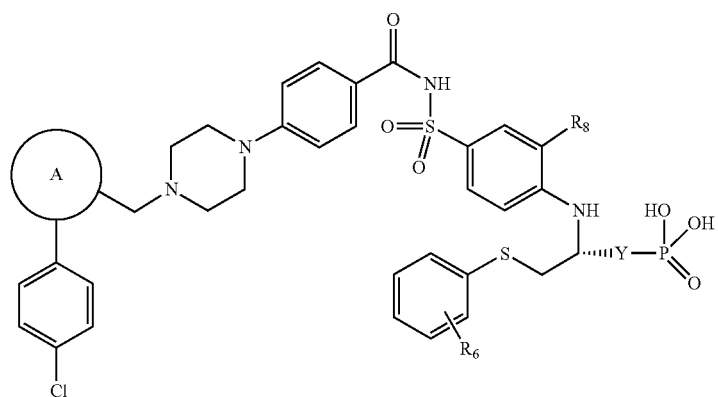
(III)

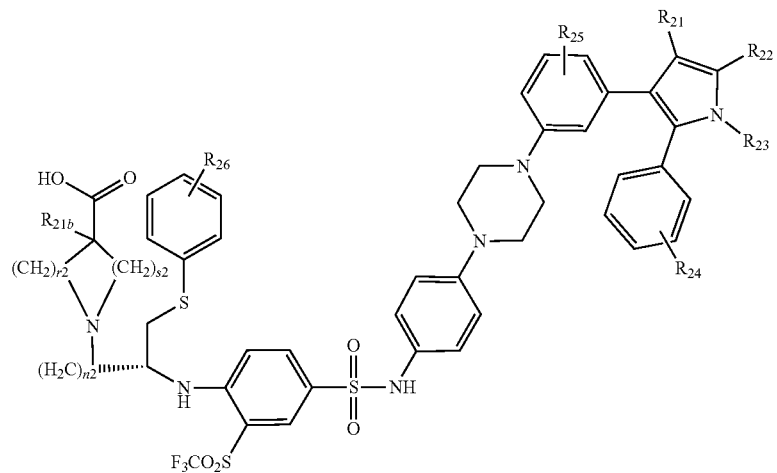
(IV)

wherein the A ring is

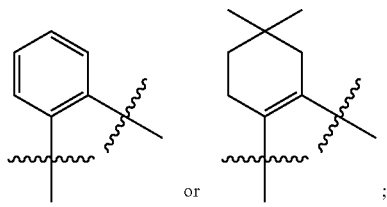
or ;

X, substituted or unsubstituted, is selected from the group consisting of alkylene, alkenylene, cycloalkylene, cycloalkenylene, and heterocycloalkylene;

Y is selected from the group consisting of $(CH_2)_n$—N$(R^a)_2$ and

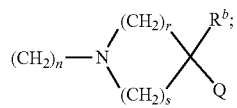

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;

Z is O or $NR^e$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'$SO_2R"$, NR'COR", NR'CONR"R"', NR'C=SNR"R"', NR'$SO_2R"$, $SO_2R'$, and $SO_2NR'R"$;

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COR', CONR'R", CONR'$SO_2R"$, $C_{1-3}$alkyleneCH(OH)$CH_2OH$, $SO_2R'$, and $SO_2NR'R"$;

R', R", and R"', independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R", or R" and R"', can be taken together with the atom to which they are bound to form a 3 to 7 membered ring;

$R_4$ is hydrogen, halo, $C_{1-3}$alkyl, $CF_3$, or CN;

$R_5$ is hydrogen, halo, $C_{1-3}$alkyl, substituted $C_{1-3}$alkyl, hydroxyalkyl, alkoxy, or substituted alkoxy;

R₆ is selected from the group consisting of H, CN, NO₂, halo, alkyl, cycloalkyl, alkenyl, cycloalkenyl, alkynyl, aryl, heteroaryl, heterocycloalkyl, OR', SR', NR'R", CO₂R', OCOR', CONR'R", CONR'SO₂R", NR'COR", NR'CONR"R", NR'C=SNR"R", NR'SO₂R", SO₂R', and SO₂NR'R";

R₇, substituted or unsubstituted, is selected form the group consisting of hydrogen, alkyl, alkenyl, (CH₂)₀₋₃cycloalkyl, (CH₂)₀₋₃cycloalkenyl, (CH₂)₀₋₃heterocycloalkyl, (CH₂)₀₋₃aryl, and (CH₂)₀₋₃heteroaryl;

R₈ is selected form the group consisting of hydrogen, halo, NO₂, CN, CF₃SO₂, and CF₃;

R_a is selected from the group consisting of hydrogen, alkyl, heteroalkyl, alkenyl, hydroxyalkyl, alkoxy, substituted alkoxy, cycloalkyl, cycloalkenyl, and heterocycloalkyl;

R_b is hydrogen or alkyl;

R_c is selected from the group consisting of hydrogen, alkyl, substituted alkyl, hydroxyalkyl, alkoxy, and substituted alkoxy;

n, r, and s, independently, are 1, 2, 3, 4, 5, or 6;

R₂₁ is SO₂R₂',

R₂₂ is alkyl, preferably C₁₋₄ alkyl, more preferably methyl, propyl, or isopropyl, R₂₃ is alkyl, preferably C₁₋₄ alkyl, more preferably methyl, propyl, or isopropyl, R₂₄ is halogen, preferably fluoride, chloride, R₂₅ is halogen, preferably fluoride, chloride, R₂₆ is selected from H, halogen, alkyl, preferably fluoride, chloride, C₁₋₄ alkyl, more preferably methyl, propyl, isopropyl R₂₁_b is H or alkyl, preferably C₁₋₄ alkyl, more preferably methyl, propyl, or isopropyl, n₂, r₂ and s₂ are independently 1, 2, 3, 4, 5 or 6, more preferably, r₂ and s₂ are both 2 and n₂ is 3, 4 or 5, more preferably, all of n₂, r₂ and s₂ are 2; and R₂' is alkyl, preferably C₁₋₄ alkyl, more preferably methyl, propyl, or isopropyl.

Bcl-2/Bcl-xL Inhibitor

As used herein, the term "Bcl-2/Bcl-xL" means Bcl-2, Bcl-xL, or Bcl-2 and Bcl-xL, i.e., Bcl-2 and/or Bcl-xL.

As used herein, the term "alkyl" refers to straight chain and branched saturated $C_{1-10}$ hydrocarbon groups, preferably $C_{1-6}$ hydrocarbon groups, non-limiting examples of which include methyl, ethyl, and straight chain and branched propyl, butyl, pentyl, hexyl, heptyl, octyl, nonyl, and decyl groups. The term $C_n$ means the alkyl group has "n" carbon atoms. The term $C_{n-p}$ means that the alkyl group contains "n" to "p" carbon atoms.

The term "alkylene" refers to an bivalent alkyl group having a general formula of —(CH₂)_n—, wherein n is an integer selected from 1-10. An alkyl, e.g., methyl, or alkylene, e.g., —CH₂— group can be unsubstituted or substituted with halo, trifluoromethyl, trifluoromethoxy, hydroxy, alkoxy, nitro, cyano, alkylamino, or amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkynyl" and "alkynylene" are defined identically as "alkyl" and "alkylene" except the group contains a carbon-carbon triple bond.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —NH₂, and the term "alkylamino" is defined as —NR₂, wherein at least one R is alkyl and the second R is alkyl or hydrogen.

The term "nitro" is defined as —NO₂.

The term "cyano" is defined as —CN.

The term "trifluoromethyl" is defined as —CF₃.

The term "trifluoromethoxy" is defined as —OCF₃.

As used herein, groups such as

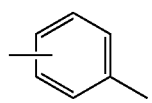

is an abbreviation for

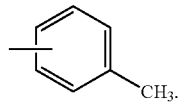

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —OCF₃, —CF₃, —NO₂, —CN, —NC, —OH, alkoxy, amino, alkylamino, —CO₂H, —CO₂alkyl, —OCOalkyl, aryl, and heteroaryl.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF₃, —CF₃, —NO₂, —CN, —NC, —OH, alkoxy, amino, alkylamino, —CO₂H, —CO₂alkyl, —OCOalkyl, aryl, and heteroaryl.

As used herein, the term "cycloalkyl" means a monocyclic aliphatic ring containing 3-8 carbon atoms. The term "heterocycloalkyl" means a monocyclic or bicyclic ring system containing at least one nitrogen, oxygen, or sulfur atom in the ring system. The terms "heteroaryl" and "heterocycloalkyl" encompass ring systems containing at least one oxygen atom, nitrogen atom, or sulfur atom, and includes ring systems containing oxygen and nitrogen atoms, oxygen and sulfur atoms, nitrogen and sulfur atoms, and nitrogen, oxygen, and sulfur atoms.

In the above formula (I), (II) or (III), in some embodiments, R₁ and R₂ or R₂ and R₃ may together form a ring. In other embodiments, R' and R" or R" and R"" may form a 3-7 membered ring with the atoms to which they are attached.

In some preferred embodiments, X is alkylene, and in preferred embodiments, is $C_{1-3}$ alkylene.

In some embodiments, Y is

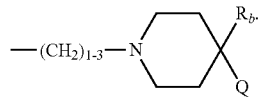

In preferred embodiments, n is 2. In other preferred embodiments, $R_b$ is hydrogen or $C_{1-3}$ alkyl.

In still other preferred embodiments, Q is O, $O(CH_2)_{1-3}$, $C(=O)O(CH_2)_{1-3}$, $OC(=O)(CH_2)_{1-3}$, or $C(=O)O(C_3H_7)_{1-3}$. In some embodiments, Q is O, $OCH_2$, $C(=O)OCH_2$, $C(=O)O(CH_2)_2$, $C(=O)O(CH_2)_3$, $OC(=O)CH_2$ or $C(=O)O(CH(CH_3)CH_2)$.

In some embodiments, Z is O, NH, or $N(C_{1-3}alkyl)$. In preferred embodiments, Z is O, NH, or $NCH_3$.

In some embodiments, $R_1$ is $SO_2R'$, $SO_2NR'R''$, $NR'SOR''$, H, or alkyl. In some preferred embodiments, $R_1$ is $SO_2(C_{1-3}alkyl)$, $SO_2N(C_{1-3}alkyl)_2$, $NHSO_2(C_{1-3}alkyl)$, H, or $C_{1-3}alkyl$. One preferred embodiment of $R_1$ is $SO_2CH_3$.

In some embodiments, $R_2$ and $R_3$, independently, are H, $C_{1-3}alkyl$, or cycloalkyl. $R_2$ also can be halo. In some preferred embodiments, $R_2$ and $R_3$, independently, are methyl, ethyl, n-propyl, isopropyl, cyclopentyl, or cyclohexyl. $R_2$ also can be Cl or F.

In some embodiments, $R_4$ is H or halo, preferably H, Cl, or F. In other embodiments, $R_5$ is H, halo or $C_{1-3}alkyl$, preferrably H, methyl, ethyl, n-propyl, isopropyl, F, or Cl. In other embodiments, $R_6$ is H, halo, alkyl, or cycloalkyl. In some preferred embodiments, $R_6$ is H, F, Cl, $C_{1-3}alkyl$, cyclopentyl, or cyclohexyl.

In some embodiments, $R_7$ is $(CH_2)_{0-3}cycloalkyl$ or $(CH_2)_{0-3}heterocycloalkyl$. In a preferred embodiment, $R_7$ is $(CH_2)_{0-3}cycloalkyl$, optionally substituted with —OH. In one embodiment, $R_7$ is

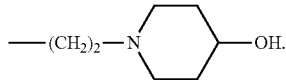

In some embodiments, $R_8$ is $CF_3SO_2$ or $CF_3$. In various embodiments, $R_a$, $R_b$, and $R_c$, independently, are H or $C_{1-3}alkyl$.

Additionally, salts, hydrates, solvates and active metabolites of the present compounds of formula (I), (II), (III) or (IV) also are included in the present disclosure and can be used in the methods disclosed herein. The present disclosure further includes all possible stereoisomers and geometric isomers of the compounds of structural formula (I), (II), (III) or (IV). The present disclosure includes both racemic compounds and optically active isomers. When a compound of structural formula (I), (II), (III) or (IV) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of the compounds of structural formula (I), (II), (III) or (IV) are possible, the present disclosure is intended to include all tautomeric forms of the compounds.

As used herein, the term "pharmaceutically acceptable salts" refers to salts or zwitterionic forms of the compounds of structural formula (I), (II), (III) or (IV). Salts of compounds of formula (I), (II), (III) or (IV) can be prepared during the final isolation and purification of the compounds or separately by reacting the compound with an acid having a suitable cation. The pharmaceutically acceptable salts of compounds of structural formula (I), (II), (III) or (IV) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

In accordance with the foregoing, any reference to a compound of the invention presented herein is intended to include a compound of formula (I), (II), (III) or (IV), and pharmaceutically acceptable salts, hydrates, solvates or active metabolite thereof. The term "active metabolite" as used herein refers to a metabolite of a compound of formula (I), (II), (III) or (IV) in the human body.

Specific compounds of the present disclosure include, but are not limited to, compounds having the structure formulae set forth below in Table 1.

TABLE 1
| Compound # | Formula |
| --- | --- |
| 1 | 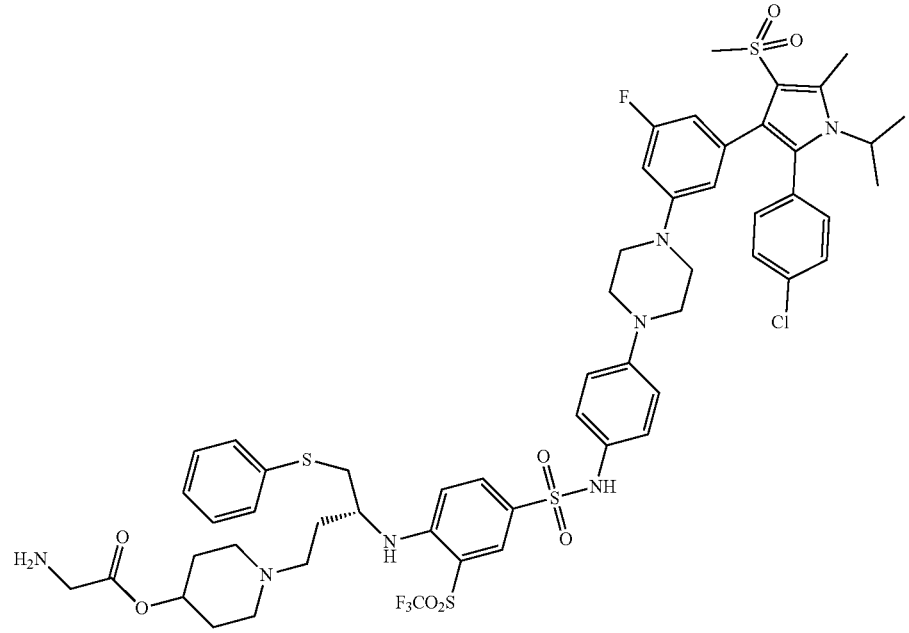 |
| 2 | 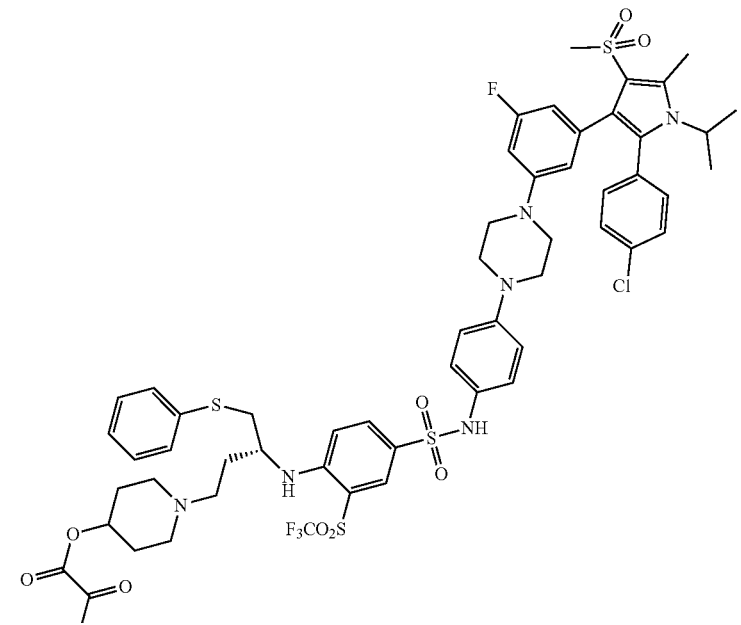 |

TABLE 1-continued
| Compound # | Formula |
|---|---|
| 3 | 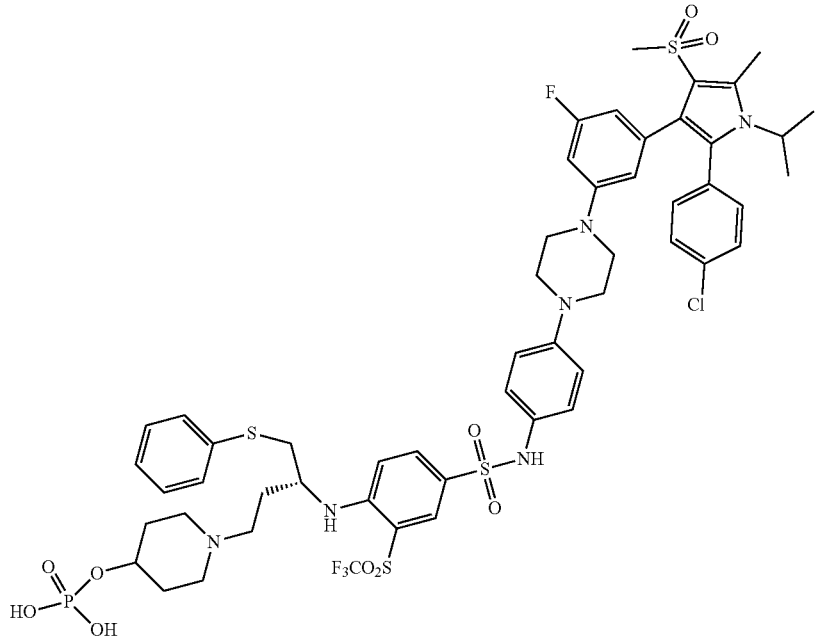 |
| 4 | 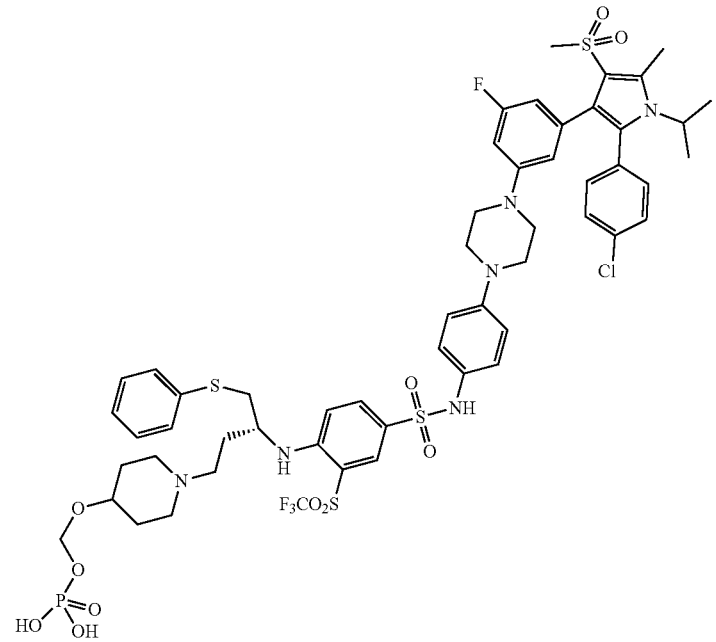 |

TABLE 1-continued
| Compound # | Formula |
|---|---|
| 5 | 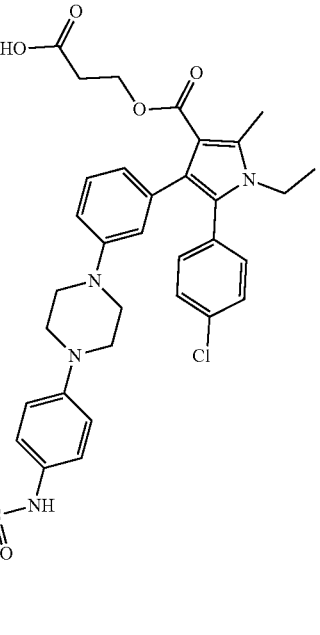 |
| 6 | 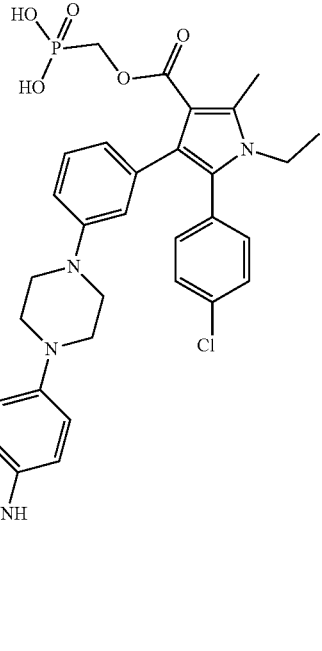 |

TABLE 1-continued
| Compound # | Formula |
|---|---|
| 7 | 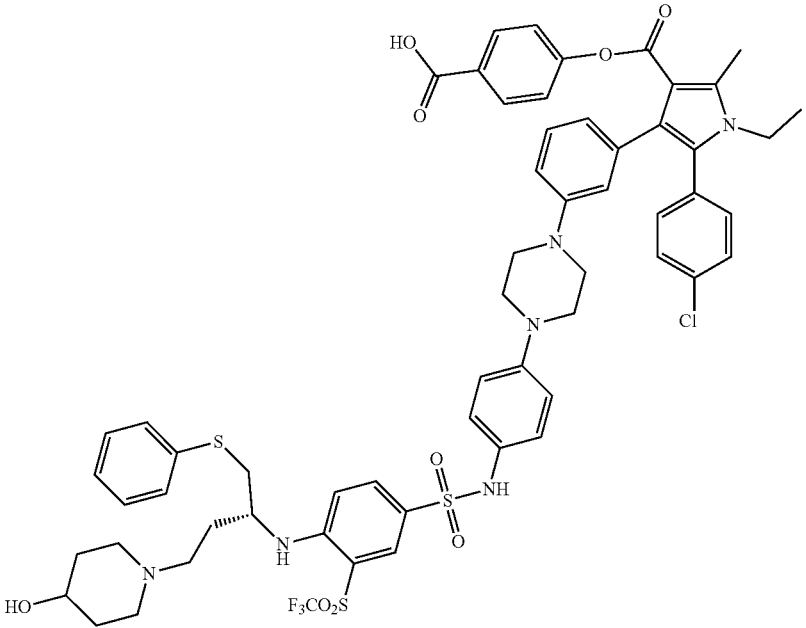 |
| 8 | 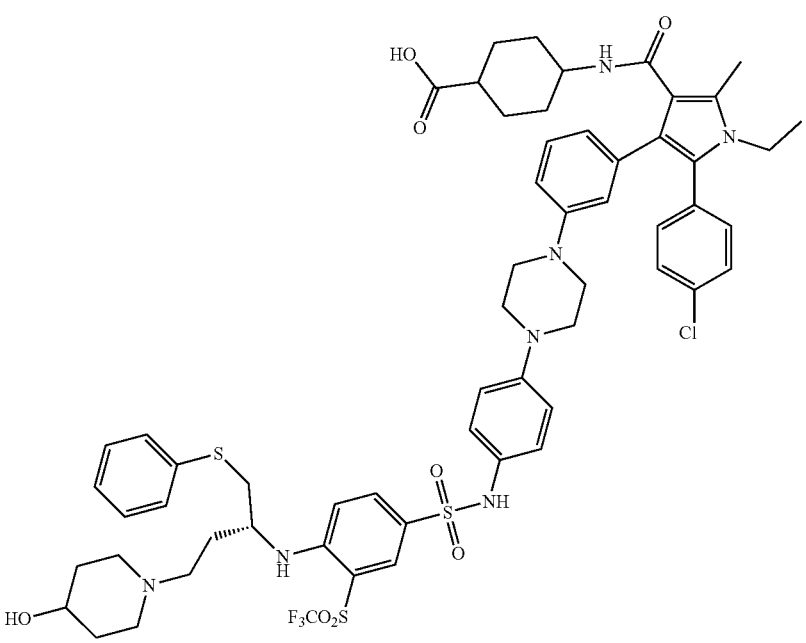 |

TABLE 1-continued
| Compound # | Formula |
| --- | --- |
| 9 | 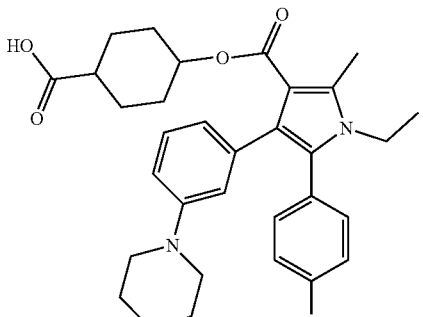 |
| 10 | 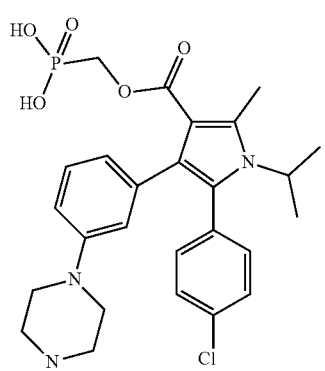 |

TABLE 1-continued
| Compound # | Formula |
|---|---|
| 11 | 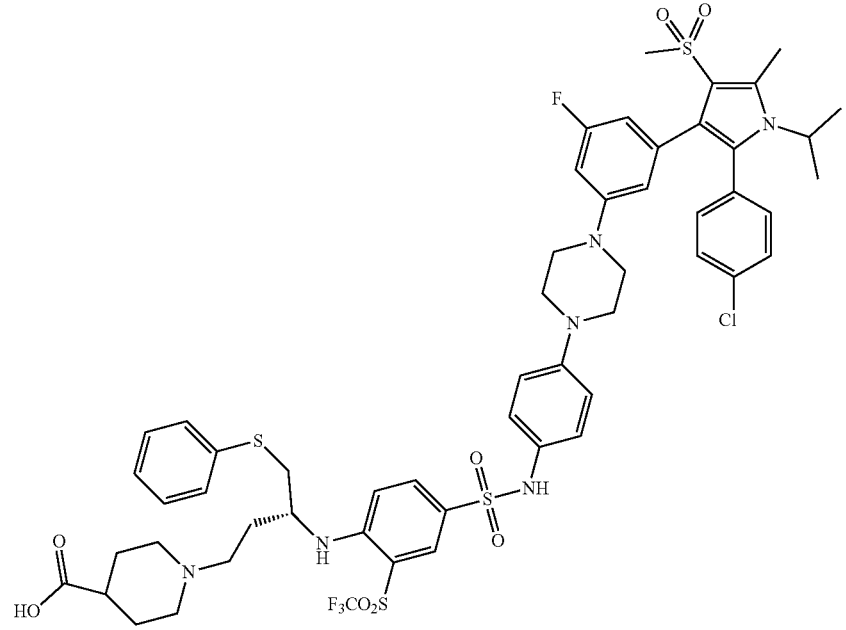 |
| 12 | 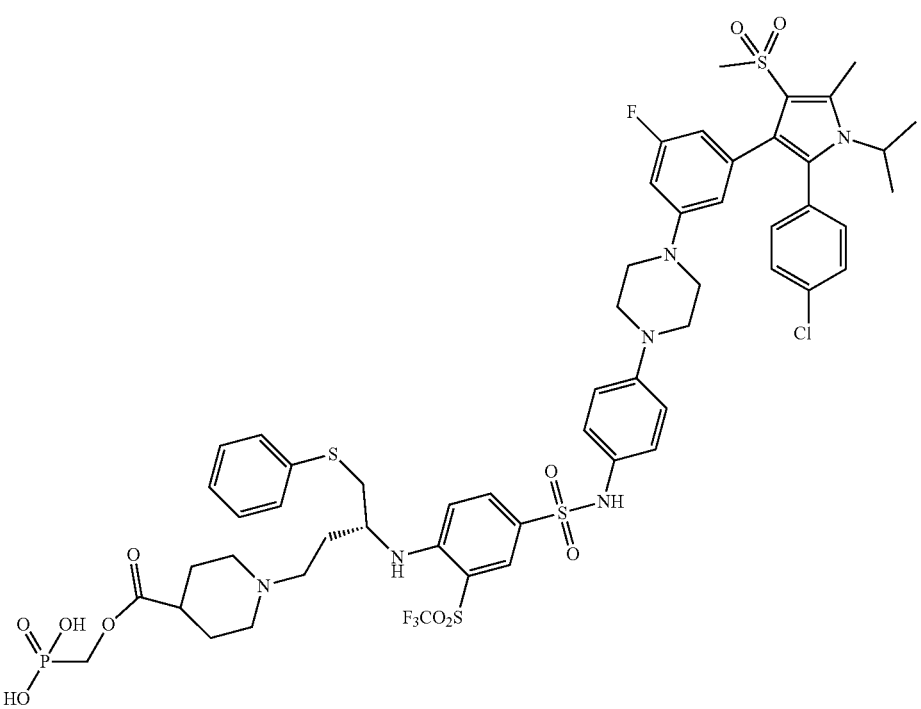 |

TABLE 1-continued
| Compound # | Formula |
|---|---|
| 13 | 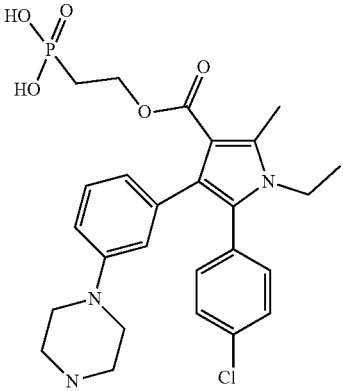 |
| 14 | 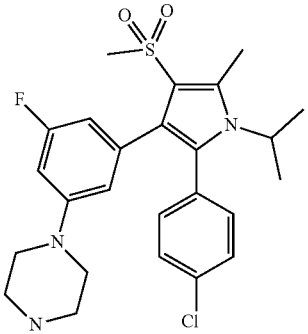 |

TABLE 1-continued
| Compound # | Formula |
| --- | --- |
| 15 | 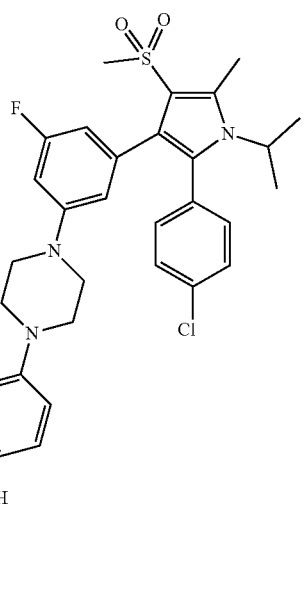 |
| 16 | 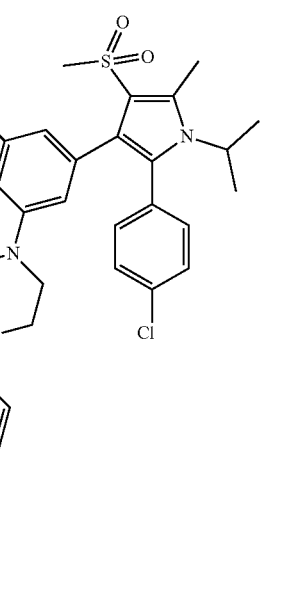 |

TABLE 1-continued

| Compound # | Formula |
| --- | --- |
| 17 | |
| 18 | |

TABLE 1-continued
| Compound # | Formula |
|---|---|
| 19 | 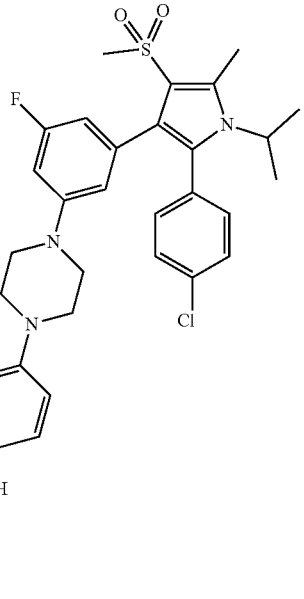 |
| 20 | 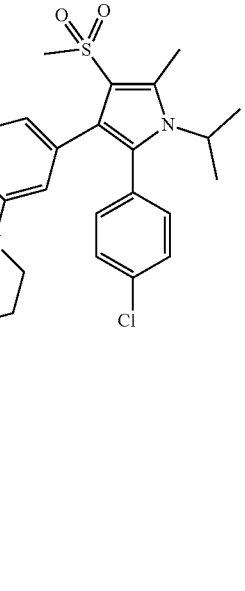 |

TABLE 1-continued
| Compound # | Formula |
| --- | --- |
| 21 | 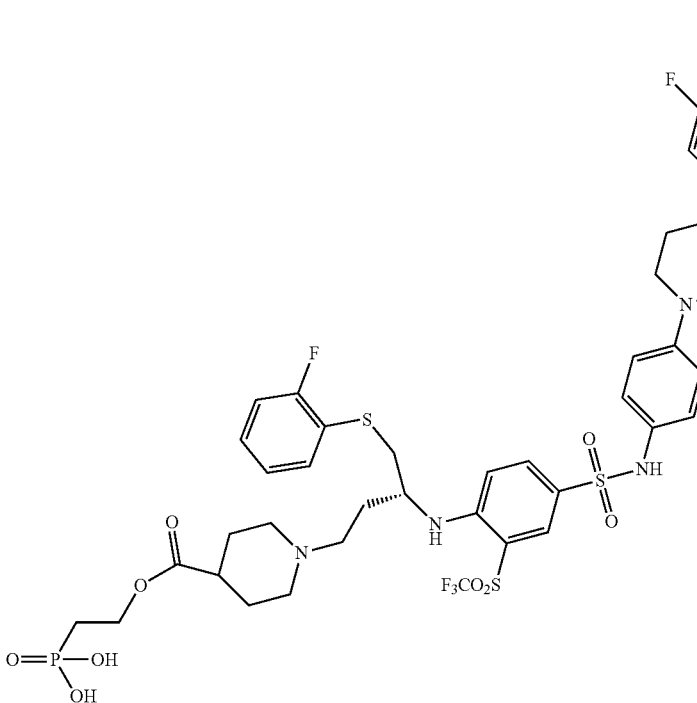 |
| 22 | 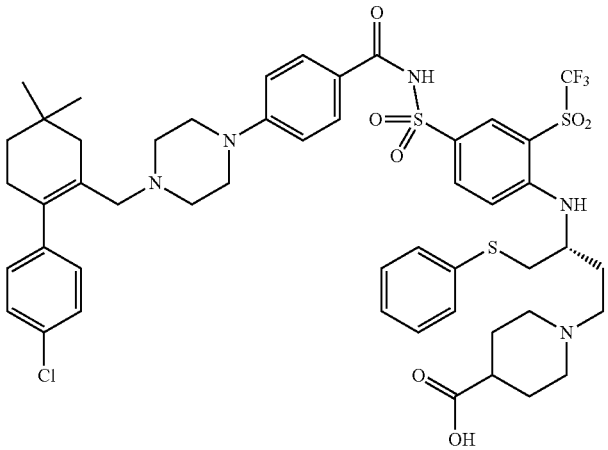 [SMILES: CC1(C)CCC(c2ccc(Cl)cc2)=C(CN2CCN(c3ccc(C(=O)NS(=O)(=O)c4ccc(N[C@H](CCN5CCC(C(=O)O)CC5)CSc5ccccc5)c(S(=O)(=O)C(F)(F)F)c4)cc3)CC2)C1] |

TABLE 1-continued

| Compound # | Formula |
| --- | --- |
| 23 | |
| 24 | |
| 25 | |

TABLE 1-continued
| Compound # | Formula |
| --- | --- |
| 26 | 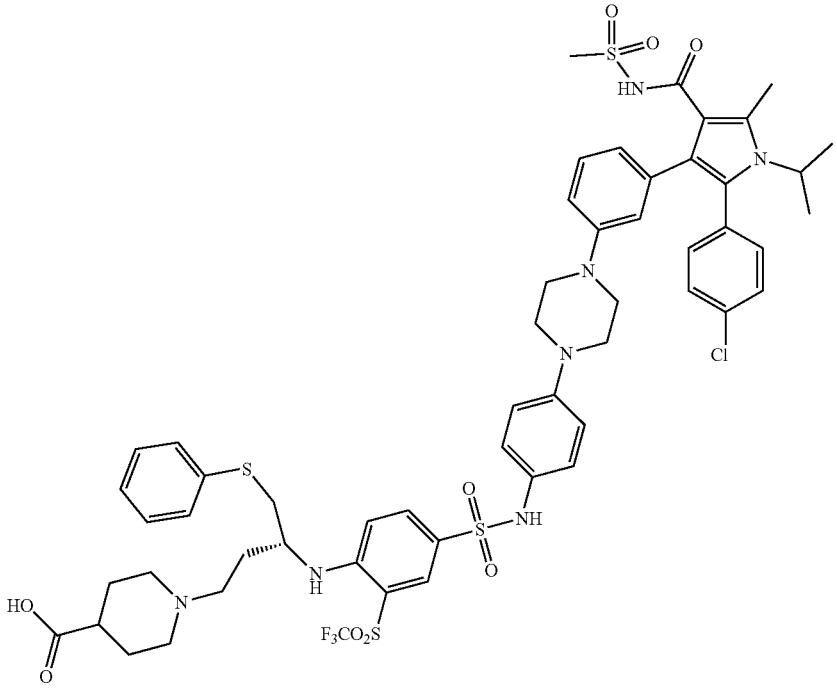 |
| 27 | 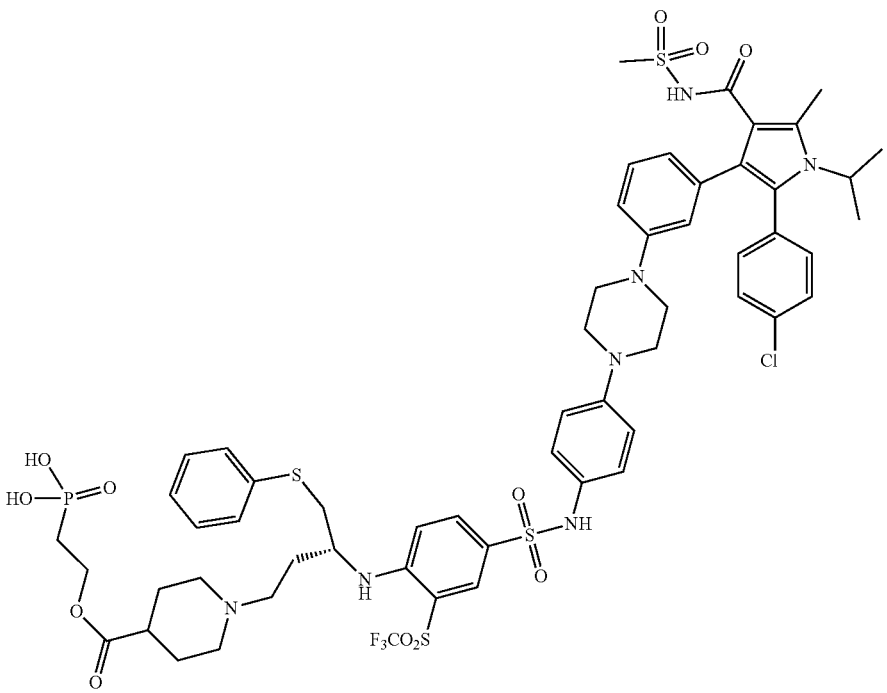 |

TABLE 1-continued
| Compound # | Formula |
|---|---|
| 28 | 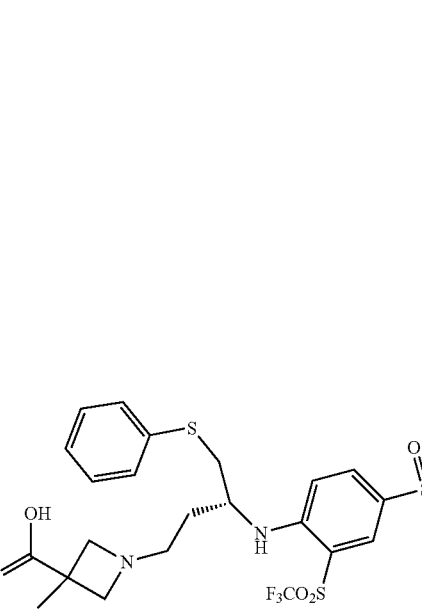 |
| 29 | 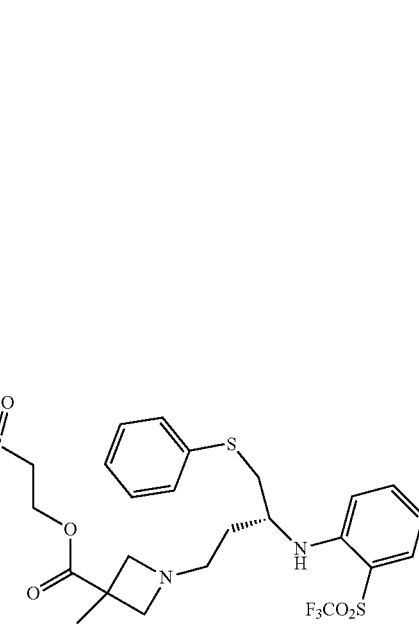 |

TABLE 1-continued
| Compound # | Formula |
|---|---|
| 30 | 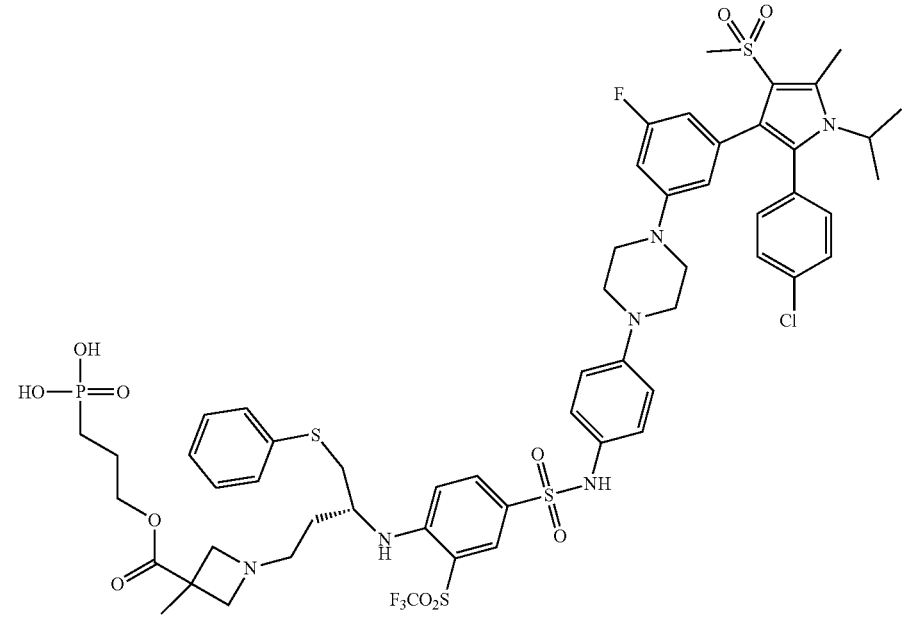 |
| 31 | 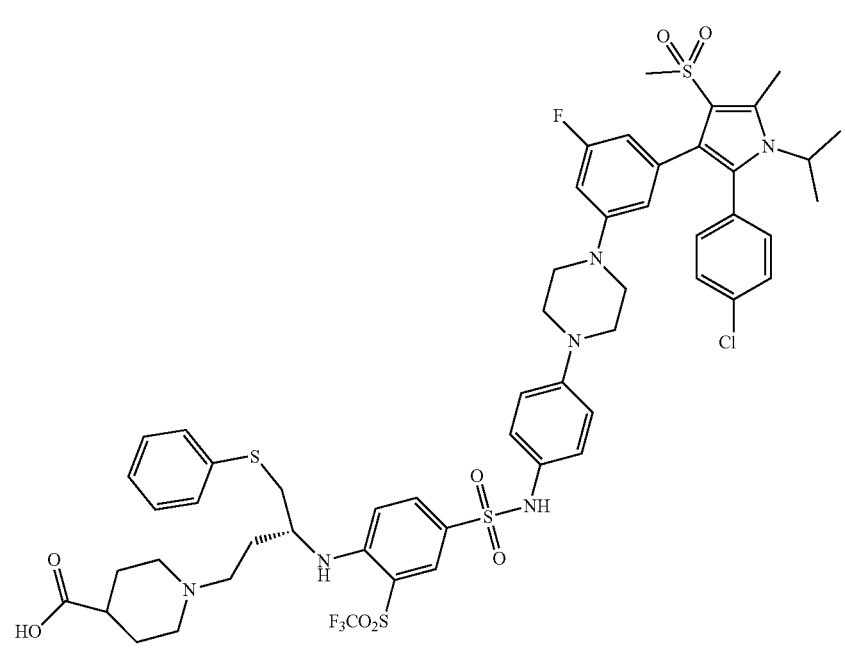 |

TABLE 1-continued
| Compound # | Formula |
|---|---|
| 32 | 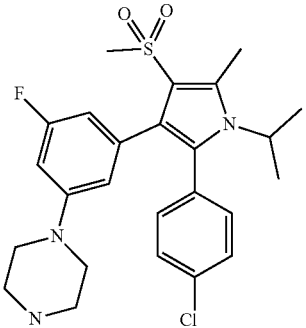 |
| 33 | 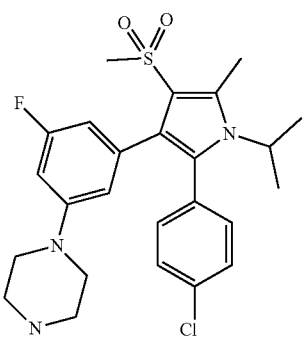 |

TABLE 1-continued

| Compound # | Formula |
|---|---|
| 34 | |
| 35 | |

The Bcl-2/Bcl-xL inhibitor of the present disclosure is preferably (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy)ethylphosphonic acid (i.e., compound 15, in the above table, sometimes abbreviated as "compound 15") or a pharmaceutically acceptable salt thereof, as represented by the following structural formula:

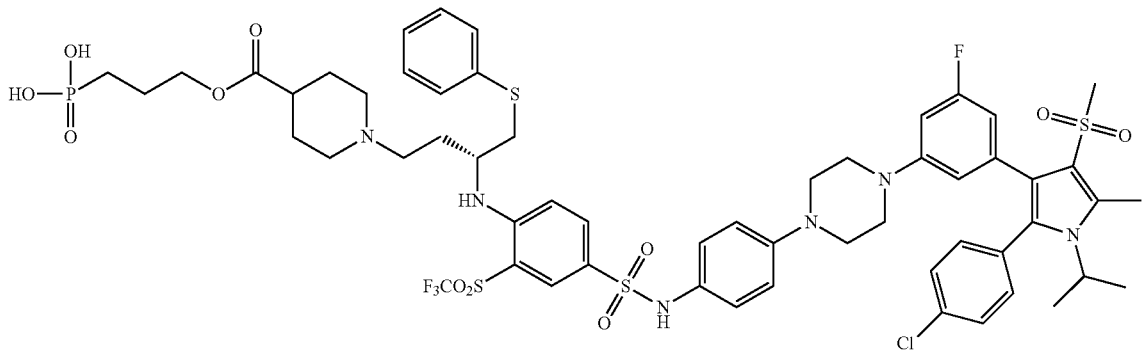

Compound 15 selectively binds to Bcl-2, Bcl-xl, and Bcl-w proteins with high affinity, and has an IC50 of 1.6 nM, 4.4 nM, and 9.3 nM, respectively. Compound 15 binds weakly to Mcl-1. Having chemical structural modification, Compound 15 effectively reduces the platelet toxicity defects of the first-generation BCL-2 inhibitors in the blood circulation, and is capable of inducing specific enzyme activation in tissues to effectively kill tumor cells. Its platelet toxicity is reduced by 10-30 times, but the activity is about 10 times that of the first generation BCL-2 inhibitor. Compound 31 is an active metabolite of Compound 15. Compound 15 is a novel second generation protein inhibitor targeting BCL-2.

The Bcl-2/Bcl-xL inhibitor of the present disclosure may also preferably be (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl) piperazin-1-yl)phenyl)sulfamoyl)-2-(trifluoromethylsulfonyl)phenylamino)-4-(phenylthio) butyl)piperidine-4-carboxylic acid (i.e., compound 31 in the above table, sometimes abbreviated as "compound 31") or a pharmaceutically acceptable salt thereof, as represented by the following structural formula:

The above Bcl-2/Bcl-xL inhibitor of the pharmaceutical composition of the present disclosure can be synthesized according to the method described in WO2014/113413A1.

Chemotherapeutic Agent

The term "chemotherapeutic drug" is a biological (macromolecule) or chemical (small molecule) compound that can be used to treat cancer. The types of chemotherapeutic drugs include, but are not limited to, histone deacetylase inhibitor (HDACI), alkylating agents, antimetabolites, alkaloids, cytotoxic/anti-cancer antibiotics, topoisomerase inhibitors, tubulin inhibitors, proteins, antibodies, kinase inhibitors, and the like. Chemotherapeutic drugs include compounds for targeted therapy and non-targeted compounds of conventional chemotherapy.

Non-limiting examples of chemotherapeutic drugs include: erlotinib, afatinib, docetaxel, adriamycin, 5-FU (5-fluorouracil), panobinostat, gemcitabine, cisplatin, carboplatin, paclitaxel, bevacizumab, trastuzumab, pertuzumab, metformin, temozolomide, tamoxifen, doxorubicin, rapamycin, lapatinib, hydroxycamptothecin, trimetinib. Further examples of chemotherapeutic drugs include: oxaliplatin, bortezomib, sunitinib, letrozole, imatinib, PI3K inhibitor, fulvestrant, leucovorin, lonafarnib, sorafenib, gefitinib,

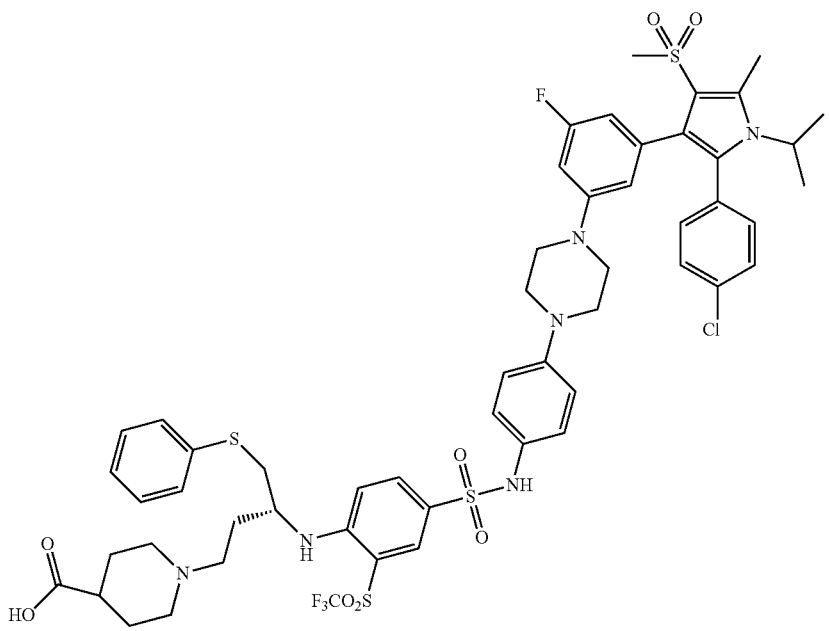

crizotinib, irinotecan, topotecan, valrubicin, vemurafenib, telbivinib, capecitabine, vandetanib, chloranmbucil, panitumumab, cetuximab, rituximab, tositumomab, temsirolimus, everolimus, pazopanib, canfosfamide, thiotepa, cyclophosphamide; alkyl sulfonates e.g., busulfan, improsulfan and piposulfan; ethyleneimine, benzodopa, carboquone, meturedopa, uredopa, methylmelamine, including altretamine, triethylenemelamine, triethyl phosphamide, triethyl thiophosphamide and trimethylenemelamine; bullatacin, bullatacinone; bryostatin; callystatin, CC-1065 (including its adozelesin, carzelesin, bizelesin synthetic analogue), cryptophycin (in particular, cryptophycin 1 and cryptophycin 8); dolastatin, duocarmycin (including synthetic analogue KW-2189 and CB1-TM1); eleutherobin; pancratistatin, sarcodictyin, spongistatin; nitrogen mustards, e.g., chlorambucil, chlornaphazine, cyclophosphamide, estramustine, ifosfamide, bis-chloroethyl-methylamine, Mechlorethaminoxide(, melphalan, novembichin, phenesterine, prednimustine, trofosfamide, uramustine, nitrosourea, e.g., carmustine, chlorozotocin, fotemustine, lomustine, nimustine, ranimnustine, antibiotics, e.g., enediyne antibiotics (e.g., calicheamicin, calicheamicin γ1I, calicheamicin ωI1, dynemicin, dynemicin A; diphosphate, e.g, clodronate, esperamicin, and neocarzinostatin chromophore and related chromoprotein enediyne antibiotics chromophore), aclacinomycin, actinomycin, all-trans retinoic acid, anthramycin, azaserine, bleomycin, actinomycin C, carabicin, carminomycin, carzinophilin, chromomycinis, actinomycin D, daunorubicin, deoxy-fluorouridine, detorubicin, 6-dizao-5-oxo-L-norleucine, morpholino-doxorubicin, cyno-morpholino-doxorubicin, 2-pyrroline-doxorubicin, eoxy doxorubicin, epirubicin, esorubicin, idarubicin, marcellomycin, mitomycin, mycophenolic acid, nogalamycin, olivomycin, peplomycin, porfiromycin, puromycin, quelamycin, rodorubicin, streptonigrin, streptozocin, tubercidin, ubenimex, zinostatin, zorubicin; antimetabolite, e.g., methotrexate; folate analogue, e.g., dimethylfolate, methotrexate, pteropterin, trimetrexate, purine analogue, e.g., fludarabine, 6-mercaptopurine, methotrexate, thiamiprine, tioguanine; pyrimidine analogue, e.g., ancitabine, azacitidine, azathioprine, bleomycin, 6-nitrouridine, carmofur, cytarabine, dideoxyuridine, doxifluridine, enocitabine, floxuridine; androgen, calusterone, dromostanolone propionate, epitiostanol, mepitiostane, testolactone; antiadrenergic agent, e.g. aminoglutethimide, mitotane, trilostane; folate supplement, e.g. folinate; aceglatone; aldophosphamide glycoside; aminolevulinic acid; eniluracil, amsacrine, bestrabucil, bisantrene, edatraxate, defofamine, demecolcine, diaziquone, elfornithine, elliptinium acetate, epothilone, etoglucid; gallium nitrate; hydroxycarbamide; lentinan, lonidainine, maytansinoid, maytansine, ansamitocin, mitoguazone, mitoxantrone, mopidamol, nitraerine, pentostatin, phenamet, pirarubicin, losoxantrone, podophyllinic acid; 2-ethylhydrazine; procarbazine, PSK® polysaccharide complex (JHS Natural Products, Eugene, OR), razoxane, rhizoxin, sizofiran, spirogermanium, tenuazonic acid, triaziquone; 2,2',2"-trichloro-triethylamine; trichothecene(in particular, T-2toxin, verracurin A, roridin A and anguidine); urethane, vindesine, dacarbazine, mannomustine; dibromomannitol; dibromodulcitol; pipobroman, gacytosine, arabinoside ("Ara-C"); cyclophosphamide; thiotepa; tioguanine; 6-mercaptopurine; methotrexate; Vinblastine; etoposide, ifosfamide, mitoxantrone, vincristine, vinorelbine, novantrone; emetrexed, teniposide, edatrexate, daunomycin; aminopterin; ibandronate; CPT-11; topoisomerase inhibitor RFS 2000; DMFO, retinoid, e.g., Retinoic acid; and a pharmaceutically acceptable salt or derivative thereof.

The chemotherapeutic drug used herein is preferably actinomycin, all-trans retinoic acid, azacitidine, azathioprine, bleomycin, bortezomib, carboplatin, capecitabine, cisplatin, chlorambucil, cyclophosphamide, cytosine arabinoside, daunorubicin, docetaxel, deoxyfluorouridine, doxorubicin, epirubicin, epothilone, etoposide, fluorouracil (e.g. 5-fluorouracil), panobinstat, gemcitabine, hydroxyurea, idarubicin, imatinib, irinotecan, nitrogen mustard, Mercaptopurine, methotrexate, mitoxantrone, oxaliplatin, paclitaxel, pemetrexed, teniposide, thioguanine, topotecan, valrubicin, vemurafenib, vinblastine, vincristine, vindesine, vinorelbine or hydroxycamptothecin, more preferably docetaxel, cisplatin, irinotecan, doxorubicin, docetaxel, cisplatin, gemcitabine, irinotecan or hydroxycamptothecin, even more preferably docetaxel, fluorouracil (e.g. 5-fluorouracil), panobinstat, cisplatin, irinotecan, paclitaxel, topotecan, or etoposide, most preferably is docetaxel, fluorouracil (e.g. 5-fluorouracil), or panobinstat.

Treatment of Cancer

The pharmaceutical composition described herein can be used for the treatment of cancer, which include but not limited to adrenal cancer, lymphoepithelial neoplasia, adenoid cell carcinoma, lymphoma, acoustic neuroma, acute lymphocytic leukemia, acral lentiginous melanoma, acute myeloid leukemia, acrospiroma, chronic lymphocytic leukemia, acute eosinophilic leukemia, liver cancer, acute erythrocyte leukemia, small cell lung cancer, acute lymphocytic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, mantle cell lymphoma, adenocarcinoma, marginal zone B-cell lymphoma, malignant hippocampal tumor, adenoid cystic carcinoma, gland tumor, adenoma-like odontogenic tumor, mast cell leukemia, adenosquamous carcinoma, mediastinal germ cell tumor, adipose tissue tumor, breast medullary carcinoma, adrenocortical carcinoma, medullary thyroid carcinoma, adult T cell leukemia/lymphoma, Medulloblastoma, invasive NK cell leukemia, melanoma, AIDS-related lymphoma, meningioma, lung rhabdomyosarcoma, Merkel cell carcinoma, alveolar soft tissue sarcoma, mesothelioma, ameloblastoma, metastatic urothelial carcinoma, anaplastic large cell lymphoma, mixed Müllerian tumor, thyroid undifferentiated carcinoma, mucinous neoplasm, angioimmunoblastic T-cell lymphoma, multiple myeloma, angiomyolipoma, muscle tissue tumor, angiosarcoma, mycosis fungoides, astrocytoma, myxoid liposarcoma, atypical deformed rhabdoid tumor, myxoma, B-cell chronic lymphocytic leukemia, mucinous sarcoma, B-cell lymphoblastic leukemia, nasopharyngeal carcinoma, B-cell lymphoma, schwannomas, basal cell carcinoma, neuroblastoma, biliary tract cancer, neurofibromatosis, bladder cancer, neuroma, blastoma, nodular melanoma, bone cancer, eye cancer, Brenner tumor, oligodendroxoma, brown tumor, oligodendroglioma, Burkitt's lymphoma, eosinophilic breast cancer, brain cancer, optic nerve tumor cancer, oral cancer carcinoma in situ, osteosarcoma, carcinosarcoma, ovarian cancer, cartilage tumor, pulmonary sulcus tumor, papillary thyroid carcinoma, myeloma, paraganglioma, chondroma, pineal blastoma, chordoma, pineal cell tumor, choriocarcinoma, pituitary tumor, choroid plexus papilloma, pituitary adenoma, kidney clear cell sarcoma, pituitary tumor, craniopharyngioma, plasmacytoma, cutaneous T-cell lymphoma, multiple embryonic cell tumor, cervical cancer, precursor T lymphoblastic lymphoma, colorectal cancer, primary central nervous system lymphoma, Degos disease, primary effusion lymphoma, proliferative small round cell tumor, primary preformed peritoneal cancer, diffuse large B-cell lymphoma, prostate cancer, embryonic dysplasia of neuroepithelial neoplasia, pancreatic cancer, anaplastic cell tumor, pharyngeal carcinoma, embryonic carcinoma, peritoneal pseudomyxoma, endocrine gland tumor, renal cell carcinoma, enteropathy-associated T-cell lymphoma, endodermal sinus tumor, renal medullary carcinoma, retinoblastoma, esophageal cancer, rhabdomyosarcoma, endadelphos, rhabdomyosarcoma, fibroids, Richter's transformation, fibrosarcoma, rectal cancer, follicular lymphoma, sarcoma, follicular thyroid cancer, schwannoma, ganglion cell tumor, seminoma, gastrointestinal cancer, Sertoli cell turn, germ cell tumor, sex cord-gonadal stromal tumor, pregnancy choriocarcinoma, signet ring cell carcinoma, giant cell fibroblastoma, skin cancer, bone giant cell tumor of bone, small blue round cell tumor, glioma, small cell carcinoma, glioblastoma multiforme, soft tissue sarcoma, glioma, somatostatin tumor, glioma brain, soot wart, pancreatic high glucagonoma, spinal tumor, Gonadoblastoma, spleen marginal lymphoma, granulosa cell tumor, squamous cell carcinoma, estrogen tumor, synovial sarcoma, gallbladder cancer, Sezary disease, gastric cancer, small intestine cancer, hairy cell leukemia, squamous cell carcinoma, hemangioblastoma, gastric cancer, head and neck cancer, T-cell lymphoma, vascular epithelioma, testicular cancer, hematological malignancies, sarcoma, hepatoblastoma, thyroid cancer, hepatosplenic T-cell lymphoma, transitional cell carcinoma, Hodgkin's lymphoma, laryngeal cancer, non-Hodgkin's lymphoma, urachal cancer, invasive lobular carcinoma, genitourinary cancer, intestinal cancer, urothelial carcinoma, renal cancer, uveal melanoma, laryngeal cancer, uterine cancer, malignant freckle-like sputum, verrucous carcinoma, lethal midline granuloma, visual pathway glioma, leukemia, vulvar cancer, testicular stromal tumor, vaginal cancer, liposarcoma, Waldenstrom's macroglobulinemia Disease, lung cancer, adenolymphoma lymphangioma, nephroblastoma, lymphangisarcoma.

The above cancer is preferably lung cancer (for example, small cell lung cancer, non-small cell lung cancer), breast cancer, glioma, gastric cancer, prostate cancer, pancreatic cancer, liver cancer, colon cancer, acute lymphocytic leukemia, more preferably breast cancer, lung cancer (for example, small cell lung cancer, non-small cell lung cancer), prostate cancer, gastric cancer, colon cancer. In certain embodiments, the breast cancer is a triple negative breast cancer. Triple negative breast cancer refers to breast cancer where expression of estrogen receptor, progesterone receptor, and HER2 receptor are not detectable in the cancer cells.

Other diseases and conditions (including cancer) that can be treated by administering the pharmaceutical compositions of the present disclosure are disclosed in U.S. Patent Publication No. 2007/0027135, U.S. Pat. No. 7,432,304, U.S. Patent Publication No. 2010/0278921, WO 2012/017251A1, and WO 2014/113413A1. They are incorporated herein in their entirety.

In certain embodiments, the cancer is a metastatic solid tumor.

In certain embodiments, the cancer is Bcl-2/Bcl-xL and Bax positive. "Bcl-2/Bcl-xL and Bax positive" means that it is characterized by Bcl-2/Bcl-xL and Bax gene amplification or Bcl-2/Bcl-xL and Bax protein overexpression, and therefore the cancerous or malignant cells or tissues have abnormally high levels of Bcl-2/Bcl-xL and Bax genes and/or Bcl-2/Bcl-xL and Bax proteins than normal healthy cells. In certain embodiments, one or more genetic mutations can occur in multiple types of cancer, resulting in cancer cells producing excessive Bcl-2/Bcl-xL and Bax proteins.

In certain embodiments, the patient's cancer is diagnosed as Bcl-2/Bcl-xL and Bax positive. The patient can be diagnosed by methods well known in the art, such as by methods of hybridization detection using nucleic acid probes, methods for nucleic acid amplification, immunoassay methods for protein level, and the like. In certain embodiments, the cancer is gastric cancer. In certain embodiments, the gastric cancer is Bcl-2/Bcl-xL and Bax positive gastric cancer. Bcl-2/Bcl-xL and Bax-positive gastric cancer are characterized in having gastric cancer cells having Bcl-2/Bcl-xL and Bax gene amplification or Bcl-2/Bcl-xL and Bax protein overexpression. In a preferred embodiment, the gastric cancer patient simultaneously overexpresses Bcl-2/Bcl-xL and Bax, i.e., the patient has Bcl-2/Bcl-xL and Bax positive gastric cancer.

In certain embodiments, the cancer is resistant to an EGFR inhibitor.

"Epidermal growth factor receptor" or "EGFR" is a cell surface tyrosine kinase receptor. EGFR is a protein product of the growth-promoting oncogene erbB or ErbB1, a member of the ERBB family of the protooncogenes family, which plays a key role in the development and progression of many types of cancers in human. In particular, enhanced expression of EGFR was observed in breast cancer, bladder cancer, lung cancer, head cancer, cervical cancer and gastric cancer, and glioblastoma. Clinically, ERBB oncogene amplification and/or receptor overexpression in tumors has been reported to be associated with disease recurrence and poor patient prognosis, as well as with response to therapies.

An EGFR inhibitor refers to a molecule capable of inhibiting tyrosine kinase activity of EGFR, and may be a small molecule compound or a biological macromolecule such as an antibody or an antibody fragment or the like. Exemplary small molecule EGFR inhibitors include, but are not limited to, first generation EGFR inhibitors such as gefitinib, erlotinib, ectinib, second generation EGFR inhibitors such as afatinib, dacomitib, imatinib and lapatinib, third-generation EGFR inhibitors such as oxifitinib (AZD9291), nazatinib, rociletinib, naquotinib and the like. Exemplary macromolecular EGFR inhibitors include, but are not limited to, cetuximab and panitumumab.

In some embodiments, the EGFR inhibitor is selected from: gefitinib, erlotinib, ectinib, afatinib, dacomitinib, imatinib, lapatinib, osimertinib (AZD9291), nazatinib, rociletinib, naquotinib, vandetanib, neratinib, pelitinib, canertinib, briatininib, PKC412, Go6976, mavelertinib, olmutinib, WZ4002, TAS2913, cetuximab, panitumumab, avitinib, HS-10296 and TQB3804. In some embodiments, the EGFR inhibitor is osimertinib.

Drug resistance as used herein refers to being refractory or non-responsive to a therapeutic agent, such as an EGFR inhibitor. For example, the number of tumor cells is increased despite of being treated with a therapeutic agent. In certain embodiments, the cancer resistant to EGFR inhibitor is lung cancer (e.g. small cell lung cancer or non-small cell lung cancer).

In certain embodiments, the cancer (e.g. lung cancer) is characterized in expressing a mutated EGFR. The mutated EGFR has one or more mutations selected from the group consisting of L858R, T790M, C797S, and EGFR gene exon 20 insertion. The standard amino acid sequence of EGFR can be found in the sequence shown in accession number P00533-1 in the SwissProt database, and the sequence shown in accession number NP_005219.2 in the NCBI database. The position of the mutation of EGFR in the present application is based on the position in the standard amino acid sequence of EGFR described above. For example, L858R, T790M and C797S refer to leucine at the position 858 of EGFR sequence replaced by arginine, threonine at the position 790 replaced by methionine, and cysteine at the position 797 replaced by serine, respectively. The L858R mutation is located in exon 21 of EGFR. The first generation of EGFR inhibitors can treat patients with EGFR exon 19 deletion or exon 21 L858R mutation, but patients are prone to develop drug resistance. The T790M mutation in EGFR exon 20 was found to be the most common mutation associated with the development of the drug resistance, and T790M will in turn confer resistance to the inhibition by EGFR tyrosine kinase inhibitors. Third-generation EGFR inhibitors are effective on EGFR with a T790M mutation. However, the development of the resistance to third-generation EGFR inhibitors has also been observed, including mutations in the cysteine residue at the position 797.

In certain embodiments, the patient is diagnosed as expressing a mutated EGFR. The patient can be diagnosed by methods well known in the art, for example, by hybridization-based methods using nucleic acid probes that specifically distinguish mutant EGFR and wild-type EGFR, by nucleic acid amplification-based methods, and by detection methods using antibodies that specifically distinguish between mutant EGFR and wild type EGFR, and the like.

It is surprisingly found in the present disclosure that the combination of a Bcl-2/Bcl-xL inhibitor and a chemotherapeutic agent provided herein is useful for the treatment of cancers having an EGFR mutation, including but not limited to cancers having the above EGFR mutation. In certain embodiments, the Bcl-2/Bcl-xL inhibitor is Compound 15 or Compound 31. In certain embodiments, the chemotherapeutic agent comprises a tubulin inhibitor. In certain embodiments, the chemotherapeutic agent is docetaxel, fluorouracil (e.g. 5-fluorouracil), panobinstat, or cisplatin.

In a preferred embodiment, the pharmaceutical composition of the invention comprises a combination of Compound 15 or Compound 31 and docetaxel. It is unexpectedly found by the inventors that the use of the combination of Compound 15 or Compound 31 and docetaxel produces a significant anti-cancer effect superior to Compound 15, Compound 31 or Docetaxel alone.

In a preferred embodiment, the pharmaceutical composition of the invention comprises a combination of Compound 15 or Compound 31 and 5-fluorouracil. It is unexpectedly found by the inventors that the combination of Compound 15 or Compound 31 with 5-fluorouracil produces a significantly superior anti-cancer effect superior to Compound 15, Compound 31 or 5-fluorouracil alone.

In a preferred embodiment, the pharmaceutical composition of the invention comprises a combination of Compound 15 or Compound 31 and a histone acetylation inhibitor (panobinstat). It is unexpectedly found by the inventors that the use of the combination of Compound 15 or Compound 31 and panobinstat produces a significantly superior anti-cancer effect superior to Compound 15, Compound 31 or pinobinstat alone.

In a preferred embodiment, the pharmaceutical composition of the invention comprises a combination of Compound 15 or Compound 31 and cisplatin. It is unexpectedly found by the inventors that the use of the combination of Compound 15 or Compound 31 and cisplatin produces a significant anti-cancer effect superior to Compound 15, Compound 31 or cisplatin alone.

In a preferred embodiment, the pharmaceutical composition of the invention comprises a combination of Compound 15 or Compound 31 and irinotecan. It is unexpectedly found by the inventors that the use of the combination of Compound 15 or Compound 31 and irinotecan produces a significant anti-cancer effect superior to Compound 15, Compound 31 or irinotecan alone.

In a preferred embodiment, the pharmaceutical composition of the invention comprises a combination of Compound 15 or Compound 31 and paclitaxel. It is unexpectedly found by the inventors that the use of the combination of Compound 15 or Compound 31 and paclitaxel produces a significant anti-cancer effect superior to Compound 15, Compound 31 or paclitaxel alone.

In a preferred embodiment, the pharmaceutical composition of the invention comprises a combination of Compound 15 or Compound 31 and topotecan. It is unexpectedly found by the inventors that the use of the combination of Compound 15 or Compound 31 and topotecan produces a significant anti-cancer effect superior to Compound 15, Compound 31 or topotecan alone.

Method of Treatment

According to a second aspect of the invention, provided herein is a method for treating cancer comprising administering a therapeutically effective amount of a Bcl-2/Bcl-xL inhibitor and a therapeutically effective amount of a chemotherapeutic agent to an individual in need thereof, wherein the Bcl-2/Bcl-xL inhibitor and the chemotherapeutic agent are respectively as defined above. The cancer is also as defined above.

The term "treatment" as used herein refers to eliminating, reducing or ameliorating a disease or condition and/or a symptom associated therewith. For example, "treatment of cancer" includes treating, suppressing cancer, reducing its severity, reducing its risk, or inhibiting its metastasis. Although not excluded, treatment of a disease or condition does not require that the disease, condition, or symptoms associated therewith be completely eliminated. The term "treatment" as used herein may include "prophylactic treatment", which refers to reducing the possibility of recurrence of a disease or condition, or reducing the possibility of relapse of a previously controlled disease or condition, in a subject who is not afflicted with a disease but at risk, or who is susceptible to recurrence of the disease or condition, or who is at risk or susceptible to relapse of the disease or condition. The term "treatment" and synonyms are intended to give a therapeutically effective amount of a compound of the invention to an individual in need thereof.

Within the meaning of the invention, "treatment" also includes prevention of relapse or prevention stages, as well as treatment of acute or chronic signs, symptoms and/or dysfunction. Treatment can target symptoms, for example, to suppress symptoms. It can function in a short period of time, for a medium period of time, or can be a long-term treatment, such as in the case of maintenance therapy.

The term "therapeutically effective amount" or "effective amount" as used herein refers to an amount of the active ingredient which, when administered by the methods of the present disclosure, is sufficient to effectively deliver the active ingredient to an individual in need thereof for the treatment of a target condition. In the case of cancer or other proliferative disorders, a therapeutically effective amount of the agent can reduce undesired cell proliferation, reduce the number of cancer cells, reduce tumor size; inhibit cancer cell infiltration to surrounding organs; inhibit tumor metastasis; inhibit tumor growth to a certain extent; reduce Bcl-2/Bcl-xL signaling in targeted cells; and/or alleviate one or more symptoms associated with cancer to a certain extent.

In the method of treatment of the invention, a therapeutically effective amount of a Bcl-2/Bcl-xL inhibitor can be administered to the patient before, after or simultaneously with the administration of a therapeutically effective amount of the chemotherapeutic agent to the individual in need thereof; wherein the Bcl-2/Bcl-xL inhibitor and the chemotherapeutic agent can each be combined with a pharmaceutically acceptable carrier.

In the method of treatment of the invention, the Bcl-2/Bcl-xL inhibitor and the chemotherapeutic agent can be administered together as a single unit dose or separately as multiple unit doses.

In certain embodiments, the Bcl-2/Bcl-xL inhibitor may be administered in an amount from about 0.005 to about 500 mg/day, preferably from about 0.05 to about 250 mg/day, more preferably from about 0.5 to about 100 mg/day. In certain embodiments, the Bcl-2/Bcl-xL inhibitor is administered at a dose from about 10 mg/week to about 1000 mg/week, from about 10 mg/week to about 900 mg/week, from about 10 mg/week to about 800 mg/Week, about 10 mg/week to about 700 mg/week, about 10 mg/week to about 640 mg/week, about 10 mg/week to about 600 mg/week, about 10 mg/week to about 500 mg/week, about 10 mg/week to about 400 mg/week, about 10 mg/week to about 300 mg/week, about 10 mg/week to about 200 mg/week, or about 20 mg/week to about 100 mg/week, for example about 10, 15, 20, 25, 30, 35, 40, 50, 55, 60, 65, 70, 75, 80, 85, 90, 95, 100, 150, 200, 250, 300, 350, 400, 450, 500, 550, 600, 650, 700, 750, 800, 850, 900, 950, 1000 mg/week. In certain embodiments, the Bcl-2/Bcl-xL inhibitor is administered at a dose of about 0.005, 0.05, 0.5, 5, 10, 20, 30, 40, 50, 100, 150, 200, 250, 300, 350, 400, 450 or 500 mg per dose. In certain embodiments, the Bcl-2/Bcl-xL inhibitor is administered at a frequency of once a week, twice a week, three times a week, four times a week, five times a week, six times a week or seven times a week.

In certain embodiments, the chemotherapeutic agent can be administered in an amount from 0.005 mg/day to about 5000 mg/day, including about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

Pharmaceutical Use

According to a third aspect of the present disclosure, provided herein is use of a combination of a Bcl-2/Bcl-xL inhibitor and a chemotherapeutic agent in the manufacture of a medicament for treating cancer, wherein the Bcl-2/Bcl-xL inhibitor and the chemotherapeutic agent are respectively as defined above. The cancer is also as defined above.

The pharmaceutical composition of the present disclosure can be administered by any suitable route, for example, by oral, buccal, inhalation, sublingual, rectal, vaginal, intracisternal or intrathecal via lumbar puncture, transurethral, nasal, or transdermal, or parenteral (including intravenous, intramuscular, subcutaneous, intracoronary, intradermal, intramammary, intraperitoneal, intra-articular, intrathecal, posterior ocular, intrapulmonary, and/or surgical implantation at specific sites). Parenteral administration can be accomplished using a needle and syringe or using high pressure techniques. In certain embodiments, the Bcl-2/Bcl-xL inhibitor and the chemotherapeutic agent can be administered via the same or different routes of administration. In certain embodiments, the route of administration includes oral, intravenous or subcutaneous injection.

The toxicity and therapeutic efficacy of the pharmaceutical compositions of the invention can be determined in cell cultures or experimental animals by standard pharmaceutical procedures, for example to determine the maximum tolerated dose (MTD) of each component, which is defined as the highest dose not causing toxicity in the animal. Therapeutic index is the dose ratio between the maximum tolerated dose and the dose that provides therapeutic effect (e.g., inhibition of tumor growth). The dosage can vary within this range, depending on the dosage form employed and the route of administration employed.

Therapeutically effective amounts of Bcl-2/Bcl-xL inhibitors and chemotherapeutic agents required for pharmaceutical use will vary with the nature of the condition being treated, the length of time required for the activity, and the age and condition of the patient. The amount and interval of administration can be adjusted separately to provide a plasma level of the combination of drugs sufficient to maintain the desired therapeutic effect. The desired dose can be conveniently administered in a single dose or in multiple doses at appropriate intervals, for example, one, two, three, four or more sub-doses per day. Multiple doses are often necessary or required. For example, the pharmaceutical composition of the present disclosure can be administered at the following frequency: 1 dose/day for 2 days, off for 5 days, lasting for 2 weeks; 1 dose/day for 3 days, off for 4 days, lasting for 3 weeks; once a week for 2 weeks; once a week for 4 weeks; or any dosage regimen as appropriate. In certain embodiments, the Bcl-2/Bcl-xL inhibitor and the chemotherapeutic agent can be administered together, simultaneously, sequentially or alternately.

The pharmaceutical compositions of the present disclosure are usually administered in admixture with a pharmaceutically acceptable carrier which is selected according to the intended route of administration and standard pharmaceutical practice. Pharmaceutical compositions for use in accordance with the present disclosure are formulated in a conventional manner using one or more pharmaceutically acceptable carriers.

The pharmaceutical compositions of the present disclosure can be prepared, for example, by conventional mixing, dissolving, granulating, tableting, emulsifying, encapsulating, capturing or lyophilizing processes. Suitable formulations will depend on the route of administration. When administered orally, the composition will usually be in the form of a tablet, capsule, powder, solution or elixirs. When administered in the form of a tablet, the composition may additionally comprise a solid carrier such as gelatin or an adjuvant. Tablets, capsules and powders contain from about 0.01% to about 95% of a Bcl-2/Bcl-xL inhibitor by weight. When administered in liquid form, a liquid carrier such as water, an alcohol or an oil of animal or vegetable origin may be added. The composition in liquid form may further comprise a physiological saline solution, glucose or other sugar solution or glycerin. When administered in liquid form, the compositions contain from about 0.1% to about 90% of a Bcl-2/Bcl-xL inhibitor by weight.

When a therapeutically effective amount of a pharmaceutical composition of the invention is administered by intravenous, cutaneous or subcutaneous injection, the composition is in the form of a non-pyrogenic, parenterally acceptable aqueous solution. Such a parenterally acceptable solution can be prepared with appropriate consideration of pH, isotonicity, stability, and the like within the skill of the art. Preferred compositions for intravenous, cutaneous or subcutaneous injection typically contain an isotonic solvent.

Bcl-2/Bcl-xL inhibitors and/or chemotherapeutic agents can be readily combined with pharmaceutically acceptable carriers well known in the art. Such a carrier allows the active agent to be formulated into a tablet, pill, lozenge, capsule, liquid, gel, syrup, ointment, suspension, and the like. The pharmaceutical preparation for oral administration can be obtained by adding the active ingredients and a solid excipient, grinding the resulting mixture, and after adding a suitable auxiliary agent if necessary, granulating and pressing to obtain a tablet or tablet core. Suitable excipients include, for example, fillers, cellulose formulations, disintegrants, binders, lubricants, and the like.

Bcl-2/Bcl-xL inhibitors and/or chemotherapeutic agents are formulated for parenteral administration, for example by bolus injection or continuous infusion. The injectable preparation may be provided in unit dosage form, for example in ampoules or in multi-dose containers, with added preservatives. The composition may be in a form such as a suspension in an oily or aqueous solvent, solution or emulsion, and may contain adjuvants such as suspending agents, stabilizers and/or dispersants.

Pharmaceutical compositions for parenteral administration include aqueous solutions of the active agents in aqueous form. In addition, suspensions of Bcl-2/Bcl-xL inhibitors and/or chemotherapeutic agents can be prepared as suitable oily injection suspensions. Suitable lipophilic solvents include fatty oils or synthetic fatty acid esters. Aqueous injection suspensions may contain substances which increase the viscosity of the suspension. Optionally, the suspension may also contain suitable stabilizers or agents which increase the solubility of the compound and allow for the preparation of highly concentrated solutions. Alternatively, the compositions of the present disclosure may be in powder form for constitution with a suitable solvent such as sterile non-pyrogenic water prior to use.

Bcl-2/Bcl-xL inhibitors and/or chemotherapeutic agents may also be formulated in rectal compositions, such as suppositories or retention enemas, for example, containing conventional suppository bases. In addition to the aforementioned formulations, Bcl-2/Bcl-xL inhibitors and/or chemotherapeutic agents can also be formulated as depot preparations. Such long acting formulations may be administered by implantation (for example subcutaneously or intramuscularly) or by intramuscular injection. Thus, for example, a Bcl-2/Bcl-xL inhibitor and/or a chemotherapeutic agent can be formulated with a suitable polymeric or hydrophobic material (e.g., as an emulsion in an acceptable oil) or an ion exchange resin.

In particular, the Bcl-2/Bcl-xL inhibitor and/or chemotherapeutic agent may be in the form of a tablet containing an excipient such as starch or lactose, or in the form of a capsule mixed with an excipient, or in the form of an elixir or suspension containing a flavoring agent or a colorant, for oral, buccal or sublingual administration. The above liquid preparations may be formulated together with a pharmaceutically acceptable additive such as a suspending agent. Bcl-2/Bcl-xL inhibitors and/or chemotherapeutic agents can also be administered parenterally, such as intravenously, intramuscularly, subcutaneously or intracoronally. For parenteral administration, it is preferably used in the form of a sterile aqueous solution which may contain other substances such as salts or monosaccharides such as mannitol or glucose to render the solution isotonic with blood.

Anticancer Effect of Bcl-2/Bcl-xL In Vivo

In another aspect, the present application also provides a method for treating cancer in a patient in need thereof by administering to the patient an effective amount of a Bcl-2/Bcl-xL inhibitor (e.g., Compound 15 or Compound 31). In certain embodiments, the Bcl-2/Bcl-xL inhibitor is a single agent. In certain embodiments, the Bcl-2/Bcl-xL inhibitor acts as an agent in combination with other therapeutic agents, such as chemotherapeutic agents, for combination therapy.

In certain embodiments, the Bcl-2/Bcl-xL inhibitor is Compound 15 or Compound 31. In certain embodiments, the method for treating cancer comprises administering to a patient in need thereof a therapeutically effective amount of a Bcl-2/Bcl-xL inhibitor, such as Compound 15 or Compound 31, wherein the method comprises at least one 28-day treatment cycle wherein the Bcl-2/Bcl-xL inhibitor is administered by intravenous infusion twice a week (e.g., Compound 15 or Compound 31 administered by intravenous infusion over 30 minutes on days 1, 4, 8, 11, 15, 18 and 22 of each treatment cycle, 28 days for one treatment cycle) or once a week (e.g., Compound 15 or Compound 31 administered by intravenous infusion over 30 minutes on days 1, 8, 15, and 22 of the treatment cycle, 28 days for one treatment cycle) for 4 consecutive weeks. The treatment cycle can be repeated as many times as needed. The therapeutically effective amount is from about 10 mg to about 400 mg of a Bcl-2/Bcl-xL inhibitor.

In some embodiments, the therapeutically effective amount of the Bcl-2/Bcl-xL inhibitor is about 20 mg.

In some embodiments, the therapeutically effective amount of the Bcl-2/Bcl-xL inhibitor is about 40 mg.

In some embodiments, the therapeutically effective amount of the Bcl-2/Bcl-xL inhibitor is about 80 mg.

In some embodiments, the therapeutically effective amount of the Bcl-2/Bcl-xL inhibitor is about 120 mg.

In some embodiments, the therapeutically effective amount of the Bcl-2/Bcl-xL inhibitor is about 160 mg.

In some embodiments, the therapeutically effective amount of the Bcl-2/Bcl-xL inhibitor is about 200 mg.

In some embodiments, the therapeutically effective amount of the Bcl-2/Bcl-xL inhibitor is about 240 mg.

In some embodiments, the therapeutically effective amount of the Bcl-2/Bcl-xL inhibitor is about 280 mg.

In some embodiments, the therapeutically effective amount of the Bcl-2/Bcl-xL inhibitor is about 320 mg.

In some embodiments, the therapeutically effective amount of the Bcl-2/Bcl-xL inhibitor is about 360 mg.

In some embodiments, the therapeutically effective amount of the Bcl-2/Bcl-xL inhibitor is about 400 mg.

EXAMPLES

The concept of the present disclosure and the technical effects produced by the present disclosure will be further described in conjunction with the embodiments, so that those skilled in the art can fully understand the objects, features and effects of the present disclosure. It is understood that the following examples are merely illustrative and are not intended to limit the scope of the invention.

Synthesis of Bcl-2/Bcl-xL Inhibitor

Compound 15: (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy) ethylphosphonic acid. The method for synthesizing Compound 15 can be prepared by the following method by referring to the description in the specification of WO2014/113413A.

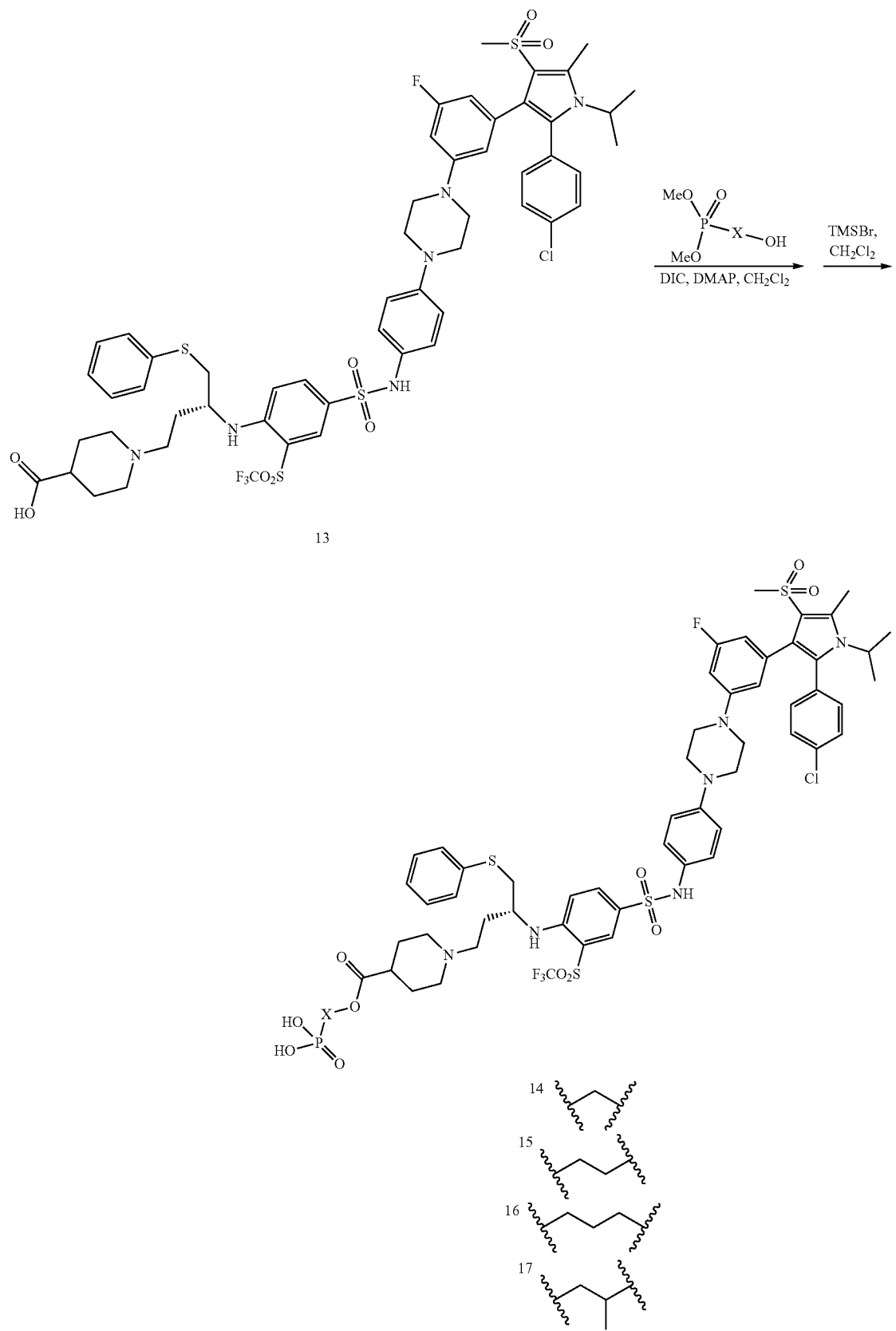

¹H NMR (300 MHz, CD₃OD): δ7.93 (d, J=1.9 Hz, 1H), 7.72 (dd, J=9.2, 1.8 Hz, 1H), 7.30-7.12 (m, 12H), 6.83-6.42 (m, 5H), 4.46-4.33 (m, 3H), 3.96 (s, 1H), 3.54-2.93 (m, 16H), 2.82 (s, 3H), 2.72 (s, 3H), 2.71-2.55 (m, 1H), 2.24-1.65 (m, 8H), 1.41 (d, J=7.1 Hz, 6H). MS (ESI): m/z 1268.58 (M+H)⁺.

Compound 31: (R)-1-(3-(4-(N-(4-(4-(3-(2-(4-chlorophenyl)-1)-isopropyl-5-methyl-4-(methylsulfonyl)-1H-pyrrol-3-yl)-5-fluorophenyl) piperazin-1-yl)phenyl) sulfamoyl)-2-(trifluoromethylsulfonyl)phenylamino)-4-(phenylthio) butyl)piperidine-4-carboxylic acid. The method for synthesizing Compound 15 can be prepared by the following method by referring to the description in the specification of WO2014/113413A.

μL cell suspension in complete medium was added at a density of 5-10×10⁴ cells/well to each well to be tested.

The MGC80-3 and SW620 used in the examples were purchased from the Cell Bank of the Shanghai Institute of Biochemistry and Cell Biology, Chinese Academy of Sciences. MDA-MB-231, PC-3, and NCI-H146 were available from the American Type Culture Collection (ATCC) under accession Nos. HTB-26, CRL-1435, and HTB-173, respectively. It should be noted that the cells used in the present disclosure are all available from ATCC. The culture conditions of MGC80-3, PC-3, and NCI-H146 were RPMI 1640 medium, 10% fetal bovine serum and 1% dual antibiotics solution. The culture conditions of MDA-MB-231 were minimal essential medium (containing 0.1 mM non-essential

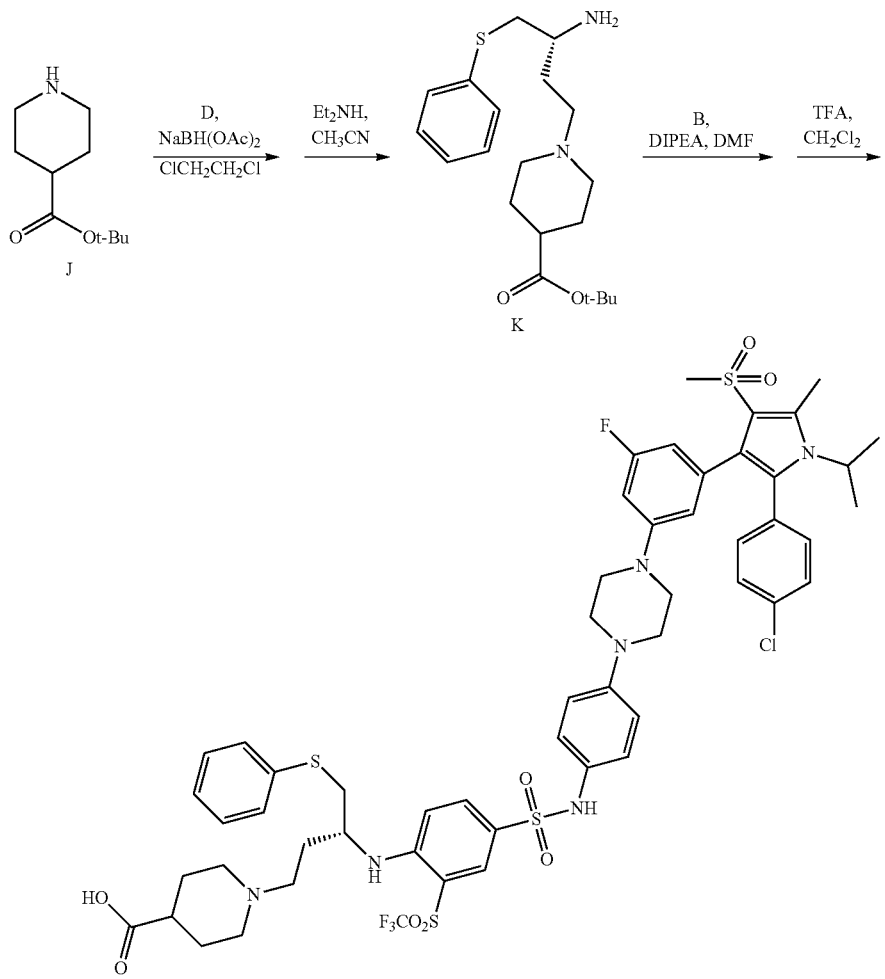

¹H NMR (400 MHZ, DMSO-d6) δ 9.84 (s, 1H), 7.82 (s, 1H), 7.65 (d, J=8.7 Hz, 1H), 7.38 (d, J=8.5 Hz, 2H), 7.32-7.14 (m, 7H), 7.11-6.81 (m, 6H), 6.63-6.47 (m, 2H), 6.43-6.30 (m, 1H), 4.33 (p, J=7.1 Hz, 1H), 4.07 (s, 1H), 3.32-3.22 (m, 4H), 3.19-3.03 (m, 9H), 2.89 (s, 4H), 2.67 (s, 4H), 2.31-1.55 (m, 8H), 1.35 (d, J=7.0 Hz, 6H).

WST Experiment

Cell plating: Anti-proliferation effects were detected by a CCK-8 (Cell Counting Kit-8) assay based on water soluble tetrazolium salt (WST).

The cells were seeded in 96-well plates. 95 μL complete medium was added to each negative control group, and 95 amino acids and 1.0 mM sodium pyruvate), 10% fetal bovine serum and 1% dual antibiotics solution. The culture conditions of SW620 were Leibovitz's L-15 medium, 10% fetal bovine serum and 1% dual antibiotics solution.

Treatment (light protection): In the 96-well culture plate, considering that different cells had different sensitivity to drugs, the highest concentration was selected as 10 μM, and 9 concentrations were obtained by 1:3 serial dilutions. 5 μL of compound was added to each well and each concentration was prepared in 2-3 replicate wells. The 96-well plates were incubated in a 5% CO₂ incubator at 37° C. for 72 hours after the addition of the testing compound as different concentrations. The synergy of the drug with Compound 15 was tested by the treatment with the drug (e.g. docetaxel) at 9 different concentrations and Compound 15 at 3 fixed concentrations for 72 hours. Each concentration was tested in triplicates.

Reading: At the end of the culture, for adherent cells, the old solution in the test wells was removed and 100 µl/well CCK-8 test solution (the corresponding medium containing 10% CCK-8, 5% FBS) was added. For suspension cells, CCK-8 stock solution was added directly at 20 µl/well. The plates were incubated at 37° C. in a $CO_2$ incubator for 2-4 hours.

The OD value was measured using a microplate reader (SpectraMax Plus 384, Molecular Devices, LLC., US) A450 nm. Mean OD value was taken from triplicate wells. The percentage of cell viability was calculated by the following formula:

(O.D. test well−O.D. blank control well)/(O.D. cell control well×O.D. blank control well)×100%.

Figure 1:
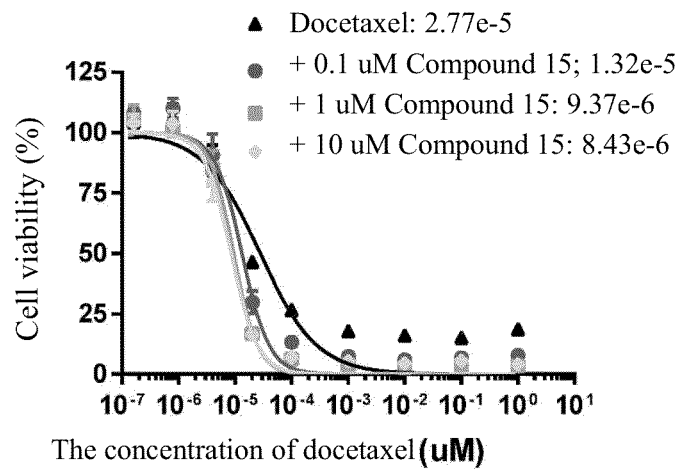
FIG. 1 shows the inhibiting effect of combination therapy of Compound 15 (i.e., Compound 15 described in Table 1 below) and docetaxel on cell proliferation in breast cancer xenograft model of mice bearing human MDA-MB-231 cell line.

The $IC_{50}$ was calculated using the nonlinear regression data analysis method of Graphpad Prism 6.0 software. The results are shown in FIG. 1 and Table 2.

For the combination study, the mean OD value of the triplicate wells of the single drug control was normalized to calculate cell viability. The synergistic effect of the two compounds was determined by comparing the IC50 of the combination curve with the single drug curve (the combination curve shifted to the left).

Evaluation Method of In Vivo Pharmacodynamic Study

Subcantaneous xenograft tumor model of human cancer was established in immunodeficient mouse by cell inoculation: tumor cells in logarithmic growth phase were collected, counted, and then re-suspended in 1×PBS. The concentration of the cell suspension was adjusted to $2.5\text{-}5\times10^7$/mL. Tumor cells were inoculated subcutaneously in the right back of the immunized normal mouse with a 1 mL syringe (4 gauge needle) at $5\text{-}10\times10^6$/0.2 mL/mouse. Relevant parameters were calculated with reference to China's NMPA "Guidelines for Non-clinical Research Techniques of Cytotoxic Antitumor Drugs".

Animal weight and tumor size were measured twice a week during the study. The animals were checked daily for morbidity and etc. At the time of routine monitoring, the animal were checked for any effects of tumor growth and treatments on behaviors such as mobility, food and water consumption, body weight gain/loss, eyes, hairing and any other abnormalities. Mortality and clinical signs observed during the study were recorded in the raw data. The dosing of the drugs and the measurement of mouse weight and tumor volume were all conducted in a laminar flow cabinet. According to requirements of the study protocol, plasma and tumor tissue were collected, weighed and photographed at the end of last dosing. Plasma and tumor samples were frozen at −80° C. for later use.

Tumor volume (TV) was calculated as:

$$TV = a \times b^2/2$$

wherein a and b represent the measured length and width of tumor, respectively.

Relative tumor volume (RTV) was calculated as:

$$RTV = V_t/V_1$$

wherein $V_1$ was the tumor volume on the first day of dosing, and $V_t$ was the tumor volume measured on day t after dosing.

Relative tumor proliferation rate T/C (%), as an indication of anti-tumor effectiveness, was calculated as:

Relative tumor proliferation rate $T/C\ (\%) = (T_{RTV}/C_{RTV}) \times 100\%$, wherein $T_{RTV}$ was RTV in treatment group, and $C_{RTV}$ was RTV in vehicle control group.

Tumor remission rate (%) was calculated by dividing the number of tumor bearing mice that show SD (stable disease), PR (partial regression) and CR (complete regression) after treatment by the total number of mice in the group× 100%.

Change of body weight (%)=(measured body weight−body weight at randomization)/body weight at randomization×100%.

Efficacy evaluation criteria: according to China's NMPA "Guidelines for Non-clinical Research Techniques of Cytotoxic Antitumor Drugs" (November 2006), T/C (%) value ≤40% and p≤0.05 by statistical analysis were considered as efficacious. A weight loss of mice greater than 20%, or greater than 20% drug death are considered to indicate an excessively toxic dosage.

In Vitro Results

As shown in FIG. 1 and Table 2, in MDA-MB-231 triple-negative breast cancer tumor cell line, combination therapy using Compound 15 and docetaxel (TXT) demonstrated a stronger inhibition effect on tumor cell proliferation, as indicated by a combination curve shifted to left. The IC50 value of the combination therapy group was lower than the IC50 of each monotherapy group.

TABLE 2

Results of Compound 15 and docetaxel administered in combination or alone

| Component A | Component B | Cell line | $IC_{50}$(A alone) | $IC_{50}$(B alone) | $IC_{50}$(combination of A + B) |
|---|---|---|---|---|---|
| Compound 15 | docetaxel | MDA-MB-231 | 2.599/ 4.554 µM | 2.77e−5/ 7.87e−5 µM | 9.37e−6/ 1.62e−5 µM |

In Vivo Test

Figure 2:
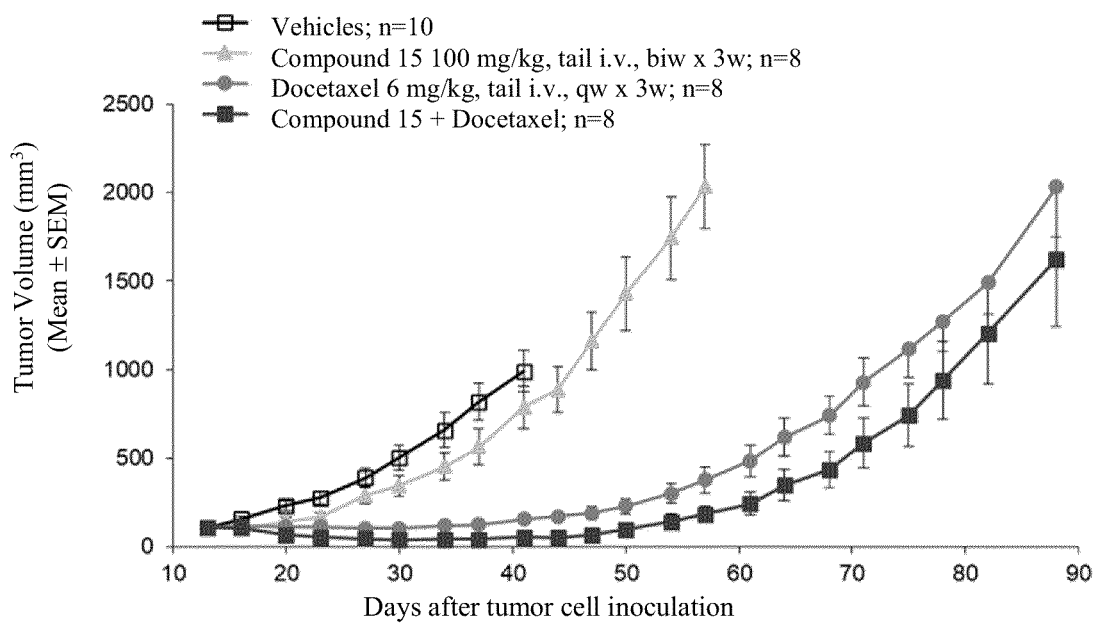
FIG. 2 shows the anti-cancer effect of combination therapy of Compound 15 and docetaxel in breast cancer xenograft model of mice bearing human MDA-MB-231 cell line.

Example 1. Combinatory Anti-Cancer Effect of Compound 15 in Combination with Docetaxel in Breast Cancer Xenograft Model of Mice Bearing Human MDA-MB-231 Cell Line MDA-MB-231 is a model of human triple-negative breast cancer. This study evaluated the anti-cancer therapeutic effect of Compound 15 in combination with docetaxel in the xenograft model. As shown in FIG. 2, Compound 15 (100 mg/kg) enhanced the anti-cancer effect of docetaxel as a single agent. Complete regression was observed in ⅛ of the tumors at the end of dosing and lasted until the end of the study in the group dosed with Compound 15 (100 mg/kg) and docetaxel. The study results show that a more significant anti-cancer effect was achieved in triple-negative breast cancer when Compound 15 and docetaxel were administered in combination than alone.

Figure 3:
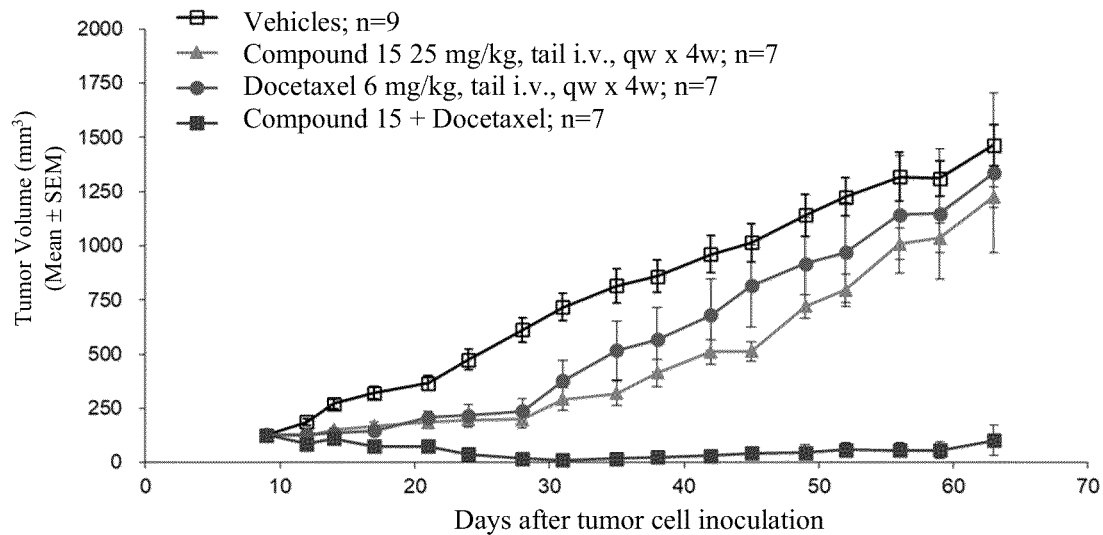
FIG. 3 shows the anti-cancer effect of combination therapy of Compound 15 and docetaxel in small cell lung cancer xenograft model of mice bearing human NCI-H146 cell line.

Example 2. Combinatory Anti-Cancer Effect of Compound 15 in Combination with Docetaxel in Xenograft Model of Mice Bearing Human NCI-H1146 Cell Line Small Cell Lung Cancer This study investigated the anti-cancer therapeutic effect of Compound 15 in combination with docetaxel in the human NCI-H146 small cell lung cancer model. As shown in FIG. 3, Compound 15 (25 mg/kg) enhanced the anti-cancer effect of docetaxel as a single agent. On day 4 of dosing, in the group administered with Compound 15 (25 mg/kg) and docetaxel, partial tumor regression was observed in 1 out of the 7 study animals, and after three weeks, complete tumor regression was observed in 5 out of the 7 study animals. The study results show that a more significant anti-cancer effect was achieved in small cell lung cancer when Compound 15 and docetaxel were administered in combination than alone.

Figure 4:
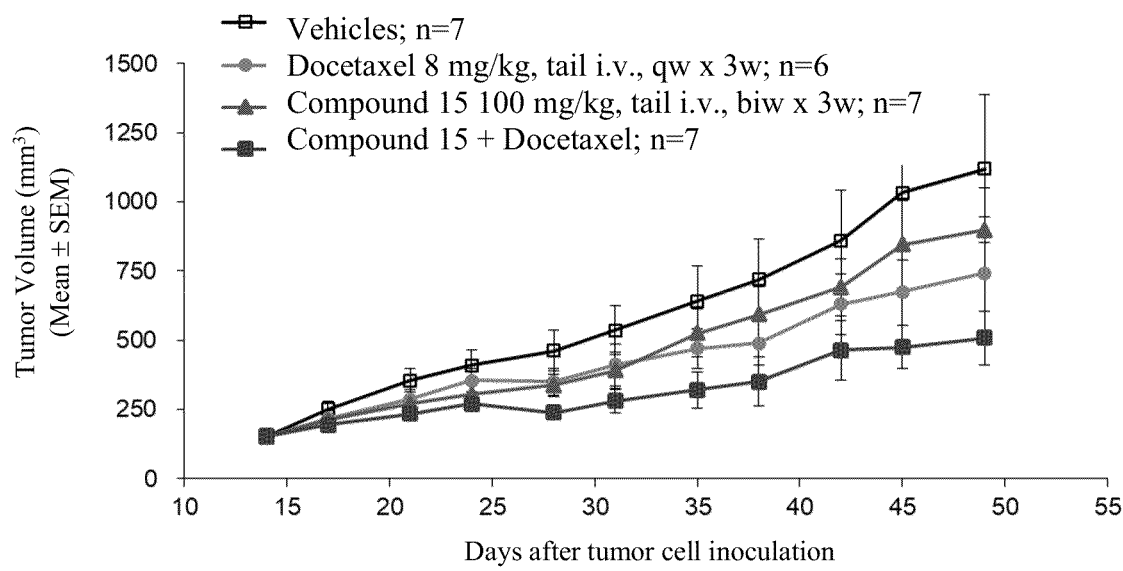
FIG. 4 shows the anti-cancer effect of combination therapy of Compound 15 and docetaxel in prostate cancer xenograft model of mice bearing human PC3 cell line.

Example 3. Combinatory Anti-Cancer Effect of Compound 15 in Combination with Docetaxel in Xenograft Model of Mice Bearing Human PC3 Cell Line Prostate Cancer This study investigated the anti-cancer therapeutic effect of Compound 15 and docetaxel in the PC3 human prostate cancer model. As shown in FIG. 4, Compound 15 (100 mg/kg) enhanced the anti-cancer effect of docetaxel as a single agent. Compound 15 (100 mg/kg) alone showed a minor anti-cancer effect with T/C (%) of 84.4% (P=0.4665). Docetaxel (8 mg/kg) alone also showed a minor anti-cancer effect with T/C (%) of 72.4% (P=0.1579). Compound 15 combined with docetaxel showed better anti-cancer effect than the single drug with T/C (%) of 51.5% (P=0.0209). The study results showed that a more significant anti-cancer effect was achieved in prostate cancer when Compound 15 and docetaxel were administered in combination than alone.

Figure 5:
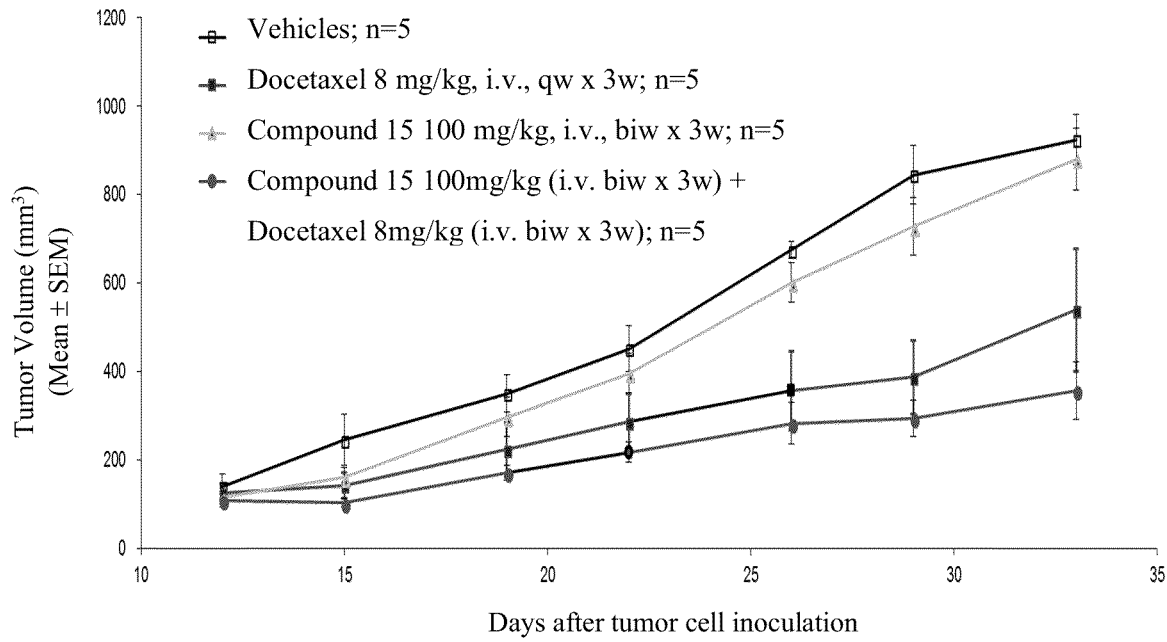
FIG. 5 shows the anti-cancer effect of combination therapy of Compound 15 and docetaxel in gastric cancer xenograft model of mice bearing human MGC80-3 cell line.

Example 4. Combinatory Anti-Cancer Effect of Compound 15 in Combination with Docetaxel or Cisplatin in Xenograft Model of Mice Bearing Human MGC80-3 Cell Line Gastric Cancer This study investigated the anti-cancer therapeutic effect of Compound 15 with docetaxel or cisplatin in the MGC80-3 human gastric cancer model. As shown in FIG. 5, Compound 15 (100 mg/kg) enhanced the anti-cancer effect of docetaxel as a single agent. Docetaxel (8 mg/kg) alone showed a minor anti-cancer effect with T/C (%) of 54.5% (P=0.6650). Compound 15 combined with docetaxel showed a more significant anti-cancer effect than docetaxel alone with T/C (%) of 47.8% (P=0.0572).

Figure 6:
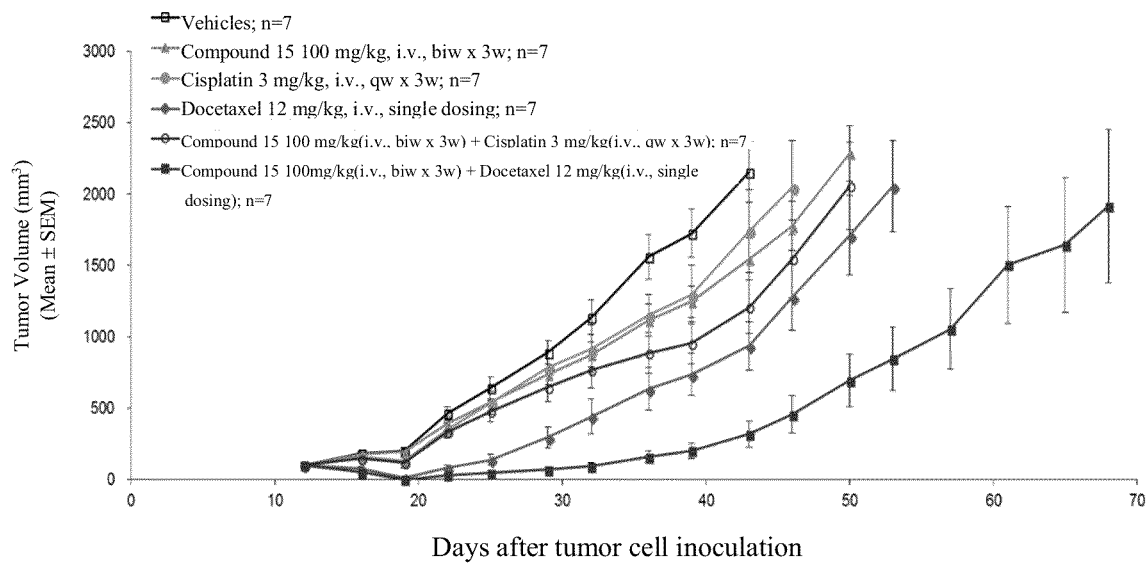
FIG. 6 shows the anti-cancer effect of combination therapy of Compound 15 and docetaxel or cisplatin in gastric cancer xenograft model of mice bearing human MGC80-3 cell line.

As shown in FIG. 6, Compound 15 (100 mg/kg) increased the anti-cancer effect of docetaxel or cisplatin as a single agent. Docetaxel (12 mg/kg) alone showed a minor anti-cancer effect with T/C (%) of 39.0% (P=0.0003). Compound 15 combined with docetaxel showed more significant anti-cancer effect than docetaxel alone with T/C (%) of 7.8% (P<0.0001), and complete tumor regression was observed in 2 out the 7 study animals at the third week of dosing. The group treated with cisplatin (3 mg/kg) alone showed T/C (%) of 65.0% (P=0.0034) at the end of dosing, and the group treated with Compound 15 and cisplatin showed T/C (%) of 53.6% (P=0.0001).

The above study results show that a more significant anti-cancer effect was achieved in gastric cancer when Compound 15 and docetaxel or cisplatin were administered in combination than alone.

Figure 7:
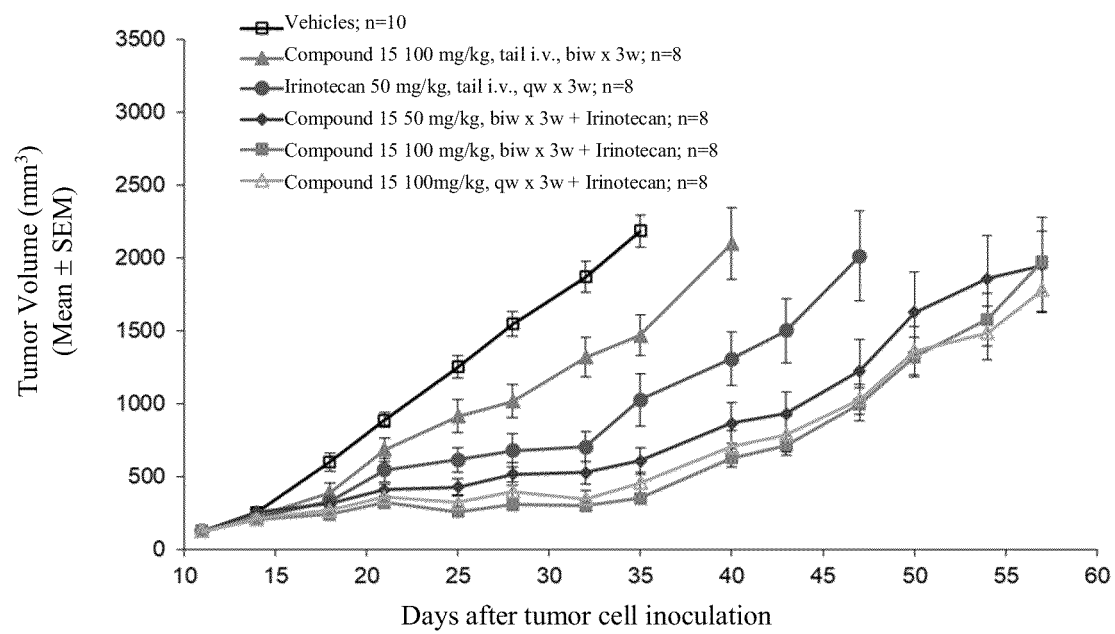
FIG. 7 shows the anti-cancer effect of combination therapy of Compound 15 with irinotecan in colon cancer xenograft model of mice bearing human SW620 cell line.
Figure 8:
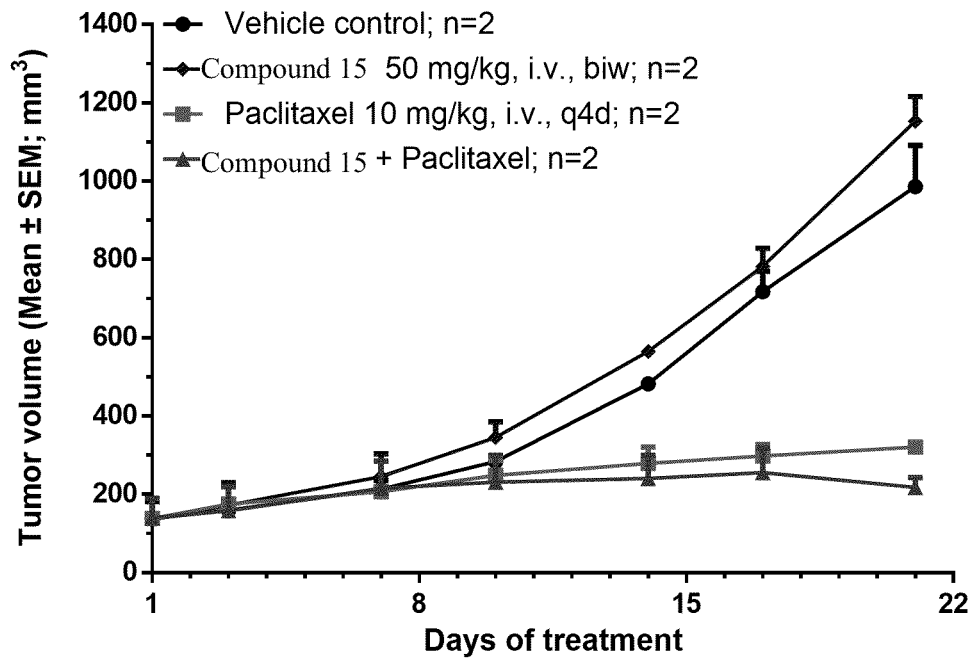
FIG. 8 shows the combination therapy of Compound 15 and paclitaxel (FIG. 8(a)) or irinotecan (FIG. 8(b)) in a subcutaneous LU5250 SCLC PDX model.
Figure 8:
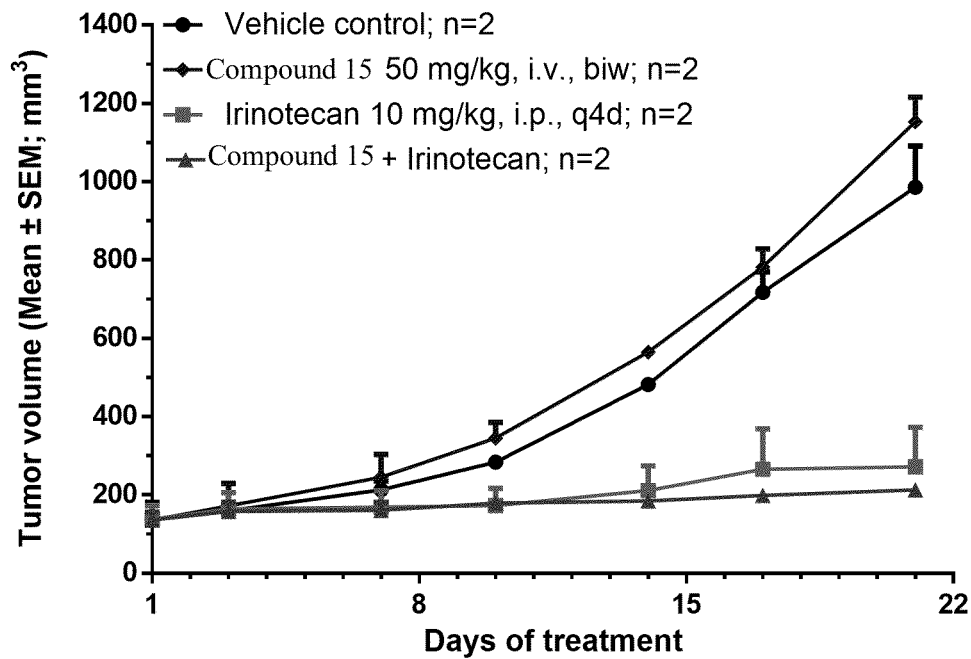
Figure 9:
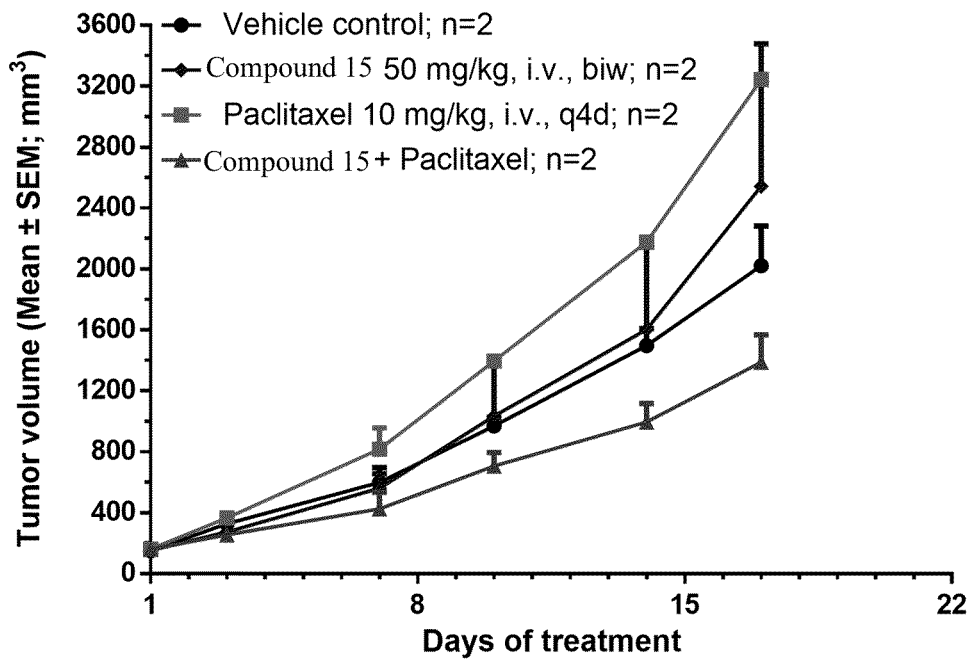
FIG. 9 shows the combination therapy of Compound 15 and paclitaxel (FIG. 9(a)) or irinotecan (FIG. 9(b)) in a subcutaneous LU5188 SCLC PDX model.
Figure 9:
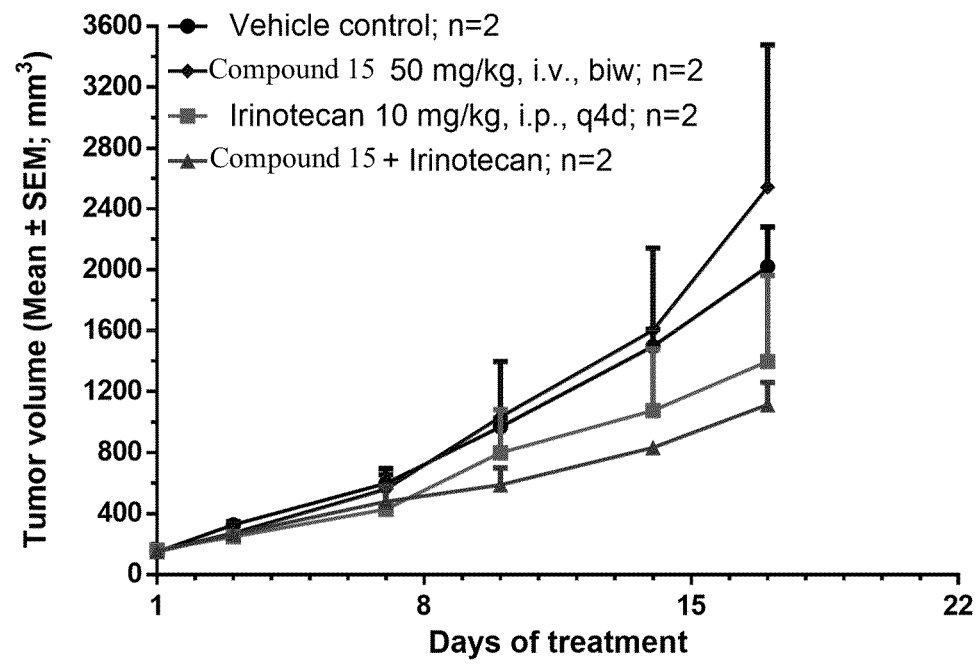
Figure 10:
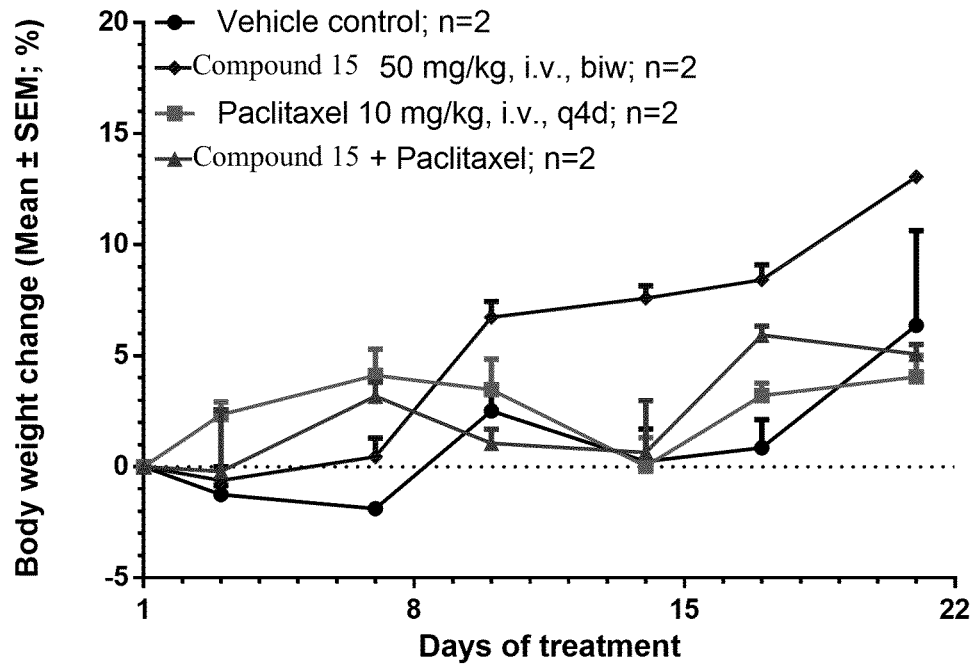
FIG. 10 shows the body weight change of the LU5250 model mice after administration of the following drug combinations: Compound 15+paclitaxel (FIG. 10(a)), Compound 15+irinotecan (FIG. 10(b)).
Figure 10:
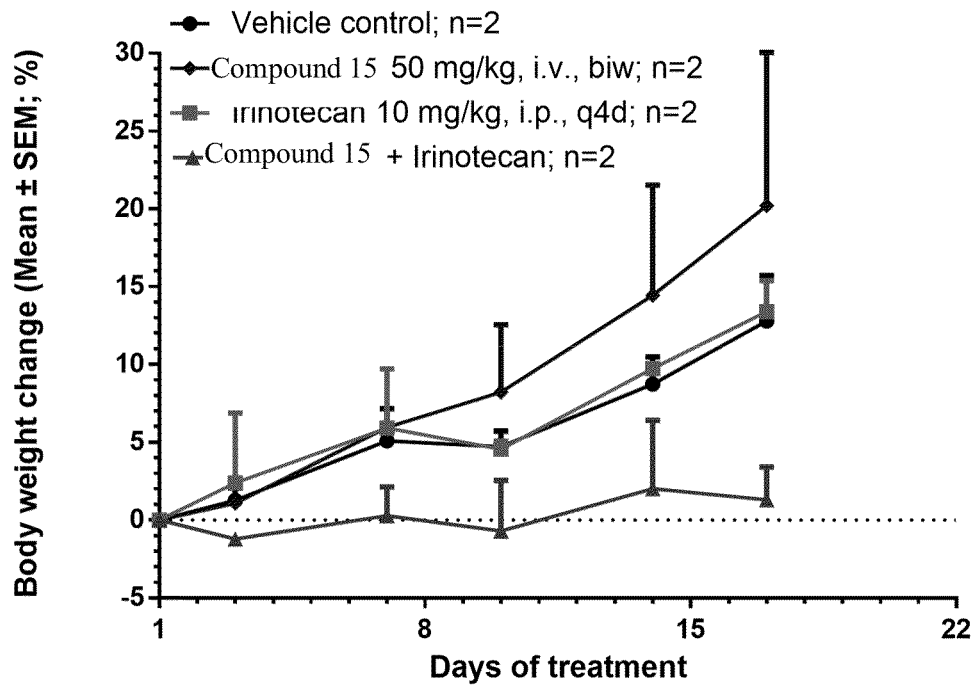
Figure 11:
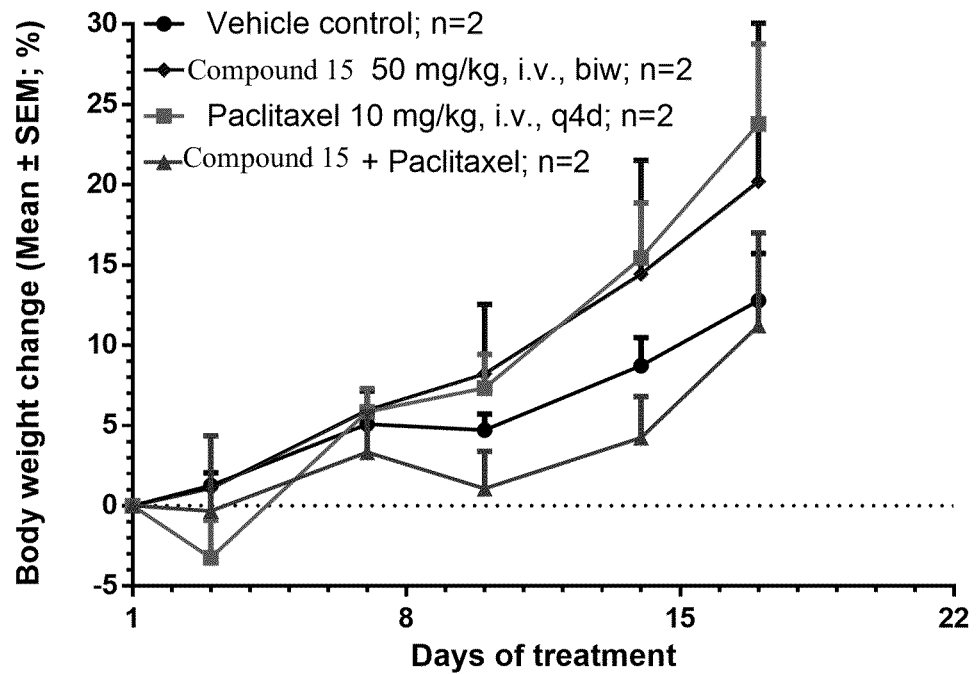
FIG. 11 shows the body weight change of the LU5188 model mice after administration of the following drug combinations: Compound 15+paclitaxel (FIG. 11(a)), Compound 15+irinotecan (FIG. 11(b)).
Figure 11:
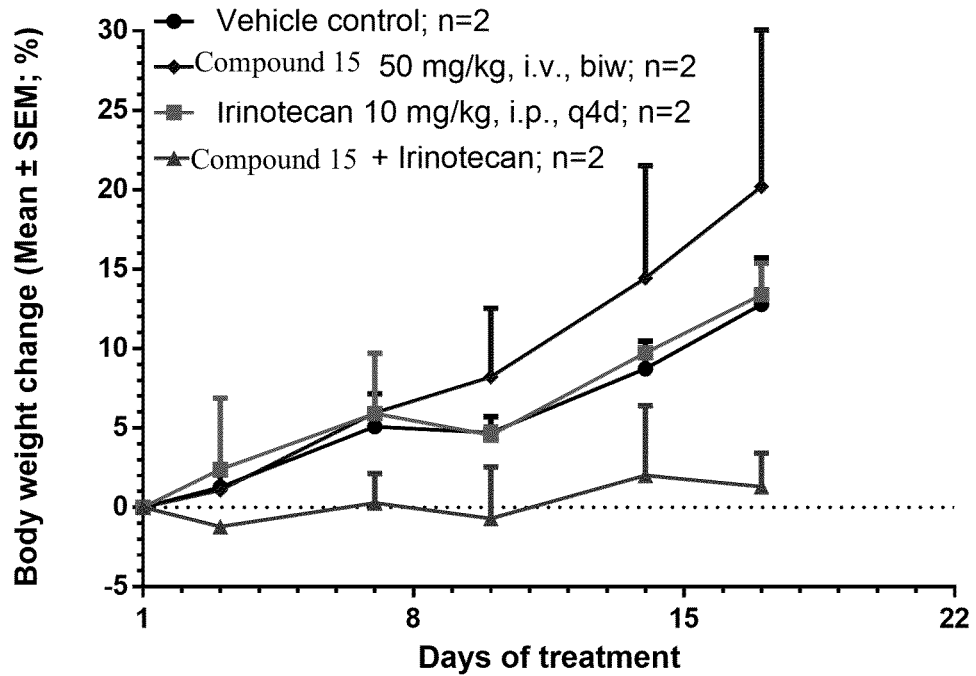

Example 5. Combined Anti-Cancer Effect of Compound 15 in Combination with Irinotecan in Xenograft Model of Mice Bearing Human SW620 Cell Line Colon Cancer This study investigated the anti-cancer therapeutic effect of Compound 15 and irinotecan in the SW620 human colon cancer model. As shown in FIG. 7, Compound 15 (100 mg/kg) enhanced the anti-cancer effect of irinotecan alone. Compound 15 (100 mg/kg) showed a minor anti-cancer effect with T/C (%) of 60.6%; Irinotecan (50 mg/kg) alone also showed a minor anti-cancer effect with T/C (%) of 29.9%; Compound 15 combined with irinotecan in a BIW dosing cycle (50 or 100 mg/kg of Compound 15) and in a QW dosing cycle (100 mg/kg of Compound 15) showed T/C (%) of 23.5% (P=0.0001), 9.1% (P<0.0001) and 11.4% (P=0.0001), respectively. The results of this study indicate that a more significant anti-cancer effect was achieved in prostate cancer when Compound 15 and irinotecan were administered in combination than alone.

As seen from the above studies where Compound 15 was used as a single agent or combined with chemotherapeutic agents for in vitro cell anti-proliferation assay, the inhibition on proliferation in a series of tumor cell lines was enhanced when Compound 15 was combined with chemotherapeutic agents.

The results of the studies, where Compound 15 was combined with chemotherapeutic agents in NCI-H146 human small cell lung cancer model, MDA-MB-231 human triple-negative breast cancer model, PC-3 human prostate cancer model, MGC80-3 human gastric cancer model and SW620 human colon cancer model, showed that Compound 15 can enhance the anti-cancer effect of chemotherapy agents.

These results showed that the combination of Bcl-2/Bcl-xL inhibitors with chemotherapeutic agents had great potential for cancer treatment.

Example 6. Compound 15 for Use in the Treatment of Patients with Metastatic Solid Tumors Compound 15 is a novel dual Bcl-2/Bcl-xL inhibitor. Embodying a unique development strategy, it artfully reduces targeted platelet toxicity while maintaining strong in vivo anti-cancer activity. Compound 15 inhibits tumor growth in a human cancer xenograft model while showing significantly less thrombocytopenia.

Three clinical trials (Phase I or Phase I/II) with similar study designs were conducted in the United States, Australia, and China. During the dose escalation phase, the patient received Compound 15 (10-400 mg) twice weekly or weekly intravenously for a 28-day treatment cycle. Tumor response assessment was performed every 2 cycles according to RECIST 1.1 criteria. The purpose of the study was to assess safety, maximum tolerated dose (MTD)/recommended phase II dose (RP2D), pharmacokinetics (PK), pharmacodynamics (PD), and the preliminary efficacy of Compound 15 as a single agent in metastatic solid tumors.

As of Jan. 31, 2019, 44 patients (US: 21 patients, China: 13 patients, Australia: 10 patients) received treatment with 7 different dose levels of Compound 15. The dose level currently under study is 320 mg twice a week.

A pooled analysis of the study showed that Compound 15 was well tolerated at all tested dose levels. The MTD had not been reached. Most adverse events (AEs) were grade 1 or 2 and no drug-related AEs that caused drug discontinuation were found. The most common grade 3/4 AEs were hyponatremia (11.4%), decreased lymphocyte count (6.8%), and elevated lipase (6.8%).

19 patients with small cell lung cancer (SCLC) underwent at least one post-treatment tumor evaluation, and 1 of the US patient had partial remission (PR) at a dose of 40 mg. The partial remission lasted for a long time and the patient had been treated with Compound 15 for more than 20 courses.

4 Chinese patients achieved stable disease (SD) at a dose of 80 mg/240 mg, and two of them were stable for more than four courses. In addition, 5 cases of stable disease in other tumor types (e.g., CRC) were reported in Australian studies.

PK analysis showed that AUC and Cmax on day 1 increased proportionally with dose in the dose range of 10-160 mg, and AUC and Cmax were comparable between US and Chinese patients at the same dose level.

This study showed that Compound 15 was well tolerated at all tested dose levels. Dose escalation is continued in a twice-weekly and weekly dosing schedule. A preliminary anti-cancer activity of single agent was observed during dose escalation.

Example 7. Therapeutic Efficacy of Compound 15 in Lung Cancer Xenograft Model

The therapeutic efficacy of compound 15 alone and its multiple combinations in the treatment of subcutaneous HuPrime® Lung cancer xenograft model LU5250 and LUS188 in female NOD.SCID mice was evaluated.

Either LUS250 or LU5188 tumor mass with rough size of 3×3×3 mm$^3$ were inoculated into female NOD.SCID mice and the day of randomization was denoted as day 1. The treatment was initiated on day 1 when tumors approximated a mean volume 136 mm$^3$ of LUS250 and 155 mm$^3$ of LU5188, respectively. There were 6 groups enrolled in each model eventually. See Table 3 for the mode of administration and doses. Both models were taken down on day 21.

TABLE 3

| Group | No. | Treatment | Dose level (mg/kg) | Dosing solution (mg/ml) | Dosing volume (μl/g) | Route of dosing | Dosing frequency & duration |
|---|---|---|---|---|---|---|---|
| 1 | 2 | Compound 15 Vehicle | — | — | 10 | i.v. | BIW × 7 doses |
|   |   | Irinotecan Vehicle |   |   | 10 | i.p. | Q4D × 3 w |
| 2 | 2 | Compound 15 | 50 | 5 | 10 | i.v. | BIW × 7 doses |
| 3 | 2 | Irinotecan | 10 | 1 | 10 | i.p. | Q4D × 3 w |
| 4 | 2 | Compound 15 | 50 | 5 | 10 | i.v. | BIW × 7 doses |
|   |   | Irinotecan | 10 | 1 | 10 | i.p. | Q4D × 3 w |
| 5 | 2 | Paclitaxel | 10 | 1 | 10 | i.v. | Q4D × 3 w |
| 6 | 2 | Compound 15 | 50 | 5 | 10 | i.v. | BIW × 7 doses |
|   |   | Paclitaxel | 10 | 1 | 10 | i.v. | Q4D × 3 w |

Note:
a. No.: animal number per group.
b. Dosing Volume was adjusted according to individual body weight (BW).
c. The day of randomization was set as day1. The day of treatment was set as day1.
d. For BIW, treatment was administered on day1, day4, day8, day11, day15, day18 and day21; For Q4D, treatment was administered on day1, day5, day9, day13, day17, day21.
e. For combo, Compound 15 was dosed first, and Irinotecan/ Paclitaxel was administered 1 hour after.
f. If mouse suffered a body weight loss (BWL) >20%, it must be removed and euthanized.

Tumor volumes were measured twice weekly in two dimensions using a caliper, and the volume was expressed in mm$^3$ using the formula: V=0.5 a×b$^2$ where a and b are the long and short perpendicular diameters of the tumor, respectively. Dosing as well as tumor and body weight measurement were conducted in a Laminar Flow Cabinet. Relative tumor volume (RTV) was calculated using the following formula: RTV=Vt/V1 where V1 and Vt are the average tumor volumes on the first day of treatment (day 1) and the average tumor volumes on a certain time point (day t). Synergy Ratio was calculated using the following formula (Clarke R., Breast Cancer Research & Treatment, 1997, 46 (2-3):255-278.7): Synergy Ratio=((A/C)×(B/C))/(AB/C); wherein A is response to treatment A; B is response to treatment B; C is response to vehicle control; AB: response to combination of treatment A and B.

Standard NCI procedures were used to calculate tumor parameters. Relative tumor proliferation rate (% T/C) was calculated as the mean RTV of treated tumors (T) divided by the mean RTV of control tumors (C)×100%. The percentage T/C value is an indication of antitumor effectiveness: a value of T/C<42% is considered significant antitumor activity by the NCI. A T/C value <10% is considered to indicate highly significant antitumor activity, and is the level used by the NCI to justify a clinical trial if toxicity and certain other requirements are met (termed DN-2 level activity). A body weight loss (mean of group) of greater than 20%, or greater than 20% of drug deaths are considered to indicate an excessively toxic dosage.

The tumor growth curves (mean tumor volume over time) of LU5250 and LU5188 are shown in FIGS. 8(a), 8(b), 9(a) and 9(b), respectively. The tumor growth inhibition is summarized in Table 4 and Table 5 below. The results of mean body weight changes of LU5250 and LU5188 are shown in FIGS. 10(a), 10(b), 11(a) and 11(b), respectively.

TABLE 4

Antitumor activity of Compound 15 combined with Paclitaxel or Irinotecan in SCLC patient-derived xenograft LU5250

| Group | Treatment | RTV @ day21 | T/C (%) @ day21 | Synergy Ratio @ day21 |
|---|---|---|---|---|
| 1 | vehicle | 7.13 ± 0.78 | — | — |
| 2 | Compound 15 | 9.75 ± 3.77 | 136.8 | — |
| 3 | Irinotecan | 1.92 ± 0.24 | 26.9 | — |
| 4 | Compound 15 + Irinotecan | 1.60 ± 0.24 | 22.5 | 1.63 |
| 5 | Paclitaxel | 2.33 ± 0.13 | 32.6 | — |
| 6 | Compound 15 + Paclitaxel | 1.71 ± 0.43 | 24.0 | 1.86 |

Ratio > 1, synergistic; ratio = 1, additive; ratio < 1, antagonistic

Note:
1, Relative tumor volume (RTV): mean ± SEM.
2, Relative tumor proliferation rate (% T/C) = mean RTV of treated tumors (T$_{RTV}$)/mean RTV of control tumors (C$_{RTV}$) × 100%

TABLE 5

Antitumor activity of Compound 15 combined with Paclitaxel or Irinotecan in SCLC patient-derived xenograft LU5188

| Group | Treatment | RTV @ day21 | T/C (%) @ day21 | Synergy Ratio @ day21 |
|---|---|---|---|---|
| 1 | vehicle | 13.60 ± 1.70 | — | — |
| 2 | Compound 15 | 17.05 ± 6.59 | 125.4 | — |
| 3 | Irinotecan | 8.41 ± 2.49 | 61.8 | — |
| 4 | Compound 15 + Irinotecan | 7.47 ± 1.33 | 55.0 | 1.41 |

TABLE 5-continued

Antitumor activity of Compound 15 combined with
Paclitaxel or Irinotecan in SCLC patient-derived xenograft LU5188

| Group | Treatment | RTV @ day21 | T/C (%) @ day21 | Synergy Ratio @ day21 |
|---|---|---|---|---|
| 5 | Paclitaxel | 20.55 ± 3.20 | 151.1 | — |
| 6 | Compound 15 + Paclitaxel | 8.78 ± 0.50 | 64.6 | 2.94 |

Ratio > 1, synergistic; ratio = 1, additive; ratio < 1, antagonistic

Note:
1, Relative tumor volume (RTV): mean ± SEM.
2, Relative tumor proliferation rate (% T/C) = mean RTV of treated tumors ($T_{RTV}$)/mean RTV of control tumors ($C_{RTV}$) × 100%

Example 8. Therapeutic Efficacy of Compound 15 in Lung Cancer Xenograft Model The therapeutic efficacy of compound 15 alone and in multiple combinations in the treatment of subcutaneous NCI-H146 lung cancer xenograft model was evaluated.

$1 \times 10^7$ NCI-H146 tumor cells were pre-treated in 0.1 mL of phosphate buffer and Matrigel (7:3) and inoculated into female SCID mice. The day of randomization was denoted as day 1. The treatment was initiated on day 1. The study was conducted in 8 groups of mice. See Table 6 for the mode of administration and doses. The entire study was taken down on day 21. The study was conducted in 40 mice. All the animals were randomized into 8 experimental groups. Tumors approximated a mean volume 192 mm³ at randomization.

TABLE 6

| Group | No. | Treatment | Dose level (mg/kg) | Dosing solution (mg/ml) | Dosing volume (μL/g) | Route of dosing | Dosing frequency & duration |
|---|---|---|---|---|---|---|---|
| 1 | 5 | Vehicle | — | — | 10 (Compound 15 vehicle) | i.v. | BIW × 7 doses |
| | | | | | 10 (Paclitaxel vehicle) | i.v. | QW × 3 wks |
| 2 | 5 | Compound 15 | 20 | 2 | 10 | i.v. | BIW × 7 doses |
| 3 | 5 | Irinotecan | 5 | 0.5 | 10 | i.p. | QW × 3 wks |
| 4 | 5 | Paclitaxel | 10 | 1 | 10 | i.v. | QW × 3 wks |
| 5 | 5 | Cisplatin | 1 | 0.1 | 10 | i.p. | Q4D × 3 wks |
| 6 | 5 | Compound 15 | 20 | 2 | 10 | i.v. | BIW × 7 doses |
| | | Paclitaxel | 10 | 1 | 10 | i.v. | QW × 3 wks |
| 7 | 5 | Compound 15 | 20 | 2 | 10 | i.v. | BIW × 7 doses |
| | | Irinotecan | 5 | 0.5 | 10 | i.p. | QW × 3 wks |
| 8 | 5 | Compound 15 | 20 | 2 | 10 | i.v. | BIW × 7 doses |
| | | Cisplatin | 1 | 0.1 | 10 | i.p. | Q4D × 3 wks |

Note:
a. No.: animal number per group.
b. Dosing Volume was adjusted according to individual BW.
c. The day of randomization was set as day1. The day of treatment was set as day1.
d. For BIW, treatment was administered on day1, day4, day8, day11, day15, day18 and day21; For Q4D, treatment was administered on day1, day5, day9, day13 and day17. For QW, on day1, day8 and day15.
e. For combination, in group 6/7/8, Compound 15 was dosed first, and Paclitaxel/Irinotecan/Cisplatin was administered 1 hour after.

Figure 12:
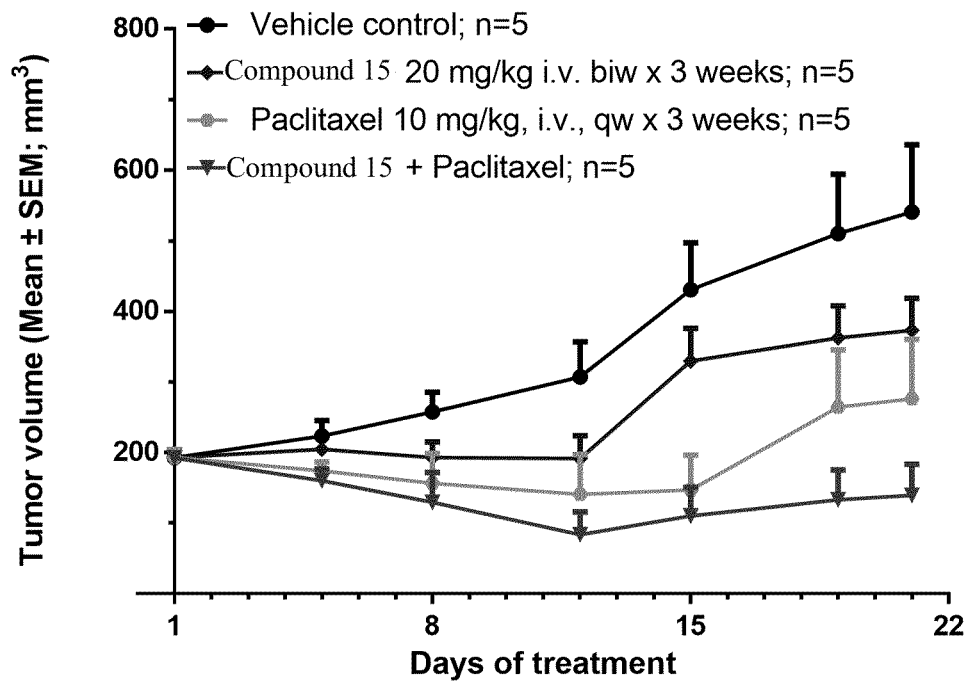
FIG. 12 shows the combination therapy of Compound 15 and paclitaxel (FIG. 12(a)), Compound 15 and irinotecan (FIG. 12(b)) or Compound 15 and cisplatin (FIG. 12(c)) in a subcutaneous human NCI-H146 small cell lung cancer model.
Figure 12:
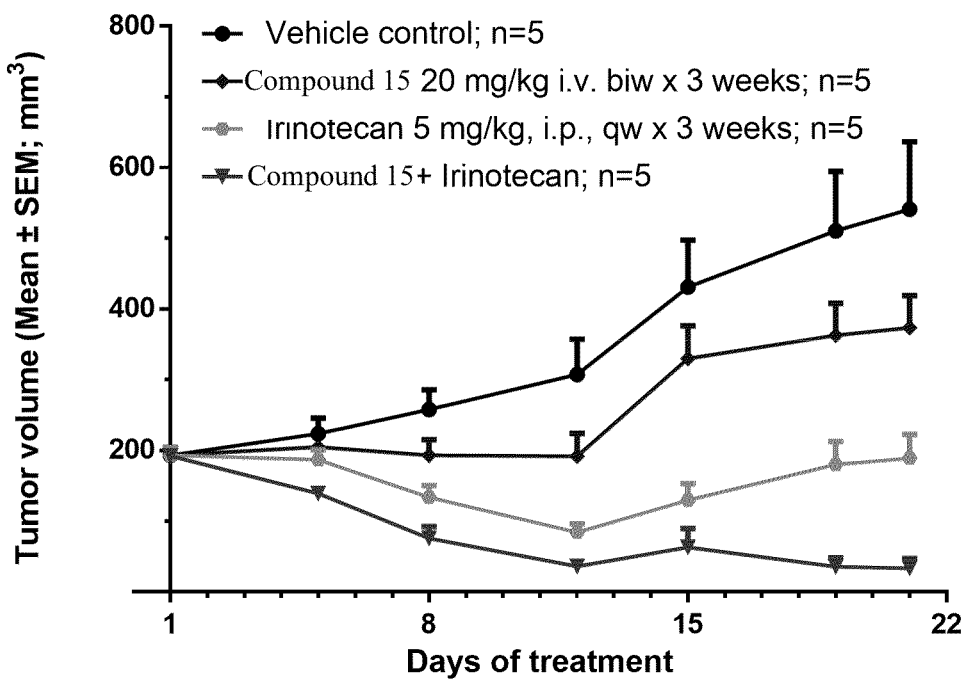
Figure 12:
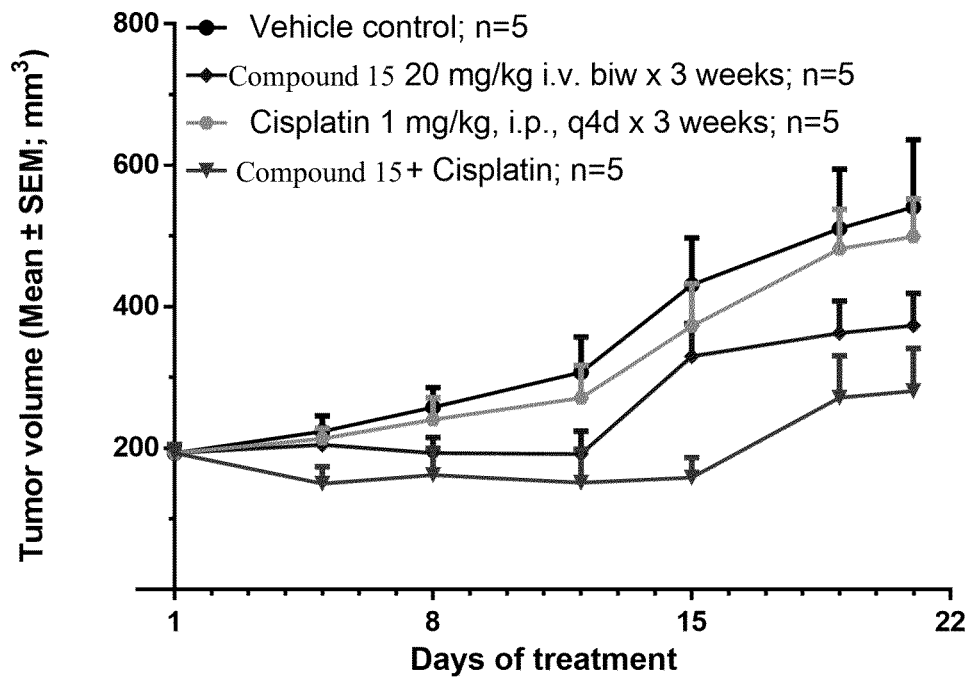
Figure 13:
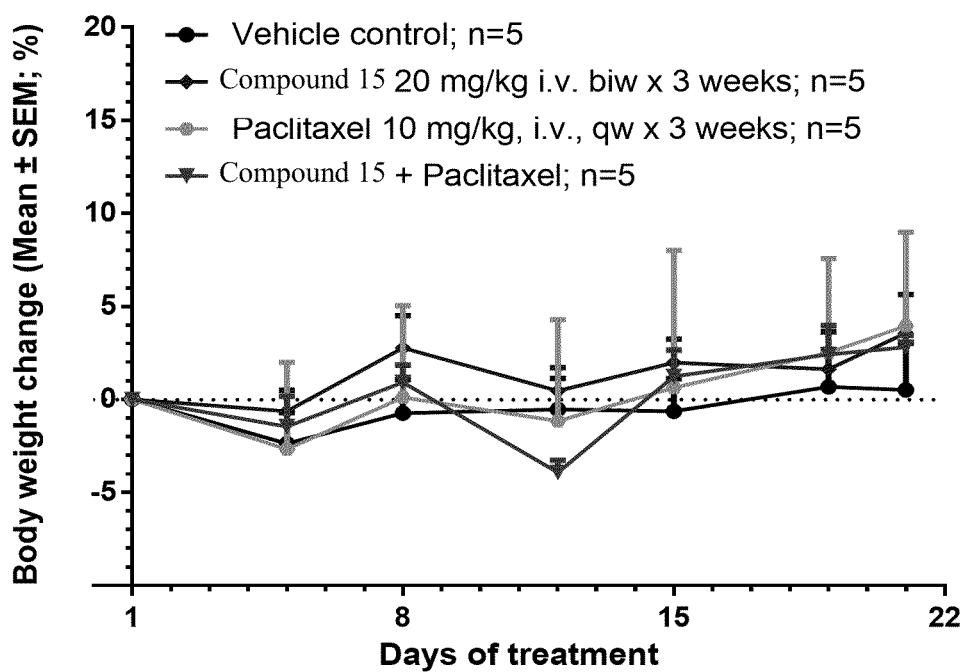
FIG. 13 shows the mean body weight change of mice models obtained by inoculation of subcutaneous human NCI-H146 small cell lung cancer cells, in response to administration of the following combination therapies: Compound 15+paclitaxel (FIG. 13(a)), Compound 15+irinotecan (FIG. 13(b)) and Compound 15+cisplatin (FIG. 13(c)).
Figure 13:
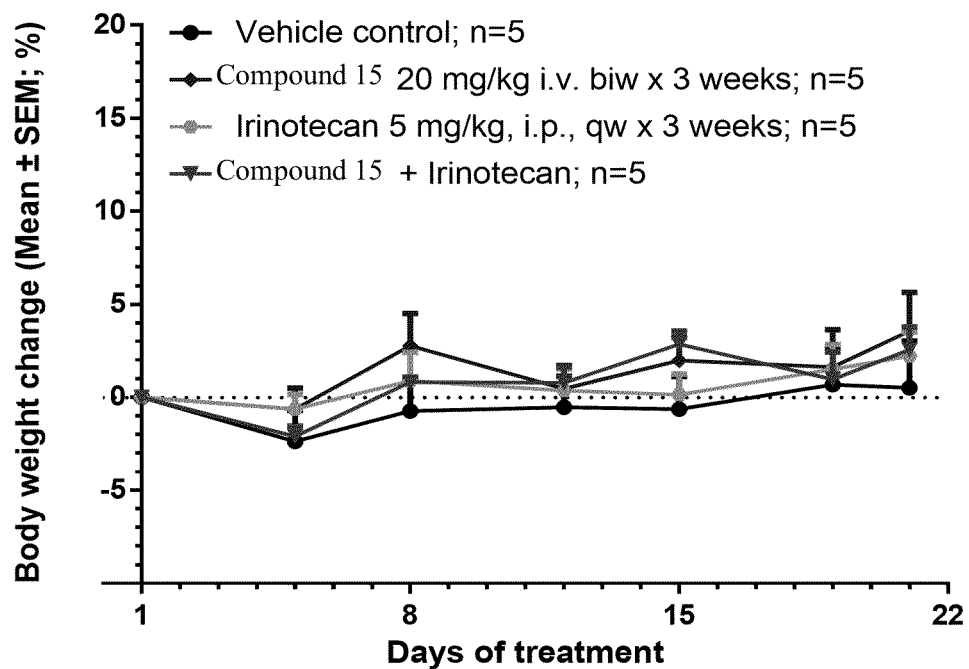
Figure 13:
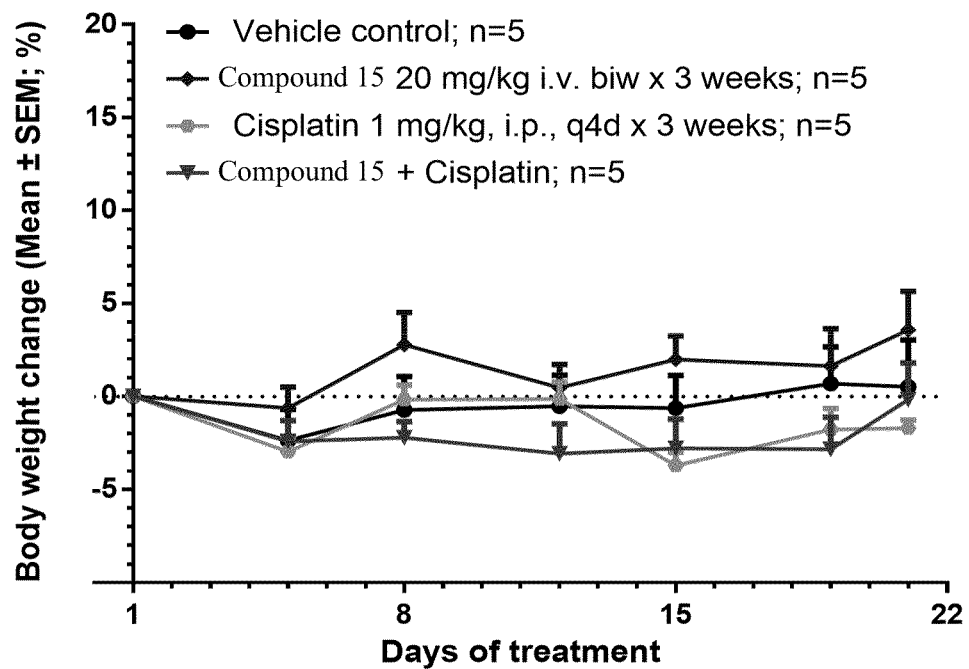
Figure 14:
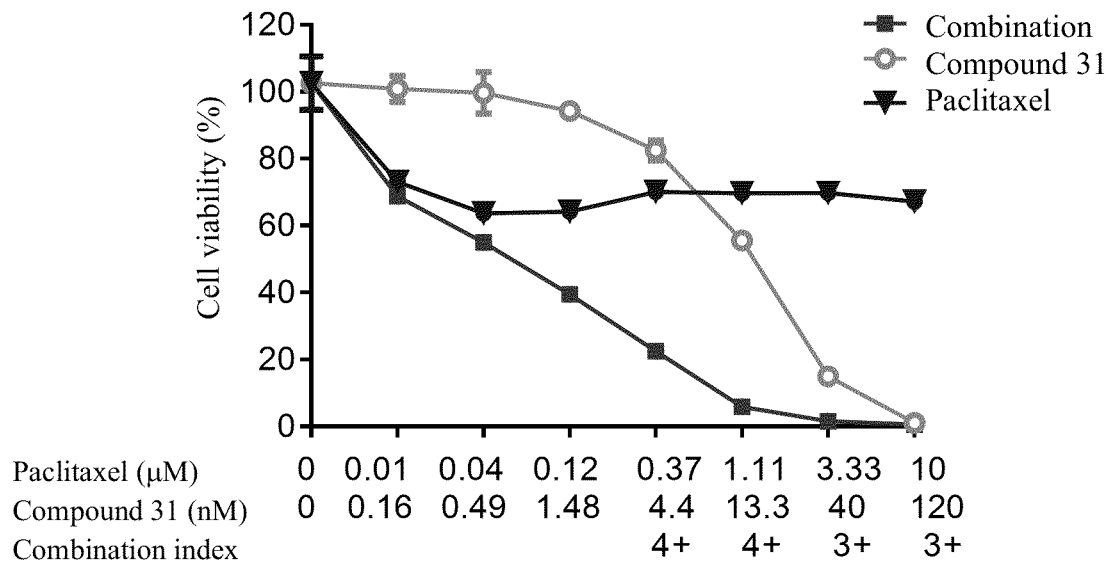
FIG. 14 shows the anti-proliferative effect of Compound 31 in combination with paclitaxel in human small cell lung cancer cell line NCI-H146 (FIG. 14(a)), NCI-H69 (FIG. 14(b)), NCI-H446 (FIG. 14(c)).
Figure 14:
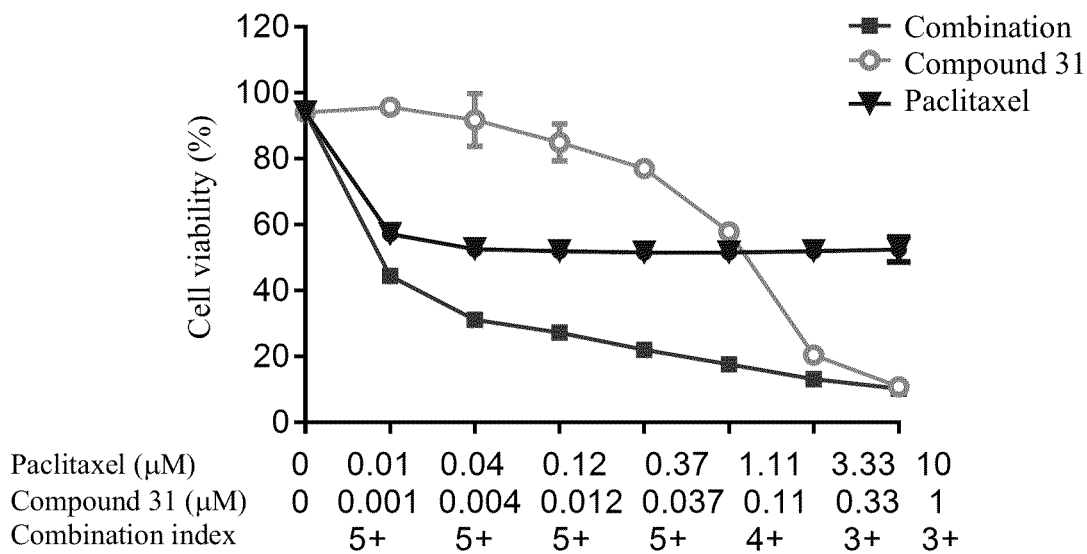
Figure 14:
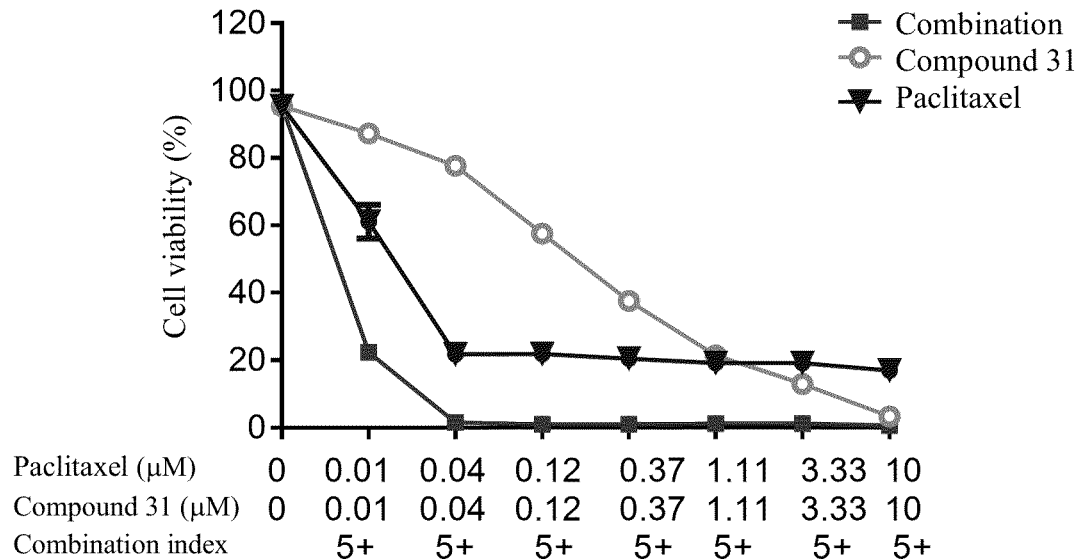
Figure 15:
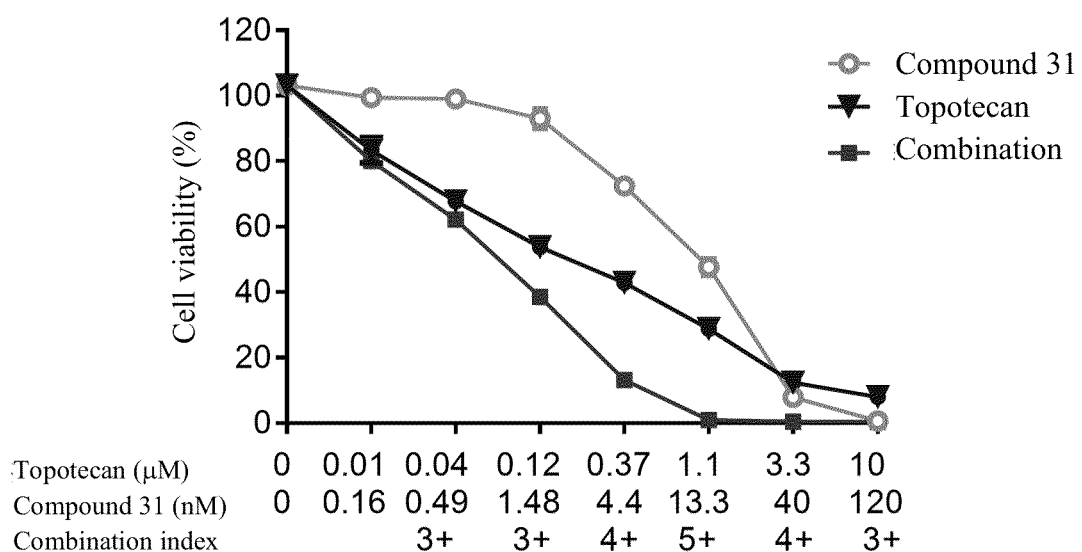
FIG. 15 shows the anti-proliferative effect of Compound 31 in combination with topotecan in human small cell lung cancer cell line NCI-H146 (FIG. 15(a)), NCI-H69 (FIG. 15(b)), NCI-H446 (FIG. 15(c)).
Figure 15:
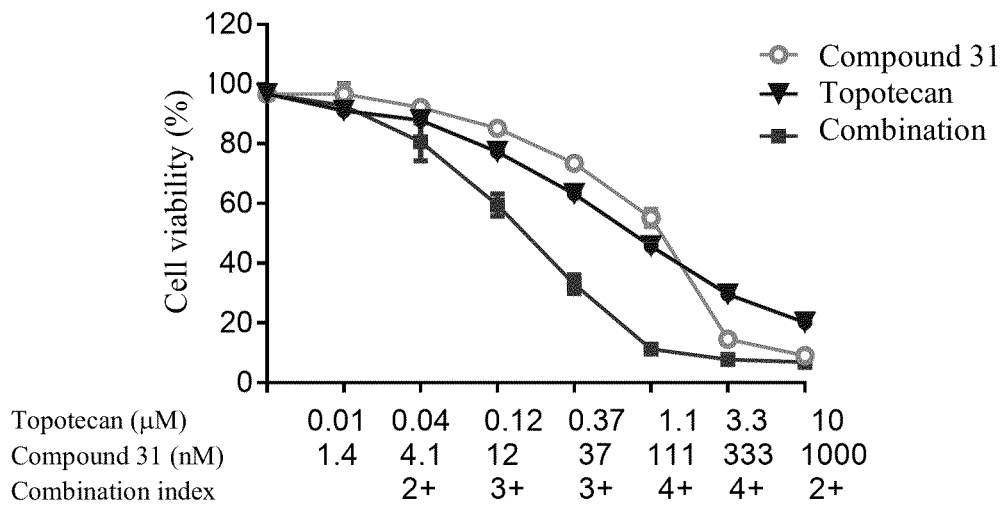
Figure 15:
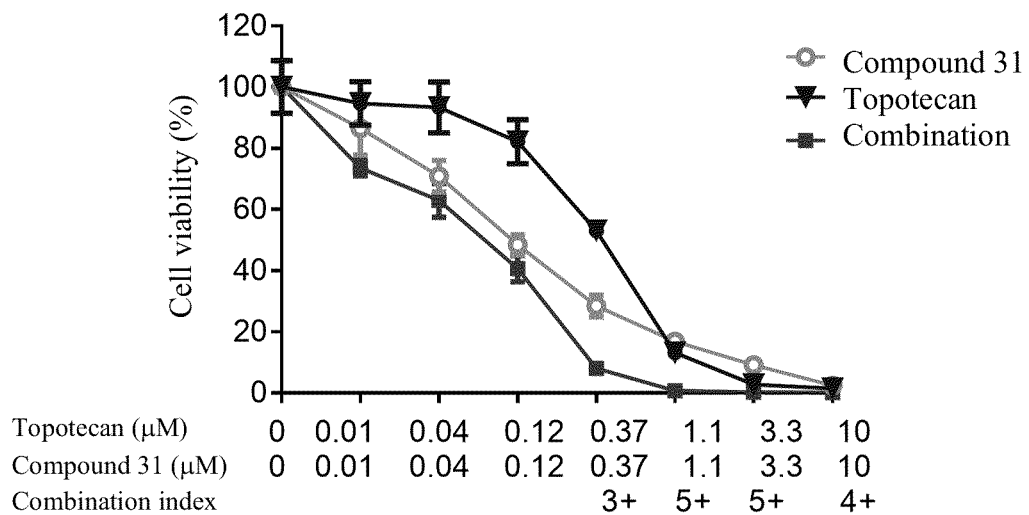
Figure 16:
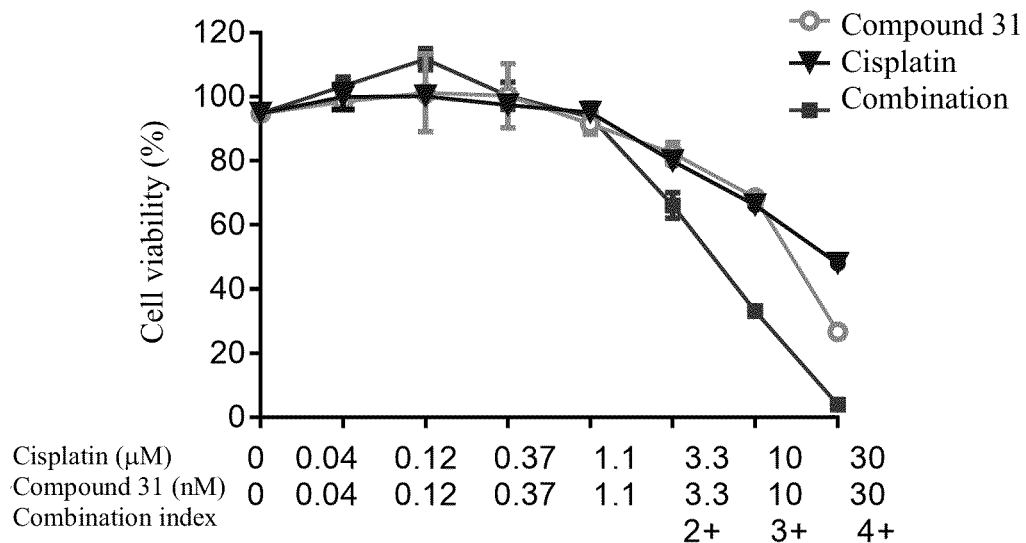
FIG. 16 shows the anti-proliferative effect of Compound 31 in combination with cisplatin in human small cell lung cancer cell line NCI-H146 (FIG. 16(a)), NCI-H69 (FIG. 16(b)).
Figure 16:
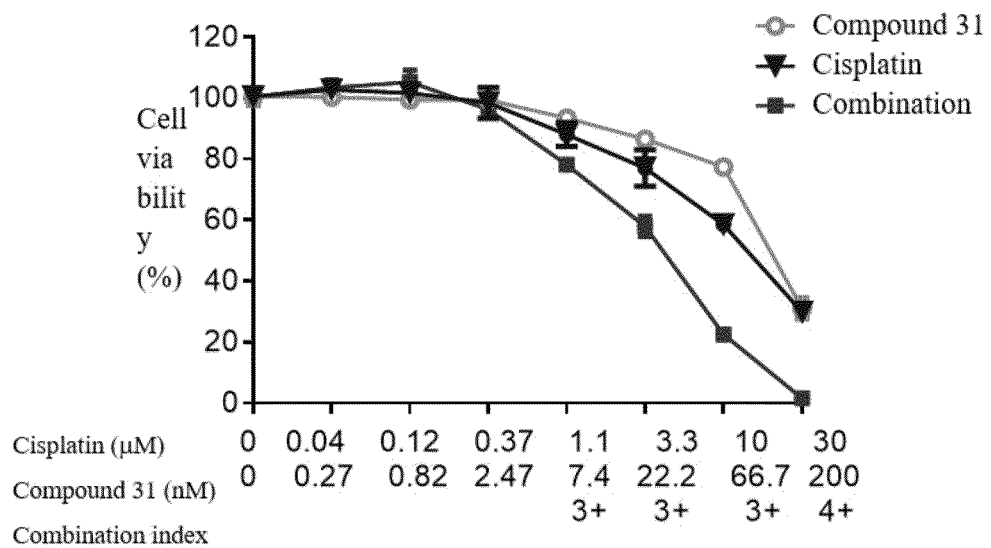
Figure 17:
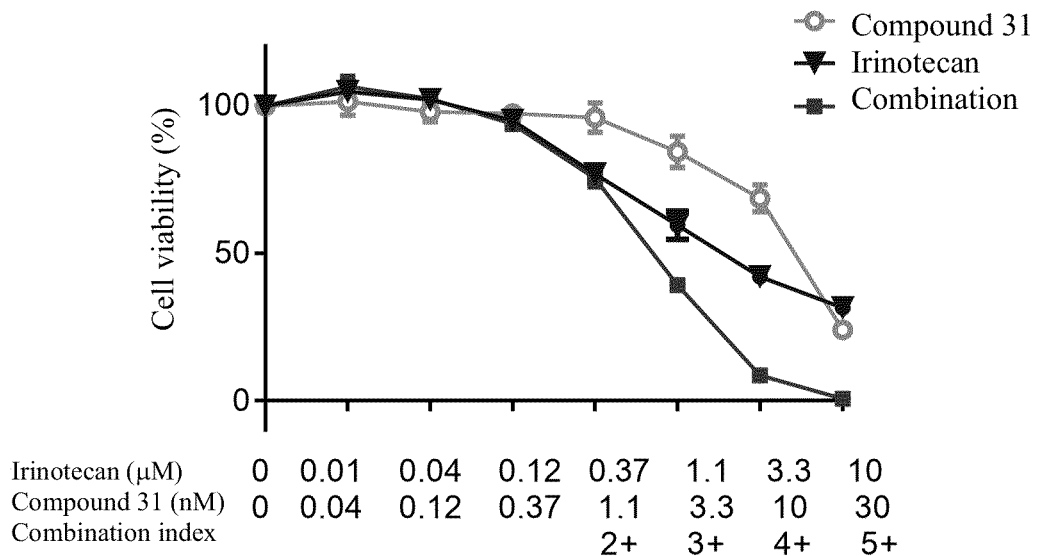
FIG. 17 shows the anti-proliferative effect of Compound 31 in combination with irinotecan in human small cell lung cancer cell line NCI-H146 (FIG. 17(a)), NCI-H69 (FIG. 17(b)).
Figure 17:
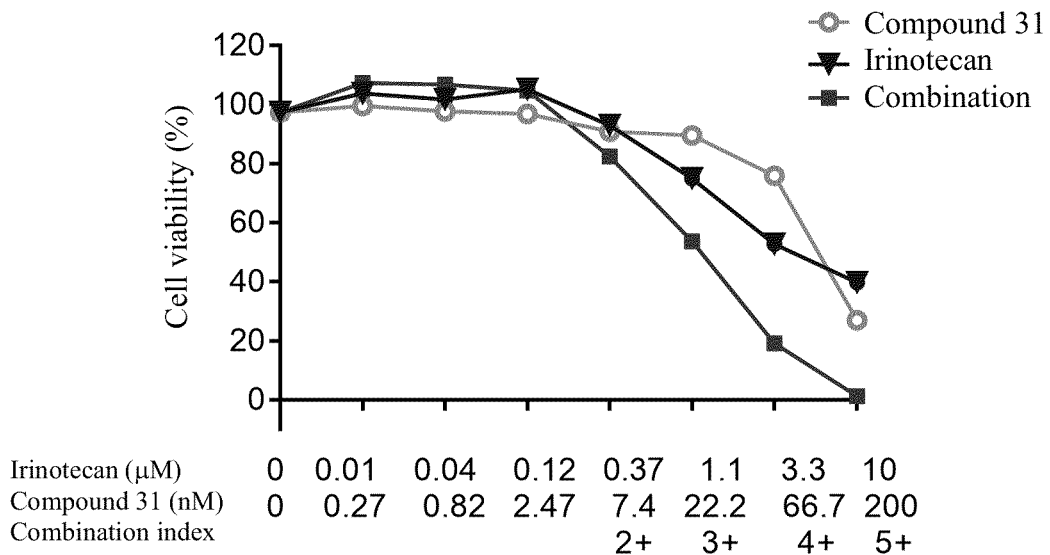
Figure 18:
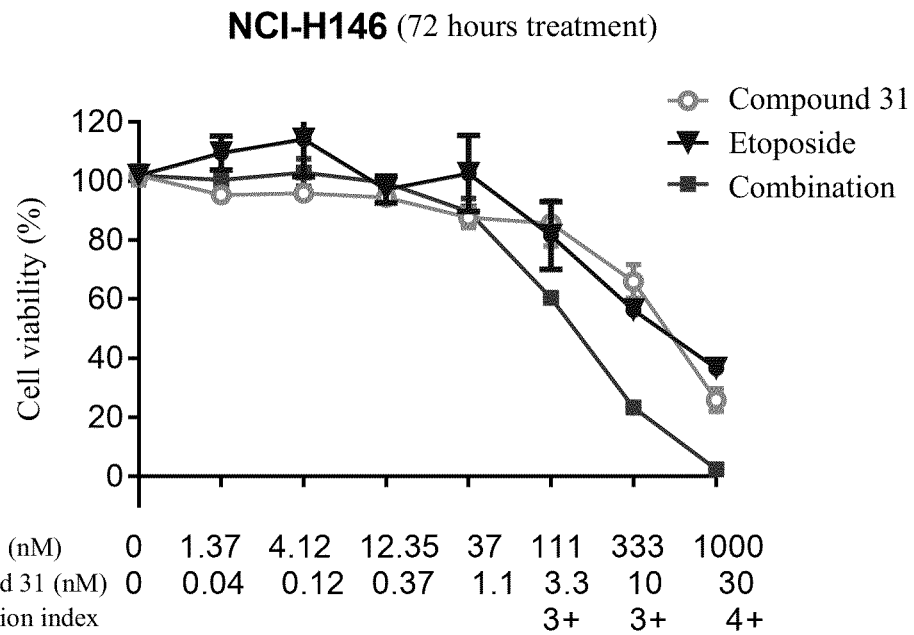
FIG. 18 shows the anti-proliferative effect of Compound 31 in combination with etoposide in human small cell lung cancer cell line NCI-H146 (FIG. 18(a)), NCI-H69 (FIG. 18(b)).
Figure 18:
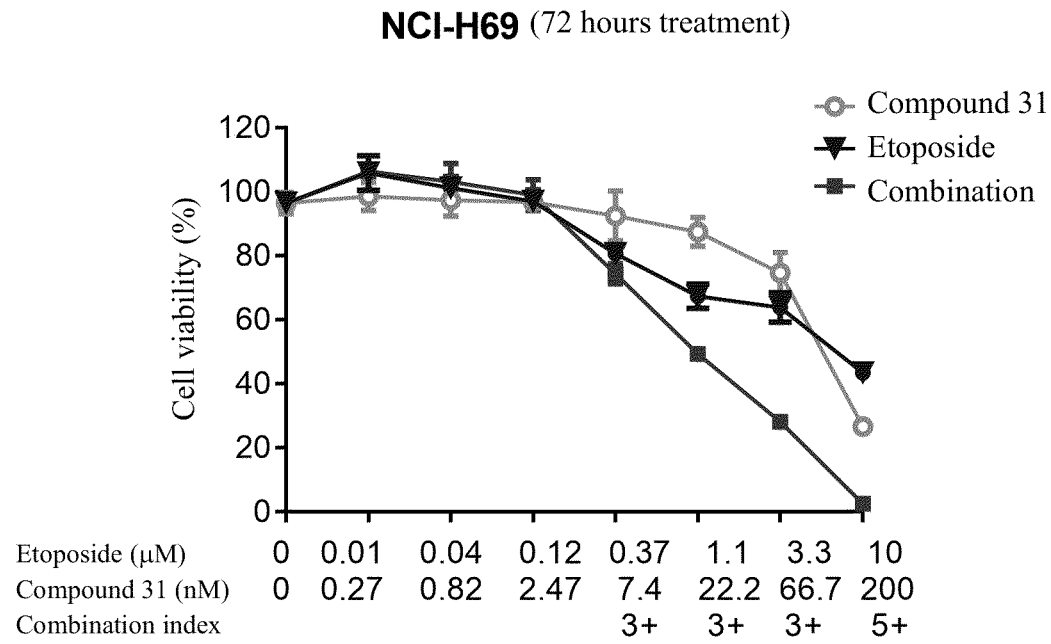
Figure 19:
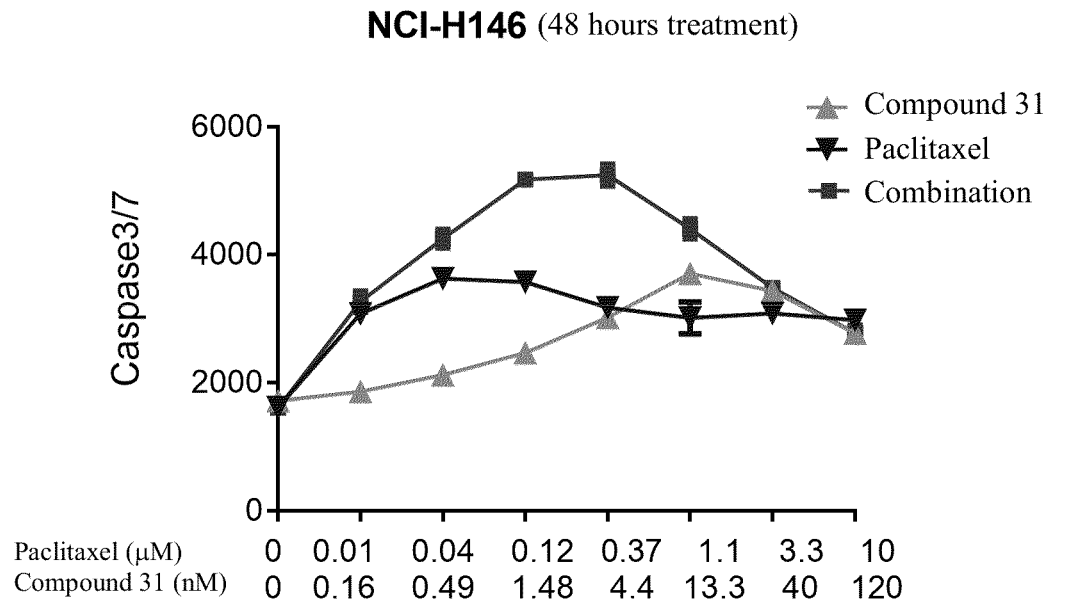
FIG. 19 shows that caspase 3/7 activity increases in the human small cell lung cancer cell line NCI-H146 treated with Compound 31 in combination with paclitaxel.
Figure 20:
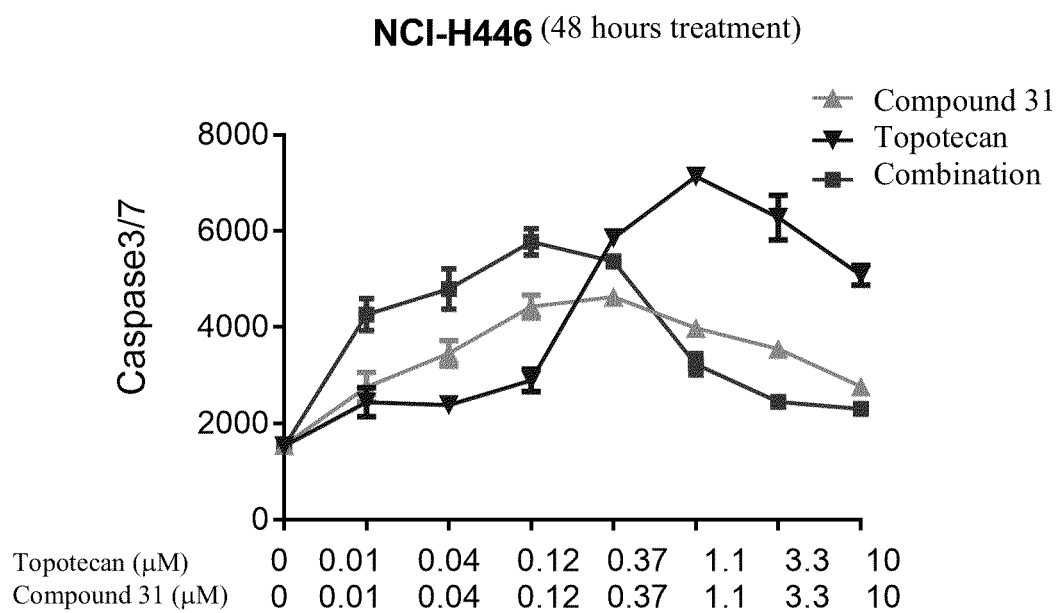
FIG. 20 shows that caspase 3/7 activity increases in the human small cell lung cancer cell line NCI-H446 treated with Compound 31 in combination with topotecan.

The method of measuring and calculating tumor volume, and the method of calculating tumor parameters are the same as those in Example 7. The tumor growth curves (mean tumor volume over time) of 8 different groups are shown in FIGS. 12(a), 12(b) and 12(c). The tumor growth inhibition is summarized in Table 7 below. The results of mean body weight changes in the tumor bearing mice are shown in FIGS. 13(a), 13(b) and 13(c).

TABLE 7

Antitumor activity in the treatment of NCI-H146 model

| Group | Treatment | RTV @day 21 | T/C (%) @ day 21 | Synergy Ratio @day 21 | mRECIST_best | mRECIST_last |
|---|---|---|---|---|---|---|
| 1 | Vehicle | 2.9 ± 0.5 | — | — | 2/5 SD, 3/5 PD | 5/5 PD |
| 2 | Compound 15 | 2.0 ± 0.3 | 70.0 | — | 4/5 SD, 1/5 PD | 1/5 SD, 4/5 PD |
| 3 | Irinotecan | 1.0 ± 0.2***## | 34.4 | — | 3/5 PR, 2/5 SD | 1/5 PR, 3/5 SD, 1/5 PD |
| 4 | Compound 15 + Irinotecan | 0.2 ± 0.1*** | 5.7 | 4.2 | 4/5 PR, 1/5 CR | 4/5 PR, 1/5 CR |
| 5 | Paclitaxel | 1.4 ± 0.4** | 48.4 | — | 3/5 PR, 2/5 SD | 3/5 SD, 2/5 PD |
| 6 | Compound 15 + Paclitaxel | 0.8 ± 0.3*** | 27.1 | 1.2 | 3/5 PR, 2/5 SD | 1/5 PR, 3/5 SD, 1/5 PD |

TABLE 7-continued

Antitumor activity in the treatment of NCI-H146 model

| Group | Treatment | RTV @day 21 | T/C (%) @ day 21 | Synergy Ratio @day 21 | mRECIST_best | mRECIST_last |
|---|---|---|---|---|---|---|
| 7 | Cisplatin | 2.6 ± 0.2 | 90.2 | — | 2/5 SD, 3/5 PD | 5/5 PD |
| 8 | Compound 15 + Cisplatin | 1.4 ± 0.2* | 49.5 | 1.3 | 1/5 PR, 4/5 SD | 4/5 SD, 1/5 PD |

*p < 0.05,
***p < 0.001 vs. vehicle control group;
p < 0.01 vs. Compound 15;
Ratio > 1, synergistic;
ratio = 1, additive;
ratio < 1, antagonistic
Note
1, mRECIST (Gao H, Nature medicine, 2015, 21(11): 1318): modified Response Evaluation Criteria in Solid Tumors; mRECIST_best: the best response during the treatment; mRECIST_last: response on the last day of treatment.
2, PR: partial response, CR: complete response, SD: stable disease, PD: progressive disease

Example 9. In Vitro Study of Compound 31 in Small Cell Lung Cancer Cell Line Model The study was to test the anti-proliferation and apoptosis-inducing effects of Compound 31 in combination with chemotherapy agents for small cell lung cancer in human small cell lung cancer cells. Chemotherapeutic agents used in this study included paclitaxel, cisplatin, etoposide, irinotecan, and topotecan.

The Cell Titer-Glo® luminescent cell viability assay (CTG) and Caspase-Glo® 3/7 assay were used to assess the effects of Compound 31 as a single agent or in combination with other chemotherapeutic agents against proliferation and in induction of apoptosis, respectively.

Cells in the logarithmic growth phase were collected for Cell Titer-Glo® (CTG) luminescence cell viability assay. 10 µL of the diluted drug solution was added into a 96-well plate while 10 µL of the medium was added into the 96-well control plate. For the study of the combination, 5 µL of the indicated test reagent was added to each well. At the end of the study, the 96-well plates were equilibrated to room temperature, and then 30 µL of CTG reagent (protected from light) was added to each well to induce cell lysis. The luminescent signal was then detected using a Biotek Synergy H1 plate reader. Percent cell viability (%) was calculated using the mean luminescence value (LN) of the replicate wells (blank) of the control group, according to the following formula:

percent cell viability (%)=(fluorescence signal value of experimental cells−fluorescence signal value of negative control cell)/(fluorescence signal value of control cells−fluorescence signal value of negative control cells)×100%.

Cell viability curve was plotted using Graphpad Prism 6.0 software (Golden software, Golden, Colorado, USA). For the study of the drug combination, the Combination Index (CI) was calculated using CalcuSyn software (BIOSOFT, UK) to further analyze the combined effects of the indicated drugs (Chou, Cancer Research 70, 440-446.). CalcuSyn is a professional analysis software for mixed drug treatment. It can quickly and accurately calculate various drug interactions, including synergistic effect, additive effect and antagonistic effect. If the CI value of two drugs is <1, it indicates that the two drugs have a synergistic effect; if the CI value=1, it indicates that the two drugs have an additive effect; if the CI value is >1, it indicates that the two drugs have an antagonistic effects.

The assay kit (Promega) in the Caspase-Glo® 3/7 assay was used to quantify the activation of caspase 3/7 during the apoptosis induced by the drugs or their combinations. The cell seeding and drug dilution procedures are the same as those described above. Cells in 96-well plates were treated with the drugs or their combinations and then held at room temperature for 30 minutes after equilibration. 30 µL of Caspase-Glo® 3/7 reagent (protected from light) was added to each well and mixed thoroughly to induce cell lysis. The 96-well plate was held at room temperature for an additional 30 minutes to stabilize the luminescent signal. Luminescence signals were detected using a Biotek Synergy H1 plate reader. The caspase 3/7 activation curve was plotted using Graphpad Prism 6.0 software 4.

Small cell lung cancer cell lines were available from the following sources: (1) ATCC accession No. HTB-119 (NCI H69); (2) Shanghai Institute of Biochemistry and Cell Biology (NCI-H446 and NCI-H146). Cells were cultured at 37° C. in a humidified environment containing 5% $CO_2$.

The purpose of this study was to evaluate the effect of Compound 31 as a single agent or in combination with other chemotherapy agents (including paclitaxel, cisplatin, etoposide, irinotecan and topotecan) in inhibiting cell proliferation/viability in small cell lung cancer cell line NCI-H146, NCI-H69 and NCI-H446. As shown in FIGS. 14, 15, 16, 17 and 18, the combination of Compound 31 with paclitaxel, cisplatin, etoposide, irinotecan or topotecan has a much greater effect on tumor growth inhibition than Compound 31 alone or the corresponding chemotherapy agent alone, which can be seen from its response curve shifting to the left.

The combination index (CI) can be further calculated based on the different doses of the combinations specified in FIGS. 14, 15, 16, 17, and 18. In all cell lines tested, the combination of Compound 31 with paclitaxel or topotecan achieved synergy at lower concentrations, whereas synergy was observed with Compound 31 in combination with cisplatin, irinotecan or etoposide at higher concentration.

The results confirmed that in human small cell lung cancer cell line, the combination of Compound 31 with a chemotherapeutic agent can produce a synergistic antiproliferative effect. The original dose-dependent growth inhibition curves and combination index are shown in FIGS. 14, 15, 16, 17 and 18.

The inventors next tested the effect of Compound 31 as a single agent or in combination with other chemotherapeutic drugs on induction of apoptosis by measuring caspase 3/7 activation.

The results of the study showed (see FIGS. 19, 20, 21, 22, and 23) that in all cell lines and tested drugs, the drug treatment increased the concentration of activated (lysed) Caspase 3/7 in a dose-dependent manner. The drug combination obtained a significantly higher concentration than the single agent, indicating that the drug combination can induce apoptosis more effectively. Interestingly, in some cases, caspase 3/7 activation is divided into two phases. After an increase in the initial phase (increased by a stronger intensity in the combination group), the activated caspase 3/7 concentration reached a plateau and began to decline in the later phase. This two-phase activation of caspase 3/7 is more pronounced in the drug combination group and occurs more rapidly. This is in line with the principle that combination of drugs triggers more effective and faster apoptosis.

Discussion

In an in vitro study of small cell lung cancer cell line model, we combined Compound 15 with standard chemotherapy drugs for small cell lung cancer, including paclitaxel, topotecan, cisplatin, etoposide, and irinotecan. These chemotherapies kill cancer cells by inhibiting mitosis (paclitaxel) or adding genotoxicity (other drugs) to cells, thereby down-regulating anti-apoptotic proteins (e.g., Mcl-1 is inhibited by paclitaxel during mitosis (Huang S, et al. Oncotarget), 7(25))) or up-regulating pro-apoptotic proteins (e.g., NOXA is inhibited by the topoisomerase 1 inhibitor irinotecan (Okumura K J, et al. Cancer Research, 14 (24))). Compound 15 has a unique mechanism of action. It can target intrinsically overexpressed anti-apoptotic proteins while also overcoming potential resistance from standard chemotherapy, including up-regulation of Bcl-2, Bcl-xL or Bcl-W (Shi J et al. Cancer Research 71 (13); Bah N et al. Cell Death and Discase, 5, e1291; doi: 10.1038/cddis.2014.251.; Huang S, et al. Oncotarget, 7(25)).

The study shows that Compound 31 as a single agent can inhibit proliferation of small cell lung cancer cells. Apoptosis is induced by inducing activation of caspase 3/7. The combination of Compound 15 with other chemotherapeutic drugs can synergistically enhance inhibition and may have stronger anti-tumor activity in vivo. Therefore, the combinations of Compound 31 with standard chemotherapeutic drugs have great therapeutic potential for small cell lung cancer and warrant further clinical trials.

Example 10. Compound 15 for Patients with EGFR Inhibitor Resistance

The therapeutic effect of Compound 15 in combination with cisplatin or docetaxel on the subcutaneous NCI-H1975-L858R-T790M-C797S NSCLC xenograft model was evaluated.

Osimertinib (AZD9291) is a 3rd generation EGFR inhibitor developed to overcome resistance arising from earlier tyrosine kinase inhibitors (TKIs) therapies, typically associated with the occurrence of T790M mutation. However, most patients experience disease progression after 1-2 years on the targeted therapy due to de novo genomic abnormality, such as C797S mutation or exon 20 insertion in EGFR gene. How to kill these newly acquired resistance cells becomes an emergent challenge in the clinic (Nagano, 2018, "Mechanism of Resistance to Epidermal Growth Factor Receptor-Tyrosine Kinase Inhibitors and a Potential Treatment Strategy", Cell 15; 7 (11).pii E212).

The study tested if the combination of chemotherapies and Compound 15 was effective in osimertinib resistant H1975 EGFR C797S xenograft. The combination showed a synergistic inhibition in tumor progression in H1975 CDX model carrying EGFR L858R/T790M/C797S mutations.

6 groups of NOD/SCID mice bearing NCI-H1975 (EGFR L858R/T790M/C797S) tumors were treated with vehicle, Compound 15, docetaxel (TXT), cisplatin, Compound 15 in combination with docetaxel or Compound 15 combination with cisplatin. Compound 15 was administered intravenously at a dose of 100 mg/kg twice a week for a total of 5 doses. Cisplatin was administered intravenously at a dose of 5 mg/kg once a week for a total of 3 doses. Docetaxel was administered intravenously at a dose of 8 mg/kg once a week for a total of 2 doses. When administered in combination, the drugs are each administered at the doses and frequency of administration when administered alone. The treatment with TXT as the single agent showed antitumor activity with T/C value of 21.4% at day 22. The combination treatment of Compound 15 and docetaxel achieved substantial antitumor activity with T/C value of 5.3%. Synergy Ratio calculated as 2.53 (>1) indicates a synergistic combination effect. The treatment with cisplatin as the single agent showed moderate antitumor activity with T/C value of 66.1% at day 22. The combination treatment of Compound 15 and cisplatin achieved synergistic antitumor activity with T/C value of 26.8%, and Synergy Ratio was 1.55 (>1). The method of measuring and calculating tumor volume, and the method of calculating tumor parameters are the same as those in Example 7. The tumor growth curves (mean tumor volume over time) of different groups are shown in FIGS. 24(a) and 24(b).

TABLE 8

Antitumor activity of the treatment in the NCI-H1975-L858R-T790M-C797S model

| Treatment | RTV @ D22 | T/C @ D22 | Synergy ratio @ D22 | RTV @ D29 | T/C @ D29 | Synergy ratio @ D29 | mRECIST_best | mRECIST @ D29 |
|---|---|---|---|---|---|---|---|---|
| Vehicle control | 5.6 ± 0.6 | — | — | 9.0 ± 1.3 | — | — | 5/5 PD | 5/5 PD |
| Compound 15 | 3.4 ± 0.6 | 0.590 | — | 5.7 ± 1.7 | 0.630 | — | 5/5 PD | 5/5 PD |
| Cisplatin | 3.7 ± 0.9 | 0.780 | — | 4.6 ± 1.5 | 0.510 | — | 1/5 SD, 4/5 PD | 5/5 PD |
| TXT | 1.2 ± 0.3** | 0.380 | — | 1.1 ± 0.2* | 0.120 | — | 1/5 PR, 2/5 SD, 2/5 PD | 3/5 SD, 2/5 PD |

TABLE 8-continued

Antitumor activity of the treatment in the NCI-H1975-L858R-T790M-C797S model

| Treatment | RTV @ D22 | T/C @ D22 | Synergy ratio @ D22 | RTV @ D29 | T/C @ D29 | Synergy ratio @ D29 | mRECIST_best | mRECIST @ D29 |
|---|---|---|---|---|---|---|---|---|
| Compound 15 + Cisplatin | 1.5 ± 0.4** | 0.380 | 1.55 | 1.9 ± 0.7* | 0.210 | 1.57 | 1/5 PR, 1/5 SD, 2/5 PD | 1/5 SD, 4/5 PD |
| Compound 15 + TXT | 0.3 ± 0.0 **& | 0.120 | 2.53 | 0.4 ± 0.1* | 0.050 | 1.65 | 5/5 PR | 4/5 PR, 1/5 SD |

*p < 0.05 vs control,
**p < 0.01 vs control;
&p < 0.05 vs TXT;
Ratio > 1, Synergistic;
Ratio = 1, Additive;
Ratio < 1, Antagonistic

Example 11. Study on the Effect and the Potential Mechanism of Compound 31 or Compound 15 on the Growth of Gastric Cancer Cells (1) The sensitivity of gastric cancer cells to Compound 31 is closely related to the expression of Bcl-2, Bcl-xL and Bax.

The inventors first analyzed the basal expression levels of Bcl-2 family proteins in gastric cancer cell lines: AGS and NCI-N87 (purchased from Nanjing Cobioer Biotechnology Co., Ltd.), by Western blotting (FIG. 25). AGS and NCI-N87 are cell lines having high expression levels of Bcl-2 and Bcl-xL and high expression level of Bax.

The inventors evaluated the inhibiting effect of Compound 31 (supplied by Suzhou Ascentage Pharmaceutical) on the proliferation of gastric cancer cell lines by measuring the cell viability by CCK-8, and found that Compound 31 inhibited the proliferation of cell lines having high expression levels of Bcl-2, Bcl-xL and Bax (AGS and NCI-N87) in a concentration-dependent manner within 72 hours. The IC50s in AGS and NCI-N87 were 1.146±0.56 μM and 0.9007±0.23 μM, respectively (FIG. 26(a) and FIG. 26(b), Table 9). Thus, the sensitivity of gastric cancer cells to Compound 31 is closely related to the expression of Bcl-2, Bcl-xL and Bax.

TABLE 9

| Cell lines | IC$_{50}$ (μM) |
|---|---|
| AGS | 1.146 ± 0.56 |
| N87 | 0.9007 ± 0.23 |

(2) Compound 31 had no significant effect on cell cycle.

The inventors used the cell cycle detection kit to perform cell cycle assays, and the results showed that Compound 31 had no significant effect on cell cycle of both AGS and NCI-N87 gastric cancer cell lines (FIG. 27).

(3) Compound 15 significantly inhibited the proliferation of gastric cancer cells as the concentration increased in vivo.

In order to evaluate the anti-proliferative activity of Compound 15 in vivo, the inventors constructed a NCI-N87 xenograft model using nude mice. The NCI-N87 tumor-bearing mice were treated with different doses of Compound 15 by tail vein injection for 10 consecutive days. 5 weeks after the inoculation of tumor cells, NCI-N87 tumor-bearing mice were sacrificed to remove the tumors for study. The measurement of tumor volume found that Compound 15 as a single agent could exert a significant effect on inhibiting tumor growth as the dose increased. Upon the end point, the mouse tumor volumes in the 25 mg/kg group and the 50 mg/kg group grew to 700 mm$^3$ and 800 mm$^3$. The mouse tumor volume in the 100 mg/kg group was only about 400 mm$^3$, while the control group reached about 1300 mm$^3$ (FIG. 28(a)). There were significant differences among these four groups.

Figure 28A:
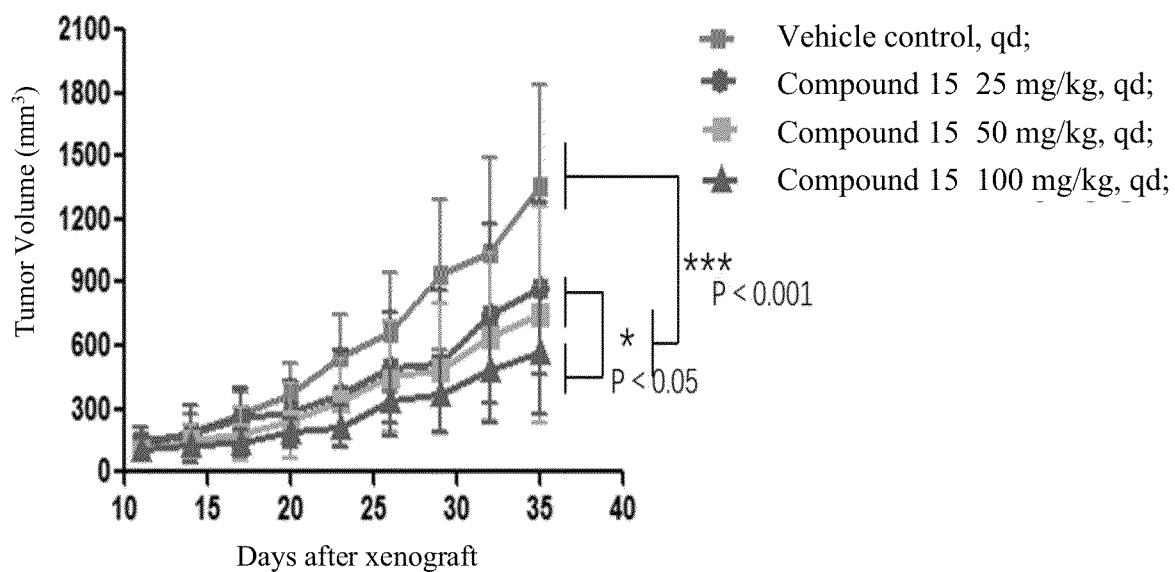
Figure 28B:
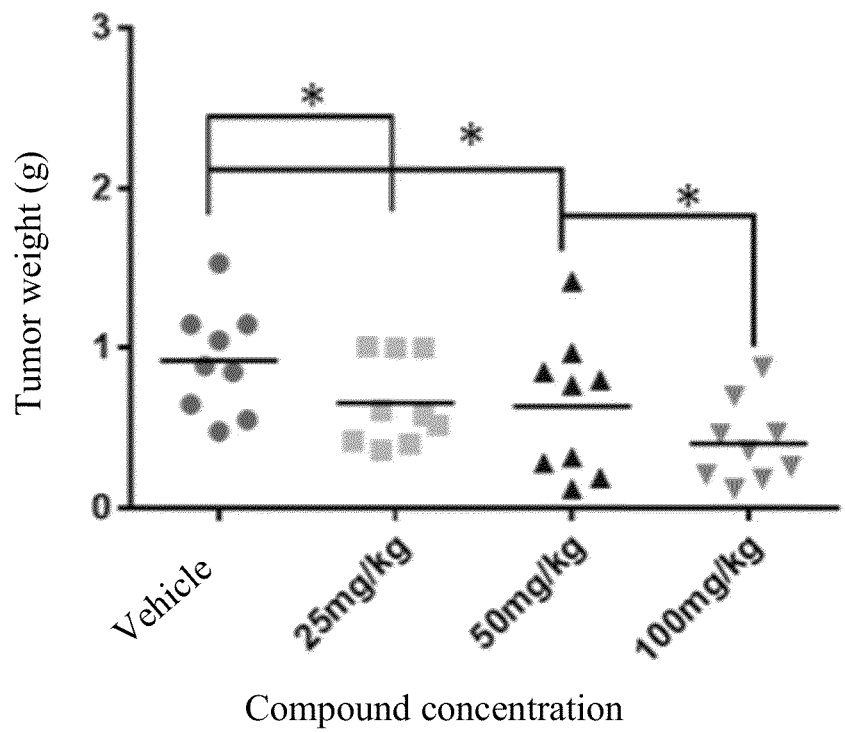
Figure 28C:
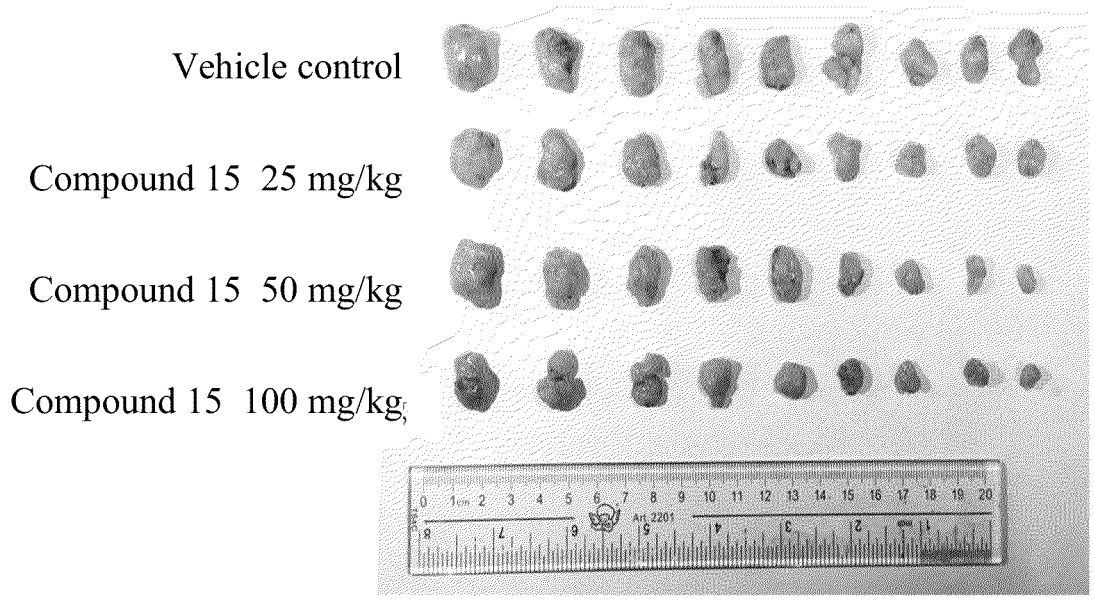
Figure 28D:
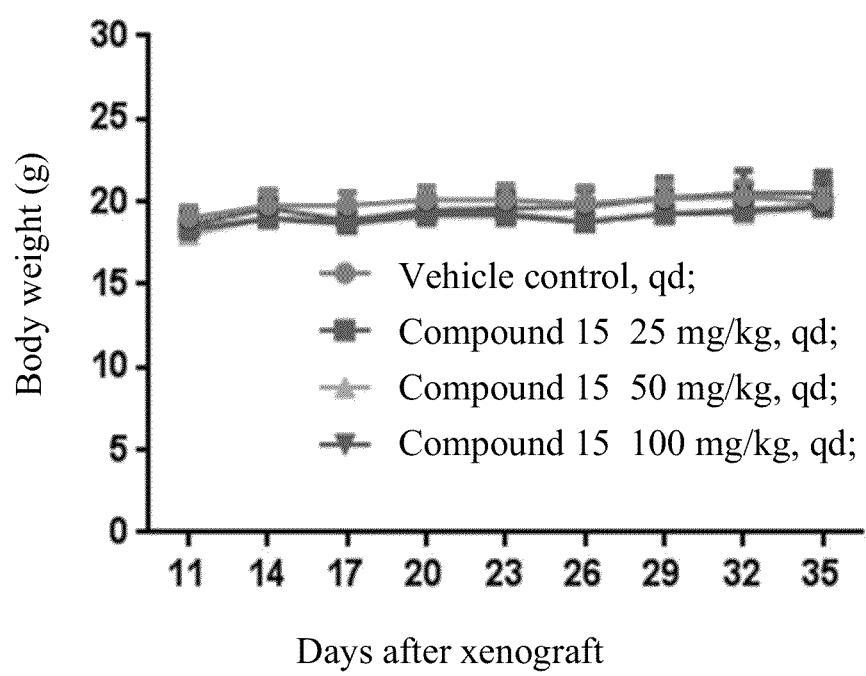
Figure 28E:
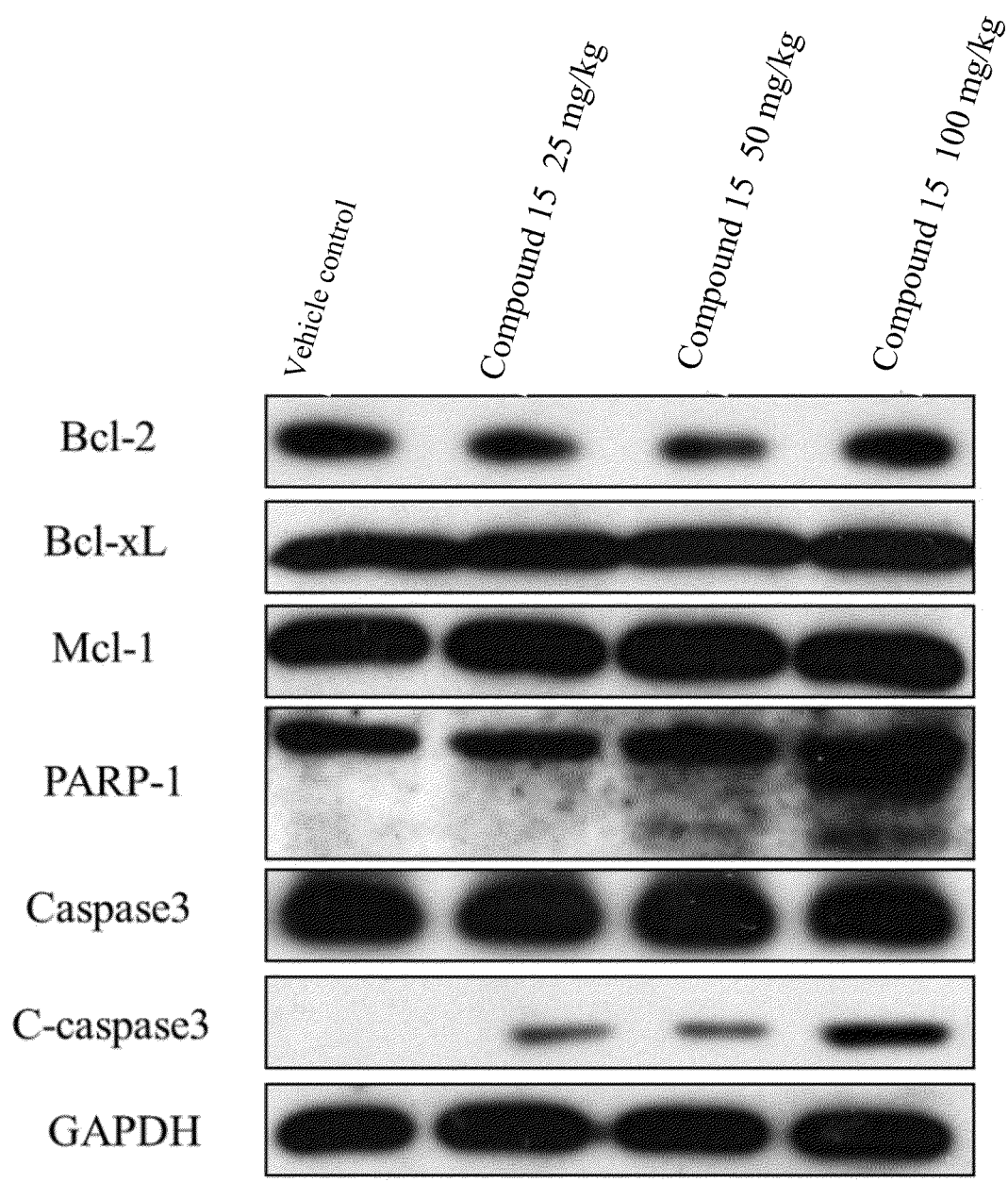
Figure 28F:
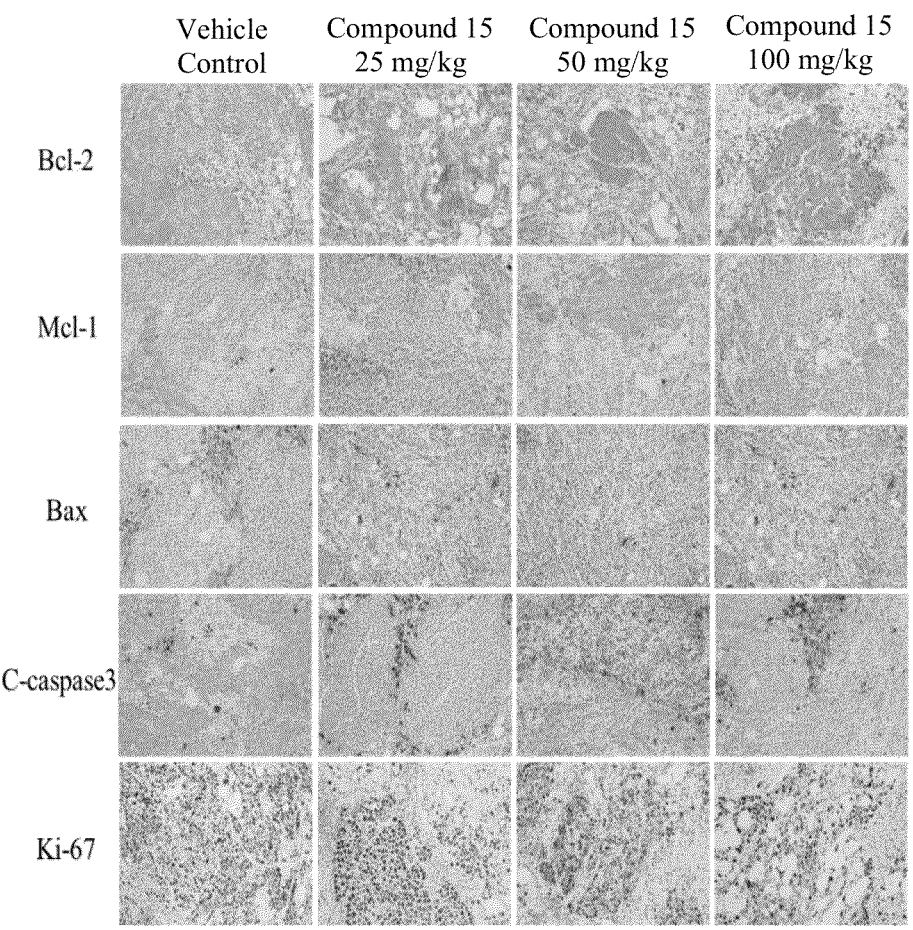
Figure 28F:
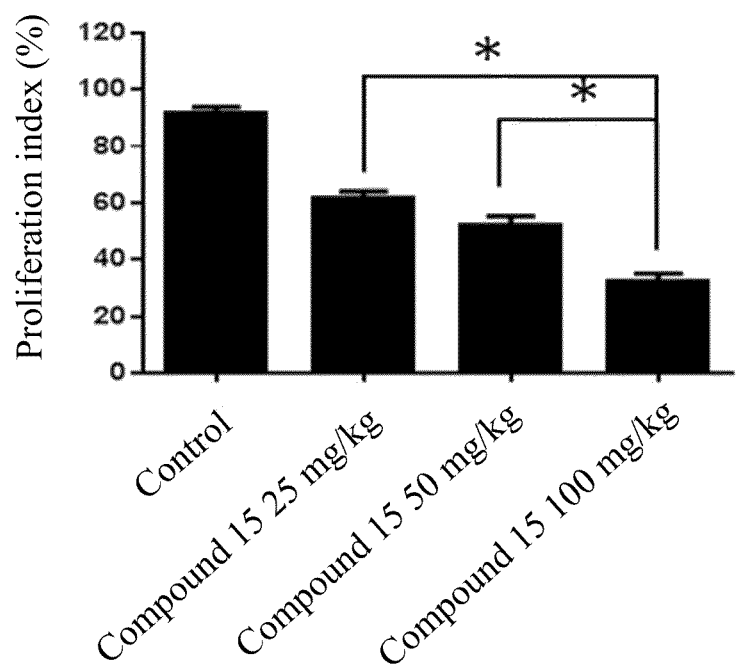

In the tumor issues removed from the scarified mice, it was found that as the dosing concentration increased, the weight and size of the xenograft tumors showed an evident trend of reduction (FIG. 28(b) and FIG. 28(c)). On the other hand, the measurement of mouse body weight showed no significant difference in body weight among the four groups (FIG. 28(d)), suggesting that Compound 15 had a safe dosing window.

The inventors extracted proteins from the removed tumor tissues and prepared tissue sections. It could be seen that the protein expression levels of cleaved-caspase3 and PARP-1 cleavage bands in the tumor tissue gradually increased as the dose increased (FIG. 28(e)). Immunohistochemical staining showed that the percentage of Ki67-positive cells in the 100 mg/kg group was significantly lower than other groups as the dosing concentration increased (FIG. 28(f)), suggesting the Compound 15 had inhibitory effect on the proliferation of gastric cancer cells in vivo.

Example 12. Study on the Effect and the Potential Mechanism of a Combination of Compound 15 or Compound 31 with 5-Fluorouracil on the Growth of Gastric Cancer Cells (1) Compound 31 combined with 5-FU enhanced the induction of apoptosis in gastric cancer cells.

The inventors chose to combine Compound 31 with one of the most common chemotherapeutic drugs in clinic, 5-fluorouracil (5-FU). In order to investigate the effect and the potential mechanisms of Compound 31 and 5-FU on the growth of gastric cancer cells, the inventors used the Annex-inV/PI staining to detect the apoptosis of two gastric cancer cells, AGS and NCI-N87, 48 hours after the treatment with Compound 31 (0.3 μM), 5-FU (3 μM), and the combination at specified concentrations. In AGS cells, the treatment with Compound 31 or 5-FU as a single agent resulted in an apoptosis rates of approximately 22% or 15%, whereas in the combination group, the proportion of apoptotic cells increased to 54% (FIG. 29(a)). In NCI-N87 cells, the combination group also achieved a higher apoptosis rate than the mono therapy groups, Compound 31 or 5-FU as a single agent leading to apoptosis rates of 24% or 18% while the combination group reaching an apoptosis rate of 46% (FIG. 29(a)).

At the same time, Western blotting showed that the cleaved-caspase3 and PARP-1 cleaved bands in AGS or NCI-N87 gastric cancer cells increased more significantly in the combination group than in either monotherapy-treated group (FIG. 29 (b).)). These results suggested that both in AGS and NCI-N87 gastric cancer cells, the combination of Compound 31 and 5-FU enhanced the induction of apoptosis in gastric cancer cells.

(2) The combination of Compound 15 and 5-FU significantly inhibited the proliferation of gastric cancer cells by inducing apoptosis in vivo.

In order to evaluate the anti-proliferative activity of the combination of Compound 15 and 5-FU in vivo, the inventors constructed a NCI-N87 xenograft model using nude mice. The mice were divided into 4 groups: vehicle, Compound 15 (50 mg/kg qd), 5-FU (25 mg/kg) and the combination. Compound 15 was administered through tail vein injection for 10 consecutive days, and 5-FU through tail vein injection once a week for two consecutive weeks. 5 weeks after the inoculation of the tumor cells, the mice were sacrificed to remove the tumors for study. The tumor volume of the combination group was significantly smaller than the other groups at any different measurement time. Upon the end point, the mouse tumor volumes of Compound 15 and 5-FU monotherapy grew to 1600 mm$^3$ and 2200 mm$^3$, and the tumor volume of combination group was only about 1000 mm$^3$ while the control group reached about 2600 mm$^3$ (FIG. 30(a)). There were significant differences among these four groups.

Figure 30A:
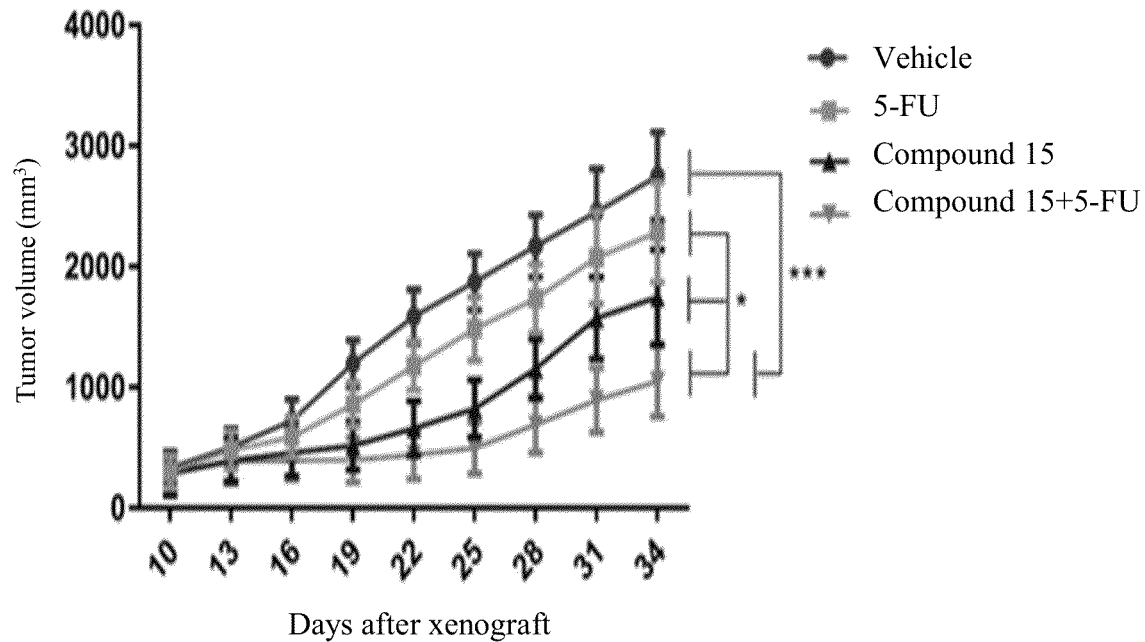
Figure 30B:
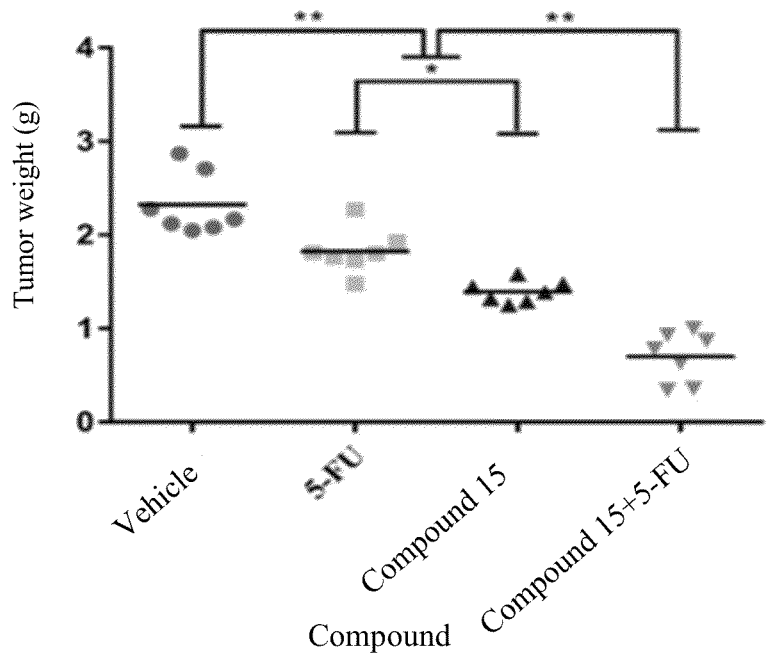
Figure 30C:
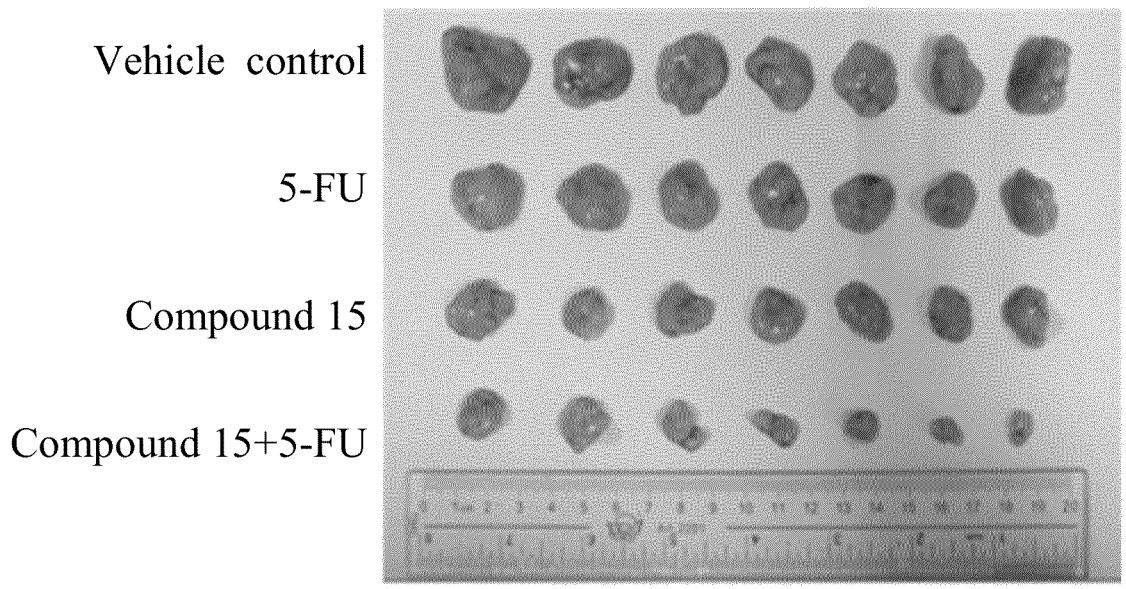
Figure 30D:
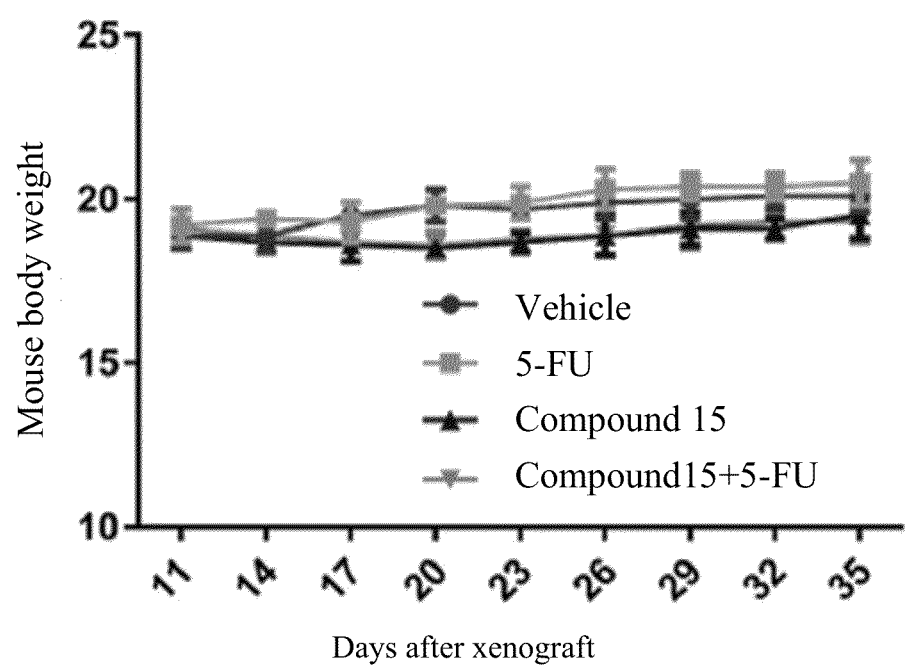
Figure 30E:
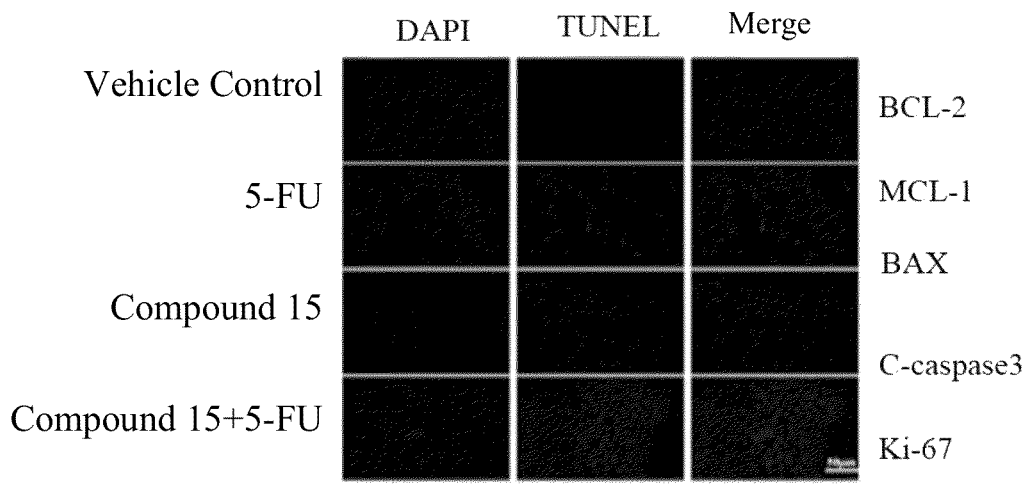
Figure 30E:
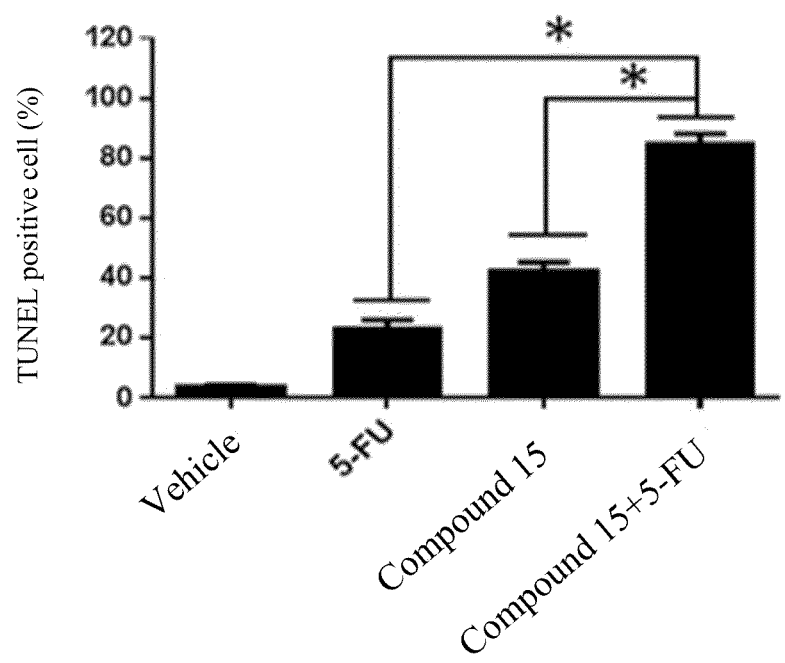
Figure 30F:
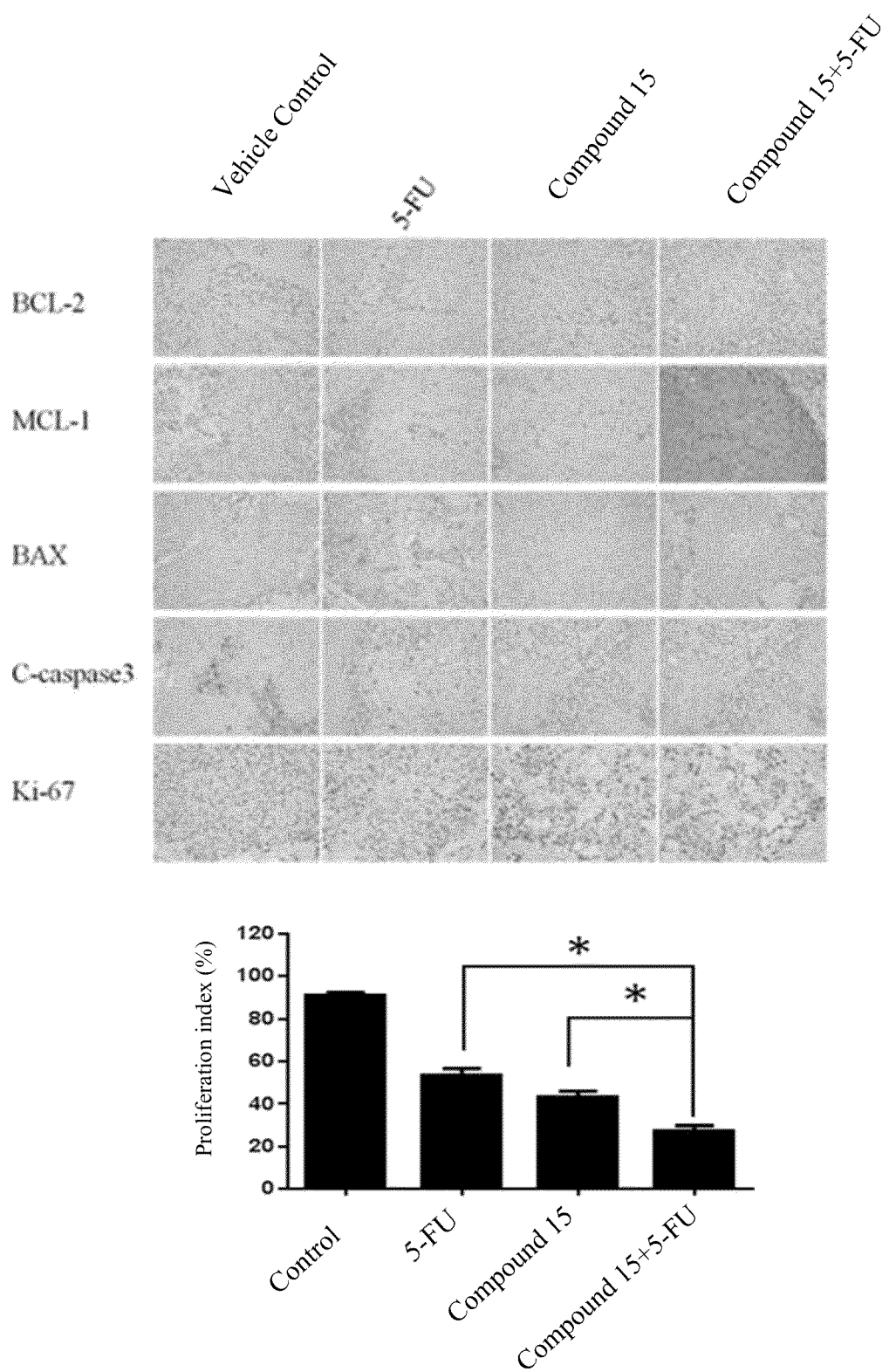

Significant differences in the weight and size of the xanograft tumors among the combination group and the other groups were also found in the tumor tissues removed from the scarified mice, the combination group being significantly smaller than the other groups (FIG. 30(b) and FIG. 30(c)). On the other hand, the measurement of mouse body weight showed no significant difference among the four groups. Groups treated with Compound 15 and the combination rebounded after a brief weight loss (FIG. 30(d)), suggesting that Compound 15 had a good dosing window.

The inventors embedded the removed tumor tissues to prepare sections, and used TUNEL kit and immunohistochemistry assays for detection. The TUNEL-positive cells in combination group were significantly more than the other groups (FIG. 30(e)). Compared with the other groups, the expression of cleaved-caspase3 was also significantly increased in the combination group (FIG. 30(f)), which all suggested that combination of Compound 15 and 5-FU more effectively induced apoptosis in gastric cancer cells in vivo. The percentage of Ki67-positive cells in the combination group was also significantly lower than that in the groups with Compound 15 or 5-FU or the control group (FIG. 30(f)), suggesting the more effective inhibiting effect of Compound 15 in combination with 5-FU on proliferation of gastric cancer cells in vivo.

Example 13. Study on the Effect of Compound 31 in Combination with Docetaxel (TXT) on the Growth of Gastric Cancer Cells Anti-proliferation effects were detected by CCK-8 (Cell Counting Kit-8) assay based on water soluble tetrazolium salt (WST). Briefly, NCI-N87 cells were seeded in 96-well plates and treated with different Compound 31 at different concentrations for 72 hours. To test the synergistic effect between Compound 31 and docetaxel, docetaxel was added to each well at a concentration of 0.001 nM, 0.1 nM or 10 nM. Each concentration was prepared in triplicates. At the end of treatment, CCK-8 agents (10 μL/well) were added to the 96-well plate, and incubated with the cells for 2 hours. The OD450 value was measured using a microplate reader. The percent cell viability was calculated using mean OD value of the triplicate wells by the following formula:

(O.D. test well–O.D. blank control well)/(O.D. cell control well–O.D. blank control well)×100%.

The IC$_{50}$ was calculated using the nonlinear regression data analysis method of Graphpad Prism 6.0 software (Golden software, Golden, USA). The results are shown in FIG. 31.

The IC$_{50}$ value of Compound 31 in NCI-N87 cells was 0.405 UM as shown in FIG. 31. When cells were co-treated with docetaxel at a concentration of 0.001 nM, 0.1 nM or 10 nM, the IC$_{50}$ values were reduced to 0.012, 0.014 and 0.004 μM. A significant decrease in IC$_{50}$ values indicated that Compound 31 and docetaxel had strong synergistic anti-proliferative activity in NCI-N87 cells.

Example 14. Study on the Effect of Compound 31 in Combination with Panobinostat on the Growth of Gastric Cancer Cells Anti-proliferation effects were detected by CCK-8 (Cell Counting Kit-8) assay based on water soluble tetrazolium salt (WST). Briefly, HGC-27 cells were seeded in 96-well plates and treated with Compound 31, panobinostat or the combination of Compound 31 and panobinostat at different concentrations for 24 hours. At the end of treatment, CCK-8 reagents (10 μL/well) were added to the 96-well plate, and incubated with the cells for 2 hours. The cell viability of each treatment group under each concentration was calculated, and the results are shown in FIG. 32.

As shown in FIG. 32, the treatment of cells with the combination of Compound 31 and panobinostat at different concentrations resulted in a more significant decrease in cell viability as compared to the treatment with Compound 31 or panobinostat alone. The treatment with Compound 31 in combination with panobinostat had a stronger anti-proliferative activity in HGC-27 cells.

What is claimed is:

1. A method of treating cancer comprising administering to a subject in need thereof a therapeutically effective amount of a Bcl-2/Bcl-xL inhibitor and a therapeutically effective amount of a chemotherapeutic agent, wherein the Bcl-2/Bcl-xL inhibitor is

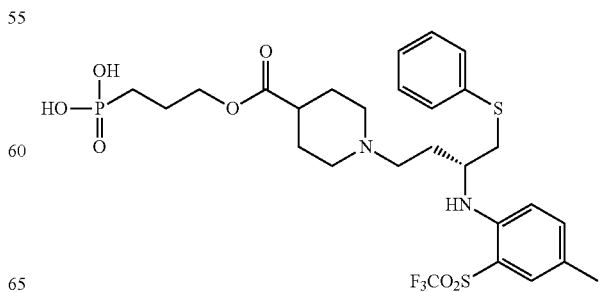

-continued

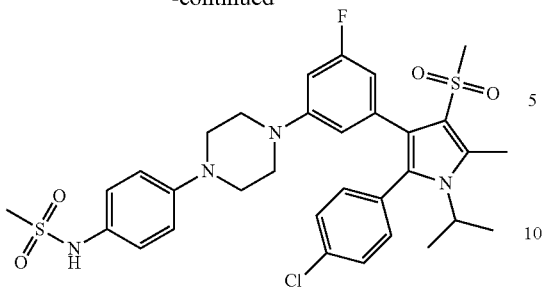

or a pharmaceutically acceptable salt thereof,
wherein the chemotherapeutic agent is docetaxel or paclitaxel, and
wherein the cancer is small cell lung cancer.

2. The method according to claim 1, wherein the cancer is a metastatic solid tumor.

3. The method according to claim 1, wherein the cancer is Bcl-2/Bcl-xL and Bax positive.

4. The method according to claim 1, wherein the Bcl-2/Bcl-xL inhibitor is administered at an amount from about 0.005 to about 500 mg/day, from about 0.05 to about 250 mg/day or from about 0.5 to about 100 mg/day.

* * * * *